United States Patent
Ramasamy et al.

(10) Patent No.: US 11,274,329 B2
(45) Date of Patent: *Mar. 15, 2022

(54) ELECTROCHEMICAL SENSORS AND METHODS FOR USING ELECTROCHEMICAL SENSORS TO DETECT PLANT PATHOGEN INFECTION

(71) Applicant: University of Georgia Research Foundation, Inc., Athens, GA (US)

(72) Inventors: Ramaraja P. Ramasamy, Watkinsville, GA (US); Yi Fang, Athens, GA (US)

(73) Assignee: University of Georgia Research Foundation, Inc., Athens, GA (US)

(*) Notice: Subject to any disclaimer, the term of this patent is extended or adjusted under 35 U.S.C. 154(b) by 53 days.

This patent is subject to a terminal disclaimer.

(21) Appl. No.: 16/710,059

(22) Filed: Dec. 11, 2019

(65) Prior Publication Data
US 2020/0115730 A1    Apr. 16, 2020

Related U.S. Application Data

(63) Continuation of application No. 15/566,438, filed as application No. PCT/US2016/027735 on Apr. 15, 2016, now Pat. No. 10,526,633.

(60) Provisional application No. 62/147,763, filed on Apr. 15, 2015.

(51) Int. Cl.
| | |
|---|---|
| G01N 27/327 | (2006.01) |
| C12Q 1/00 | (2006.01) |
| G01N 33/00 | (2006.01) |
| G01N 33/02 | (2006.01) |
| B82Y 30/00 | (2011.01) |

(Continued)

(52) U.S. Cl.
CPC ............ *C12Q 1/005* (2013.01); *B82Y 30/00* (2013.01); *G01N 27/3277* (2013.01); *G01N 27/3278* (2013.01); *G01N 33/0047* (2013.01); *G01N 33/0098* (2013.01); *G01N 33/025* (2013.01); *G01N 33/483* (2013.01); *A01G 9/26* (2013.01)

(58) Field of Classification Search
CPC .......... A01G 9/24; A01G 9/26; G01N 33/025; G01N 33/0098; G01N 33/0047; G01N 27/327; G01N 27/3271; C12Q 1/005
See application file for complete search history.

(56) References Cited

U.S. PATENT DOCUMENTS

| | | | |
|---|---|---|---|
| 10,526,633 B2* | 1/2020 | Ramasamy | ........ G01N 33/0098 |
| 2013/0334042 A1 | 12/2013 | Grieve | |

FOREIGN PATENT DOCUMENTS

| | | |
|---|---|---|
| CN | 100493212 | 5/2009 |
| WO | 2014145377 | 9/2014 |

OTHER PUBLICATIONS

Fang, Y., et al., "Plant Volatile Sensor: Enzymatic Transducer for Selective and Sensitive Determination of Methyl; Salicyate," Meeting Abstract 414 of the 225th ECS Meeting, May 11-15, 2014, pp. 1-3.

(Continued)

*Primary Examiner* — Alexander S Noguerola
(74) *Attorney, Agent, or Firm* — Thomas Horstemeyer, LLP

(57) ABSTRACT

Provided herein are plant/plant pathogen volatile compound electrochemical sensors, plant/plant pathogen volatile detection systems, and methods for detecting stress-induced plant volatile compounds and/or a plant-pathogen emitted volatile compounds.

20 Claims, 37 Drawing Sheets

(51) Int. Cl.
*G01N 33/483* (2006.01)
*A01G 9/26* (2006.01)

(56) References Cited

OTHER PUBLICATIONS

Cardoza, Yasmin, et al., "In Vivo Volatile Emissions from Peanut Plants Induced by Simultaneous Fungal Infection and Insect Damage," Journal of Chemical Ecology, 2002, pp. 161-174, vol. 28, No. 1.
Umasankar, Yogeswaran and Ramaraja P. Ramasay, et al., "Highly sensitive electrochemical detection of methyl salicylate using electroactive gold nanoparticles," Analyst, 2013, pp. 6623-6631, plus Supplementary Data (p. 1-9), vol. 138, RSC Publishing, doi: 10.1039/c3an01295f.
Hasunuma, Tomohisa, et al., "Real-Time Quantification of Methanol in Plants Using a Hybrid Alcohol Oxidase-Peroxidase Biosensor," Analytical Chemistry, 2004, pp. 1500-1506, vol. 76, No. 5, doi: 10.1021/ac035309q.
Entry for methyl salicylate esterase activity in the on-line *Arabidoposis* Information Resource (TAIR), last modifed Aug. 30, 2010, but downloaded Feb. 7, 2019 (https://www.arabidopsis.org/servlets/TairObject?type=keyword&id=31249).
Ozoner, Seyda Korkut, et al., "Enzyme Based Phenol Biosensors," Environmental Biosensors, 2011, pp. 319-340, edition by Prof. Vernon Somerset, IntechOpen, https://www.intechopen.com/books/environmental-biosensors/enzyme-based-phenol-biosensors.
Azevedo, Ana M., et al. "Horseradish peroxidase: a valuable tool in biotechnology," Biotechnology Annual Review, 2003, pp. 199-247, vol. 9, doi: 10.1016/S1387-2656(03)09003-3.
Fang, Yi, et al., "Electrochemical detection of p-ethylguaiacol, a fungi infected fruit volatile using metal oxide nanoparticles," Analyst, 2014, pp. 3804-3810, vol. 139, doi: 10.1039/c4an00384e.
Tsai, Yu-Chen, et al., "Amperometric ethanol biosensor based on poly(vinyl alcohol)-multiwalled carbon nanotube-alcohol dehydrogenase biocomposite," Biosensors and Bioelectronics, 2007, pp. 3051-3056, vol. 22, doi: 10.1016/j.bios.2007.01.005.
Zhou, Bo and Jun Wang, "Discrimination of different types damage of rice plants by electronic nose," Biosystems Engineering, 2011, pp. 250-257, vol. 109, Elsevier Ltd, doi: 10.1016/j.biosystemseng.2011.03.003.
Fang, Yi, et al., "Plant Volatile Sensor: Enzymatic Transducer for Selective and Sensitive Determination of Methyl Salicyalte," Abstract for 225th ECS Meeting, Orlando, Fl. Presented May 11-15, 2015, p. 1.
Fang, Yi, et al., "Plant Volatile Sensor: Enzymatic Transducer for Selective and Sensitive Determination of Methyl Salicyalte," 225th ECS Meeting, Orlando, Fl. Presented May 11-15, 2015, p. 1-23.
Buttery, R. G., et al., "Characterization of some volatile constituents of bell peppers," Journal of Agricultural and Food Chemistry, 1969, pp. 1322-1327, vol. 17 No. 6.
Cosnier, Serge and Christophe Innocent, "A new strategy for the construction of a tyrosinase-based amperometric phenol and o-diphenol sensor," Bioelectrochemistry and Bioenergetics, 1993, pp. 147-160, vol. 31, No. 2.
Ellis, M.A. and G.G. Grove, "Leather rot in Ohio strawberries," Plant Disease, 1983, pp. 549, vol. 67, No. 5.
Enache, Teodor Adrian and Ana Maria Oliveira-Brett, "Phenol and Para-substituted Phenols Electrochemical Oxidation Pathways," Journal of Electroanalytical Chemistry, 2011, pp. 6-19, vol. 655, No. 1, doi: 10.1016/ielechem.2011.02.022.
Espin, J.C., et al., "Kinetic characterization of the substiate specificity and mechanism of mushroom tyrosinase," European Journal of Biochemistry, 2000, pp. 1270-1279, vol. 267, No. 5.
Fang, Yi and Ramaraja P. Ramasamy, "Current and Prospective Methods for Plant Disease Detection," Biosensors, 2015, pp. 537-561, vol. 5, No. 3.

Fang, Yi, et al., "A novel bi-enzyme electrochemical biosensor for selective and sensitive determination of methyl salicylate," Biosensors and Bioelectronics, 2016, pp. 39-45, vol. 81, doi: 10.1016/j.bios.2016.01.095.
Fariña, Laura, et al., "Determination of volatile phenols in red wines by dispersive liquid-liquid microextraction and gas chromatography-mass spectrometry detection," Journal of Chromatography A, 2007, pp. 46-50, vol. 1157, No. 1, doi: 10.1016/j.chroma.2007.05.006.
Jelen, H.H, et al., "Main compounds responsible for off-odour of strawberries infected by Phytophthora cactorum," Letters in Applied Microbiology, 2005, pp. 255-259, vol. 40, No. 4, doi: 10.1111/j.1472-765X.2005.01668.x.
Katagiri, Masayuki, et al., "Salicylate hydroxylase, a Monooxygenase Requiring Flavin Adenine Dinucleotide: II the mechanism of salicylate hydroxylation to catechol," Journal of Biological Chemistry, 1965, pp. 3414-3417, vol. 240, No. 8.
Laothawornkitkul, Jullada, et al., "Discrimination of Plant Volatile Signatures by an Electronic Nose: A Potential Technology for Plant Pest and Disease Monitoring," Environmental Science & Technology, 2008, pp. 8433-8439, vol. 42, No. 22, doi: 10.1021/es/801738s.
Li, Henry, et al., "Quantitative Analysis of Bioactive NAD+ Regenerated by NADH Electro-oxidation," ACS Catalysis, 2012, pp. 2572-2576, vol. 2, ACS Publications, doi: 10.1021/cs3004598.
Martorell, N., et al., "Determination of 4-ethylguaiacol and 4-ethylphenol in red wines using headspace-solid-phase microextraction-gas chromatography," Journal of Chromatography A, 2002, pp. 349-354, vol. 975, No. 2.
Parimi, Naga S., et al., "Kinetic and Mechanistic Parameters of Laccase Catalyzed Direct Electrochemical Oxygen Reduction Reaction," ACS Catalysis, 2012, pp. 38-44, vol. 2, ACS Publications, doi: 10.1021/cs200527c.
Pollnitz, Alan P., et al., "Quantitative analysis of 4-ethylphenol and 4-ethylguaiacol in red wine," Journal of Chromatography A, 2000, pp. 101-109, vol. 874.
Ramasamy, Ramaraja P., et al., "High electrocatalytic activity of tethered multicopper oxidase-carbon nanotube conjugates," Chem Comm, 2010, pp. 6045-6047, vol. 46, doi: 10.1039/c0cc00911c.
Rassaei, Liza, et al., "Substrate-dependent kinetics in tyrosinase-based biosensing: amperometry vs. spectrophotometry," Analytical and Bioanalytical Chemistry, 2012, pp. 1577-1584, vol. 403, doi: 10.1007/s00216-012-5964-0.
Umasankar, Yogeswaran and Ramaraja P. Ramasamy, "On the bio-electrocatalytic activity of tyrosinase for oxygen reduction reaction," Catalysis Science & Technology, 2013, pp. 2546-, vol. 3, RCS Publishing, doi: 10.1039/c3cy00180f.
White-Stevens, Rodric H., and Henry Kamin, "Studies of a Flavoprotein, Salicylate Hydroxylase: I. Preparation, Properties, and the Uncoupling of Oxygen Reduction from Hydroxylation," Journal of Biological Chemistry, 1972, pp. 2358-2370, vol. 247, No. 8, Printed in the U.S.
Wu, L et al. Amperometric sensor for ethanol based on one-step electropolymerization of thionine-carbon nanofiber nanocomposite containing alcohol oxidase. Talanta, vol. 74. pp. 387-392. Oct. 2, 2007.
Park, KC et al. Electroantennogram responses of a parasitic wasp, *Microplitis croceipes*, to 4 host-related volatile and anthropogenic compounds. Physiological Entomology, vol. 26. pp. 69-77. 2001.
Smutok, 0 et al. a Reagentless bienzyme amperometric biosensor based on alcohol oxidase/peroxidase and an Os-complex modified electrodeposition paint. Sensors and actuators. vol. B 113. pp. 590-598. Sep. 6, 2005.
Anand, S Microbiological and molecular methods for the study of ochratoxin a in foods and its Control. University of Mysore. Human resource development. Central food technological research institute. May 2006.
Arrocha, AA et al. Enzyme orientation for direct electron transfer in an enzymatic fuel cell with alcohol oxidase and laccase electrodes. Biosensors and bioelectronics, vol. 61. pp. 569-574. Jun. 9, 2014.
Yang, X-Q et al. Enhanced electrochemical activity of redox-labels in multi-layered protein films on indium tin oxide nanoparticle-based electrode. Analytic Chimica Acta. vol. 632. pp. 15-20. Sep. 25, 2007.

(56) References Cited

OTHER PUBLICATIONS

Arya, SK et al. BiOensor for total cholesterol estimation using N-(2-aminoethyl)-3-aminopropyltrimethoxysilane self-assembled monolayer. Analytical and Bioanalytical Chemistry, vol. 389. pp. 2235-2242. Nov. 6, 2007.

Kuswandi, Bet al. Recent progress in alcohol biosensors. OA alcohol. vol. 18. Jan. 2014.

Fang, Yet al. Plant volatile sensor: Enzymatic transducer for selective and sensitive determination of methyl salicylate. 225th ECS Meeting. May 13, 2014.

* cited by examiner

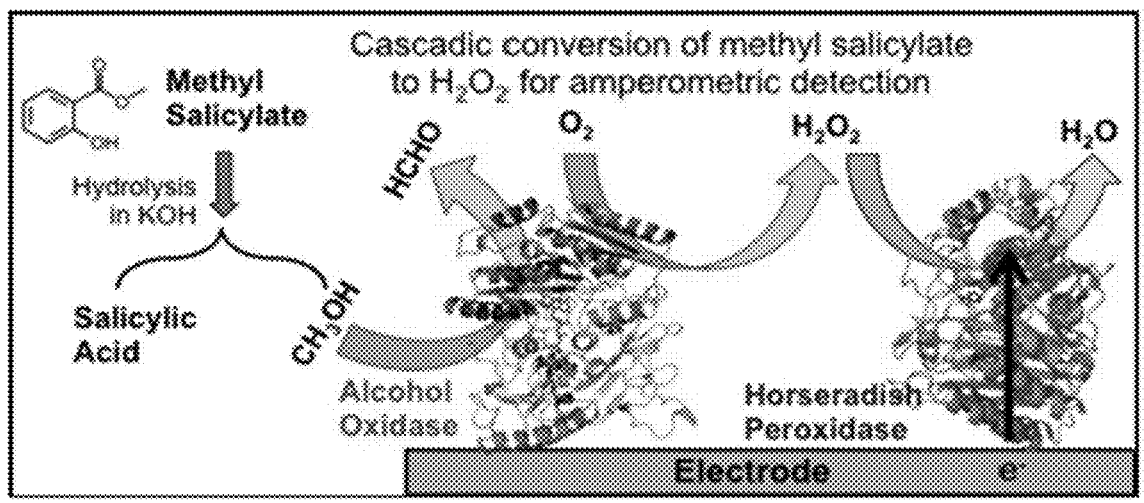
*FIG. 4A*
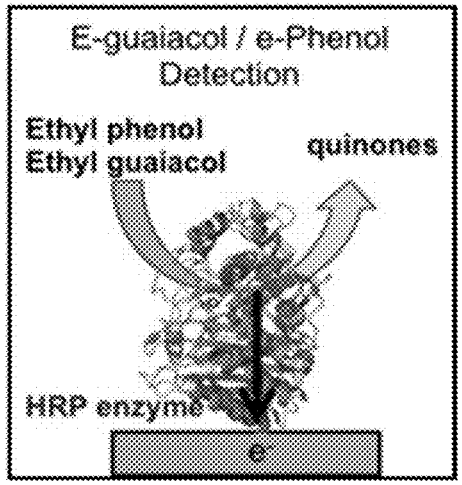
*FIG. 4B*
*FIG. 4C*
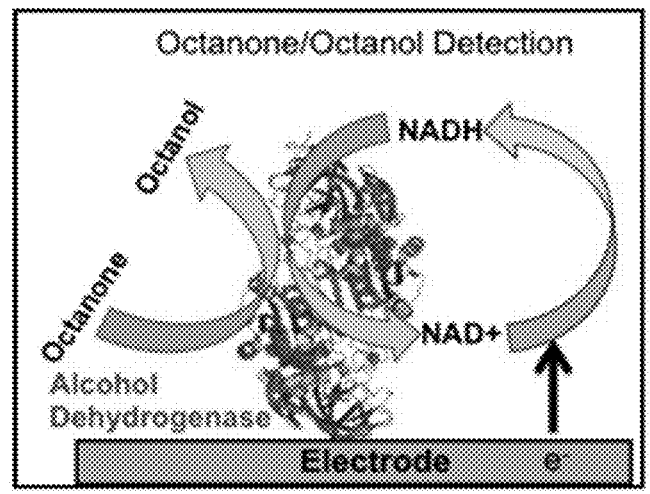

FIG. 5A
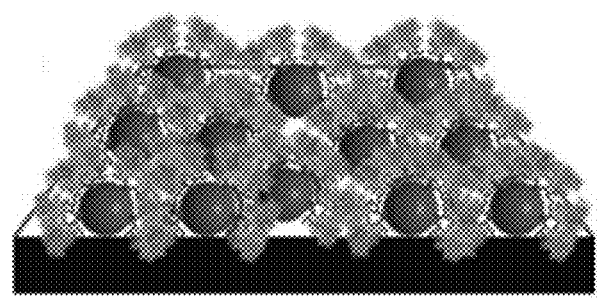
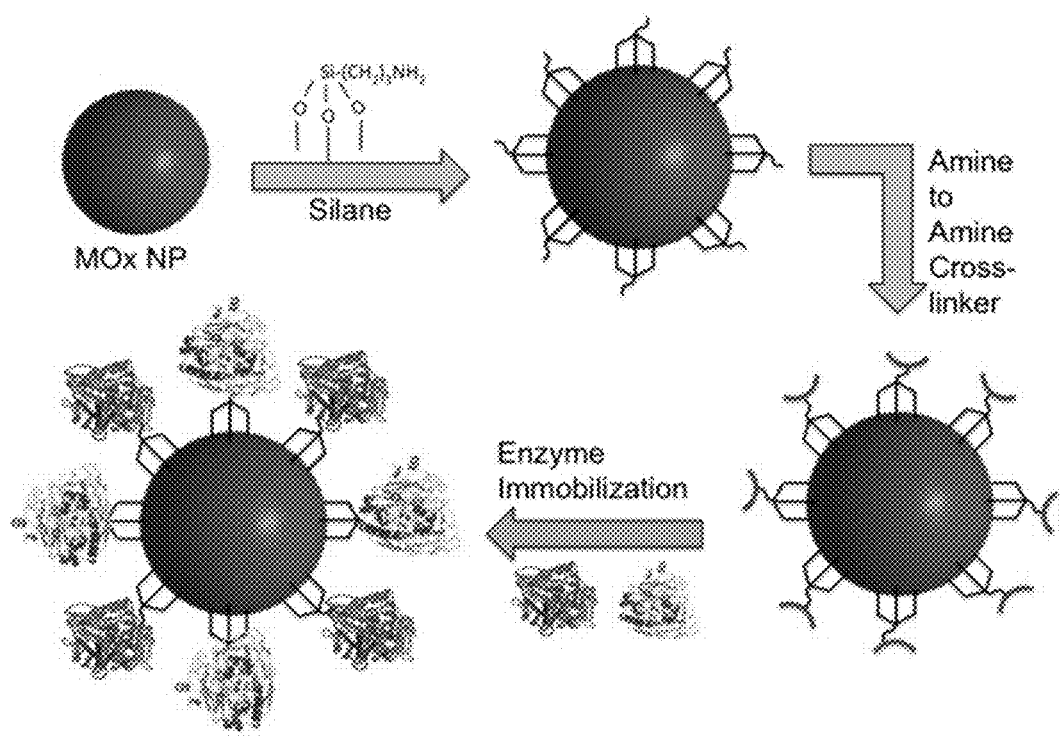
FIG. 5B

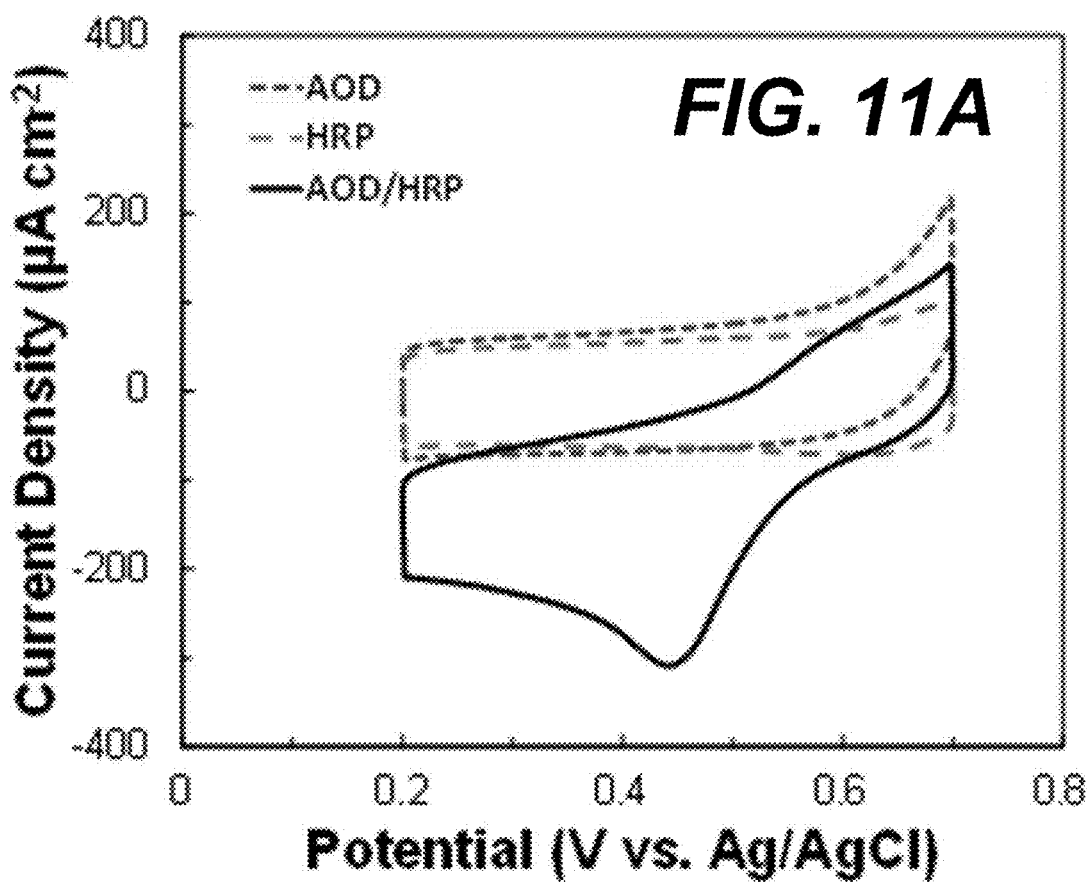
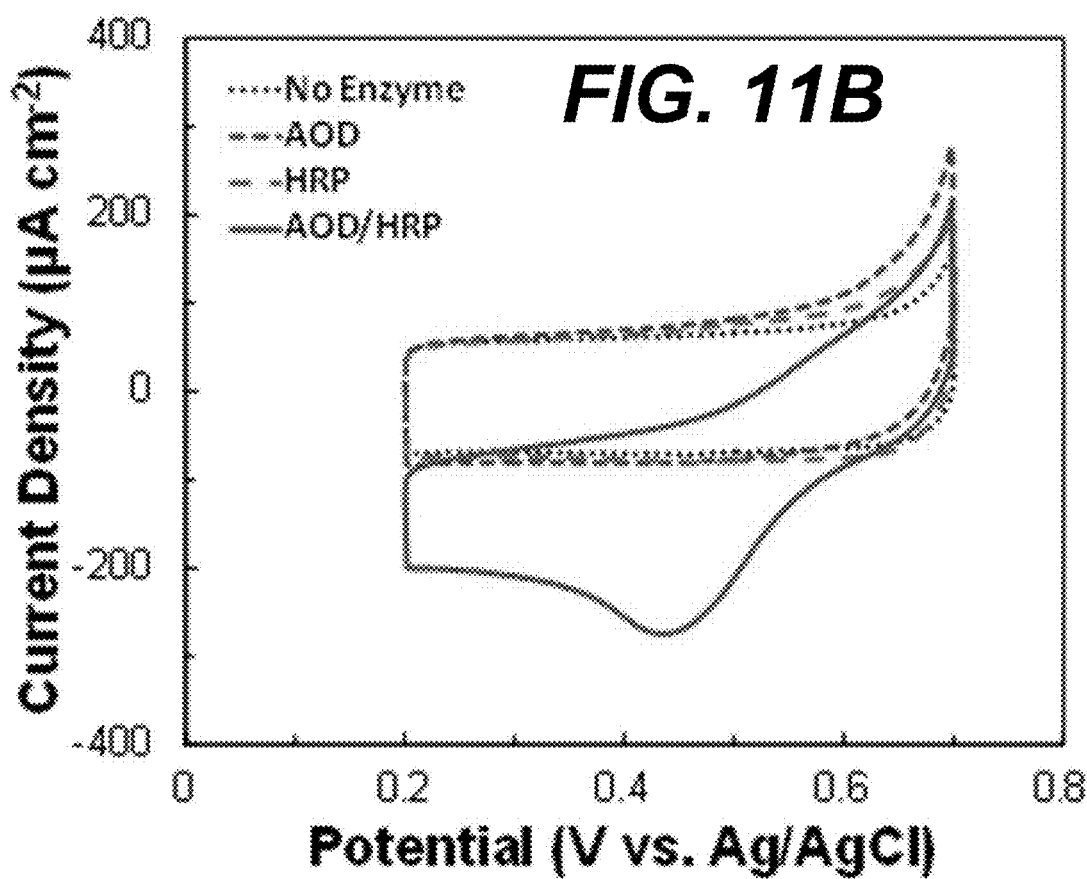

FIG. 15A
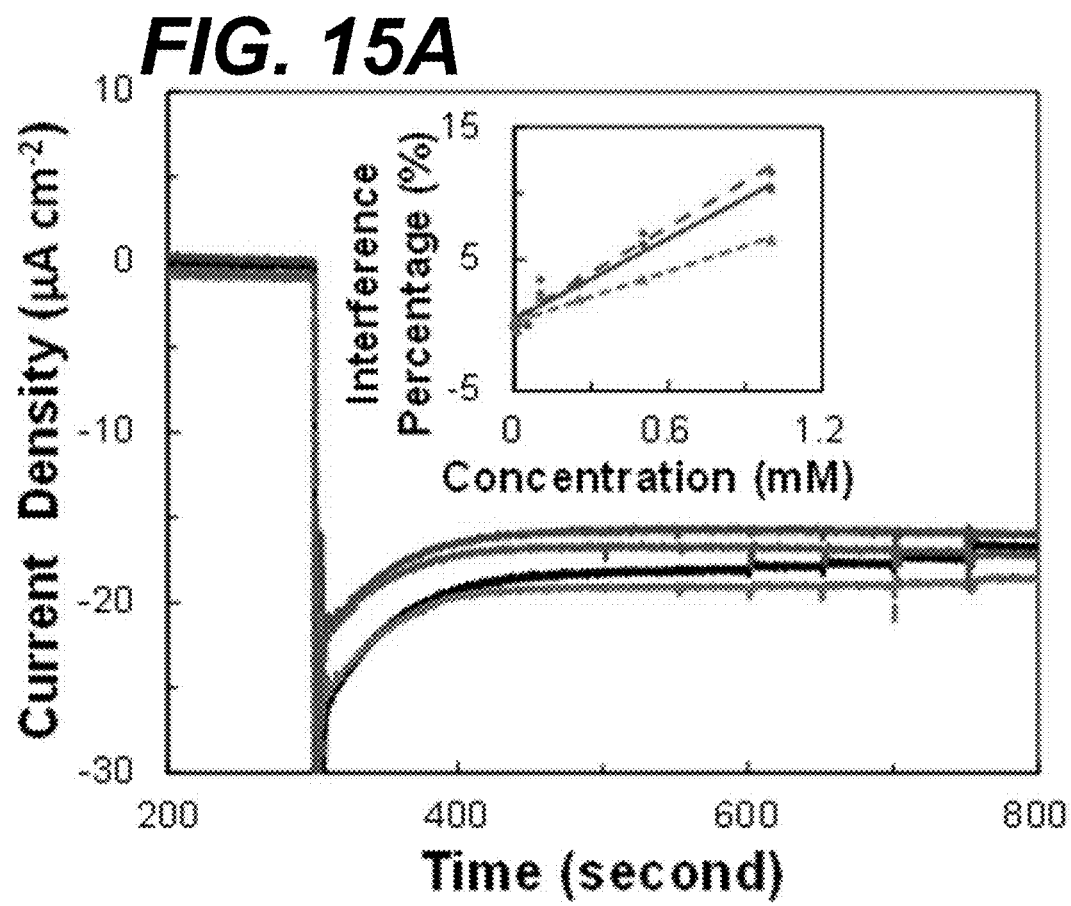
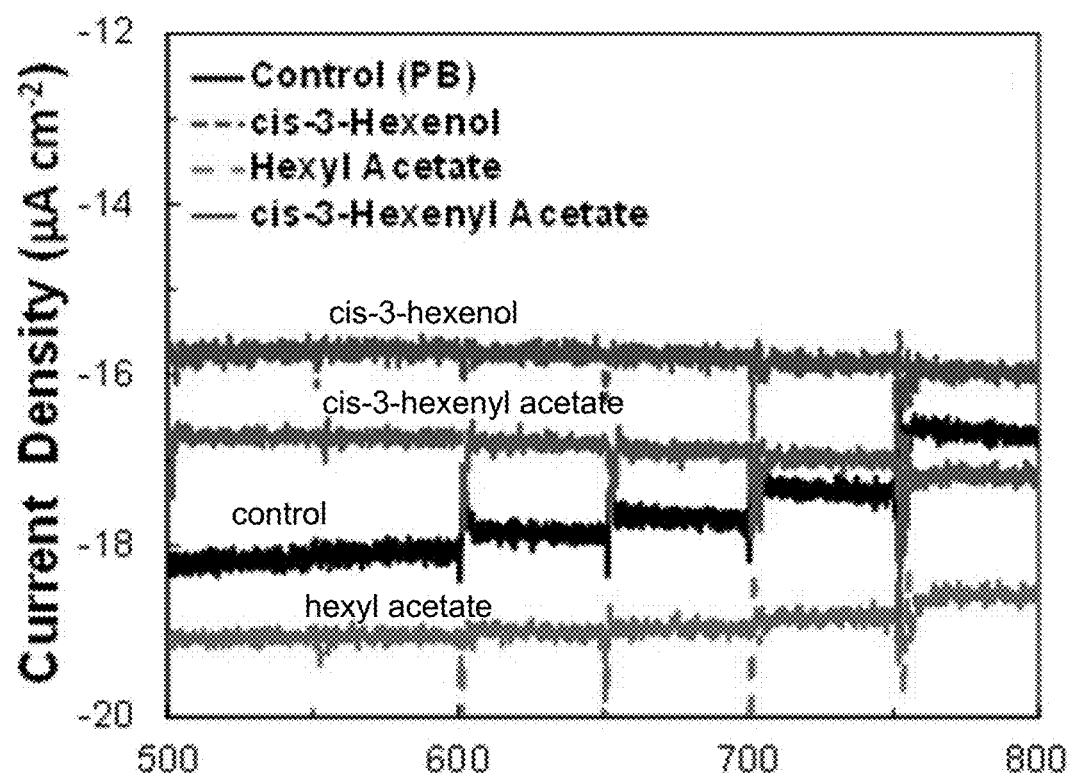
FIG. 15B

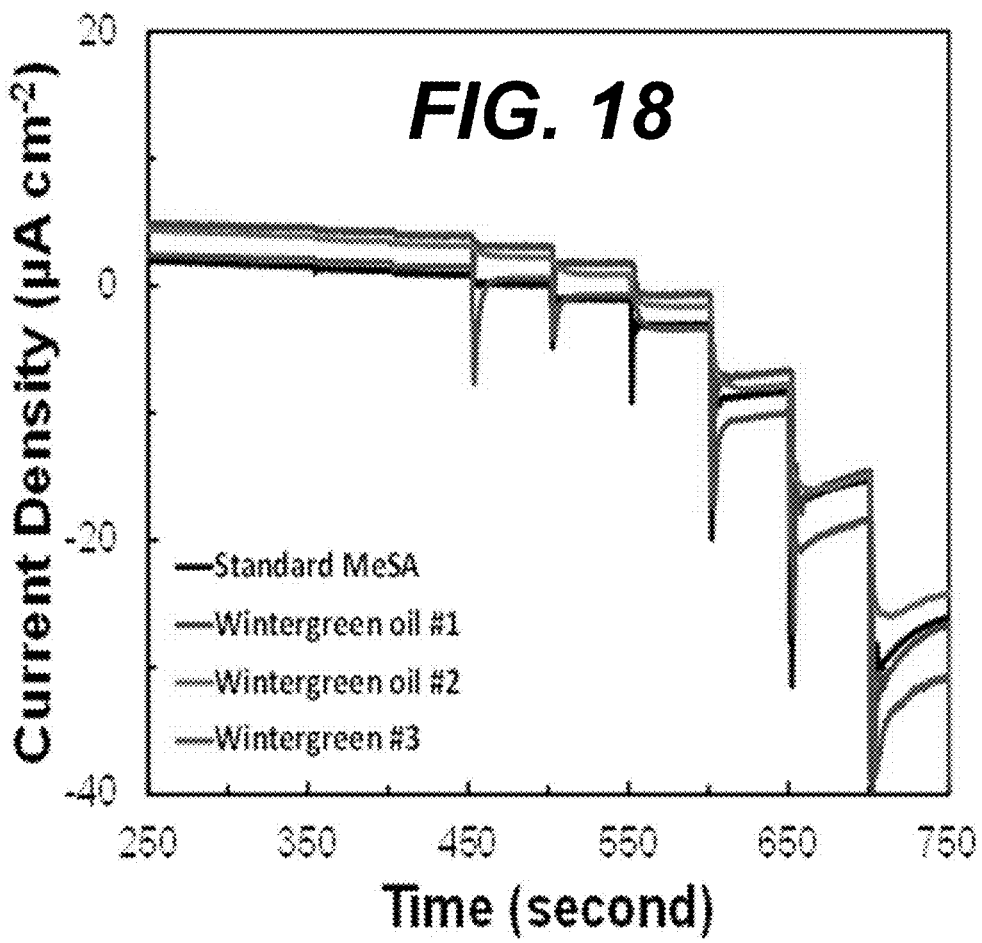
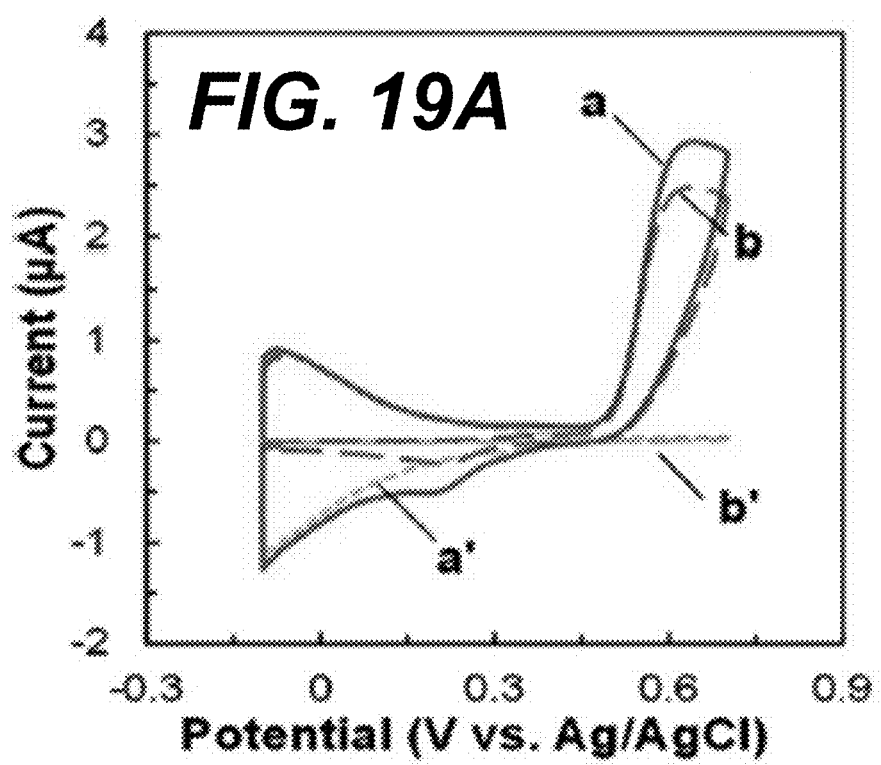

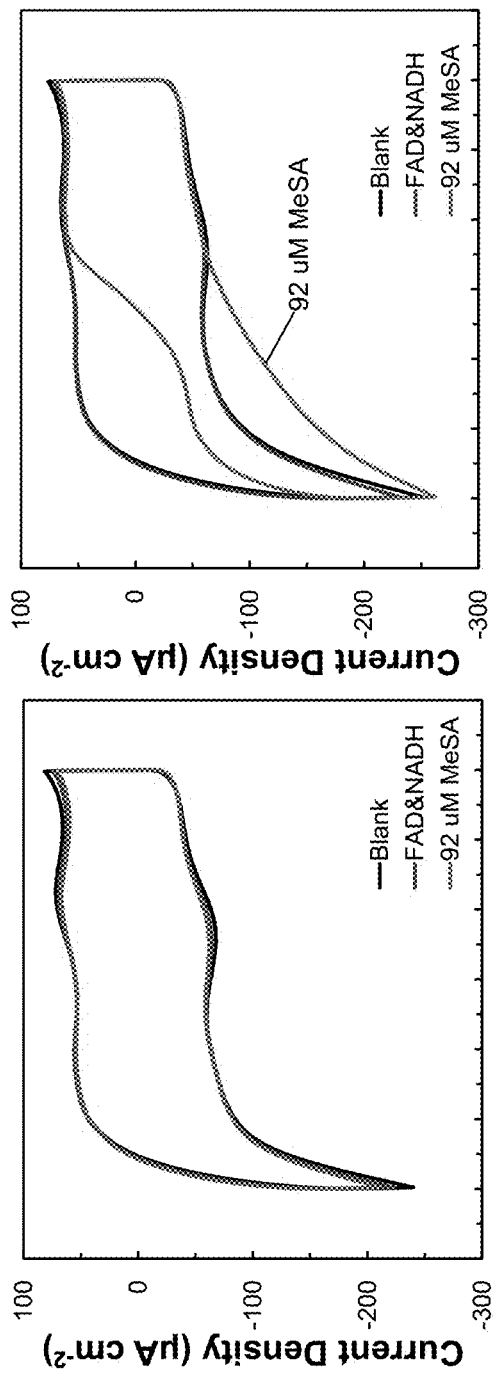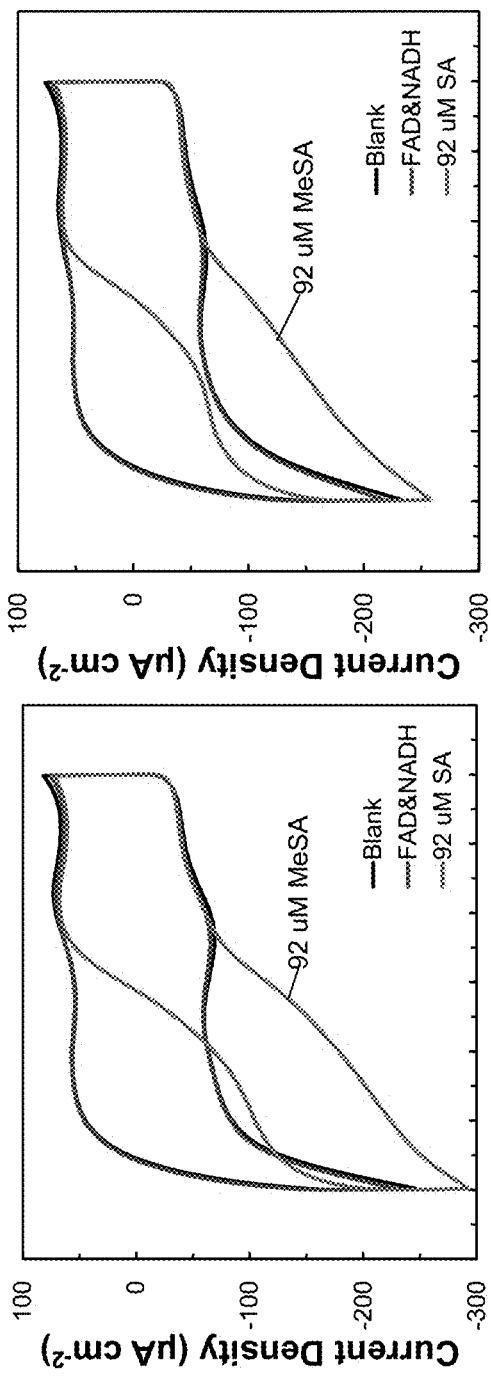
FIG. 32A  FIG. 32B  FIG. 32C  FIG. 32D ic SENSORS AND
METHODS FOR USING
ELECTROCHEMICAL SENSORS TO
DETECT PLANT PATHOGEN INFECTION

CROSS-REFERENCE TO RELATED APPLICATIONS

This application is a continuation of U.S. application Ser. No. 15/566,438 filed on Oct. 13, 2017, which application is the 35 U.S.C. § 371 national stage application of PCT Application No. PCT/US2016/027735, filed Apr. 15, 2016, where the PCT claims the benefit of and priority to U.S. Provisional Patent Application No. 62/147,763, filed on Apr. 15, 2015, entitled "ELECTROCHEMICAL SENSORS AND METHODS FOR USING ELECTROCHEMICAL SENSORS TO DETECT PLANT PATHOGEN INFECTION," each of which are herein incorporated by reference in their entireties.

FEDERAL SPONSORSHIP

This invention was made with Government support under Grant No. CBET-1159540 awarded by the National Science Foundation, Grant No. 045097-01 awarded by the American Chemical Society, and Grant No. 2015-67021-23188 awarded by the National Institute of Food and Agriculture. The Government has certain rights in this invention.

BACKGROUND

Agricultural losses due to plant pathogen infestations are estimated at $40 billion annually in the U.S. alone. Advanced disease detection and prevention in crops is a challenge for sustainable agriculture. Among the various types of pathogens that attack crops, fungi are the most common and most devastating for crops from Michigan to Florida in the east coast to California, Arizona and Mexico in the west. Pathogenic fungal infections cause numerous diseases such as white mold, grey mold, crown rot, leaf blight, fruit rot etc. in a variety of grain, fruit, and vegetable crops. For example, *Phytophthora capsici* alone is known to infect as many as 68 crops from 27 different families across the U.S.

The infections occur at multiple sites in crops (e.g., root, leaf, stem, fruit) during growth or after harvest, such as when produce is being stored or transported. If not controlled early, these infections spread quickly by wind, water, or physical contact between plants, causing devastating economic loss. The narrow profit margin greatly limits producers' options for effective controls for these diseases. Economic management of fruits may be challenging, as fruits are exposed to fungal inoculum for an extended period of time. Due to the lack of early-detection technology, fungicide application (even multiple applications) may come late and prove ineffective, resulting in almost 90% grower losses in some cases. Frequently these crops are sold through mass distribution well before the infections are known. Therefore, an early detection of pathogen infections could help growers contain the infection, spray only when needed, and minimize economical losses.

Currently used methods for disease detection in agricultural crops include direct methods, such as pathogen isolation and identification based on morphological characteristics, polymerase chain reaction (PCR), fluorescence in-situ hybridization (FISH), immunofluorescence (IF), enzyme-linked immuno-sorbent assay (ELISA), and gas chromatography mass spectrometry (GC-MS). There are also indirect methods, such as hyper spectral imaging, fluorescence, and other spectroscopy based techniques. These methods are time consuming, destructive, demand skilled analysts, require a laboratory set-up, and, unfortunately, do not offer either real-time monitoring or on-field deployment possibilities. Due to their destructive nature, direct methods can only be employed after the onset of disease symptoms to verify the infection, and thus do not allow for early monitoring and prevention. The indirect methods are expensive, do not possess high selectivity towards the infection/disease, and are primarily effective for post-harvest evaluation.

SUMMARY

The present disclosure provides electrochemical sensors for detecting target stress-induced plant volatile compounds and/or target pathogen-emitted volatile compounds, plant volatile detection systems, and methods for monitoring the condition of a plant or crop of plants.

Embodiments of electrochemical sensors include a volatile detection electrode. Embodiments of the volatile detection electrode include an electrode substrate and a bio-nanocomposite detection element on a surface of the electrode substrate and in electrochemical communication with the electrode substrate. In embodiments, the bio-nanocomposite detection element includes a nanomaterial transducer material and one or more enzymes capable of specific reaction with a target volatile compound or its hydrolysis product, wherein the target volatile compound is a stress-induced plant volatile compound or a target pathogen-emitted volatile compound. In embodiments, the enzyme is immobilized on the nanomaterial transducer material, reaction between the enzyme and the target volatile compound generates an electrical signal, and detection of the electrical signal indicates the presence of the target volatile compound. In embodiments, the volatile detection electrode includes a bi-enzyme or a tri-enzyme system, where at least one enzyme reacts with the target volatile compound producing a cascade of reactions involving the other enzymes of the system, where at least one of the reactions (e.g., the final reaction in the cascade) produces an electrical signal capable of being detected by the electrode.

Embodiments of a plant volatile detection system include: (a) a volatile collection reservoir adapted to collect volatile compounds emitted from a plant; (b) an electrochemical sensor according to the present disclosure; and (c) a signal processing mechanism in operative communication with one or more elements of the electrochemical sensor, the signal processing mechanism having data transfer and evaluation software protocols configured to transform raw data from the electrochemical sensor into diagnostic information regarding the presence or absence or levels of the plant volatile compound. In embodiments, an electrochemical sensor of the plant volatile detection system of the present disclosure includes an electrochemical cell including a volatile detection electrode, a counter electrode and a reference electrode, both the counter electrode and reference electrode in electrochemical communication with the volatile detection electrode, and a potentiostat to supply an electric current to the electrochemical cell and monitor changes in the electric current produced at the volatile detection electrode. The volatile detection electrode of the electrochemical cell is in fluid communication with the volatile collection reservoir of the system such that volatile compounds collected in the reservoir can be transferred to a detection surface of the volatile detection electrode. In embodiments, the volatile detection electrode has an electrode substrate and a bio-nanocomposite detection element on a detection surface of the electrode substrate and in electrochemical communication with the electrode substrate, the bio-nanocomposite detection element having a nanomaterial transducer material and one or more enzymes capable of specific reaction with a stress-induced plant volatile compound or its hydrolysis product, a plant-pathogen emitted volatile compound or its hydrolysis product, or both, wherein the enzyme is immobilized to the nanomaterial transducer material.

The present disclosure also provides methods for monitoring a condition of a plant or crop of plants using the electrochemical sensors and/or plant volatile detection systems of the present disclosure. In embodiments, such methods can include periodically sampling volatile emissions from the plant or one or more crop plants using a plant volatile detection system of the present disclosure and determining the presence of a plant disease associated with the one or more volatile compounds based on the information provided by a signal processing mechanism regarding the presence or absence or levels of the plant volatile compound.

BRIEF DESCRIPTION OF THE DRAWINGS

Further aspects of the present disclosure will be more readily appreciated upon review of the detailed description of its various embodiments, described below, when taken in conjunction with the accompanying drawings.

FIGS. 4A-4C are schematic illustrations of embodiments of a bi-enzyme modified electrode for detection of methyl salicylate (FIG. 4A), a mono-enzyme modified electrode for detection of ethyl guaiacol or ethyl phenol (FIG. 4B), and a mono-enzyme modified electrode for detection of octanone or octanol (FIG. 4C).

FIG. 5A illustrates an embodiment of an electrode modified with enzyme-nanoparticle composites, and FIG. 5B illustrates an embodiment of a process of enzyme immobilization to metal oxide nanoparticles (MOx NPs).

FIGS. 11A and 11B illustrate cyclic voltammetry (CV) responses of 3 mM methanol on bi-enzyme modified, AO modified and HRP modified electrodes (FIG. 11A) and 1.88 mM hydrolyzed methyl salicylate on bi-enzyme modified, AO modified, HRP modified and no enzyme modified electrodes (FIG. 11B).

FIGS. 15A and 15B illustrate interference of cis-3-hexenol, hexyl acetate, and cis-3-hexenyl acetate with phosphate buffer as control and interference percentage dependent on concentration of green leaf volatiles (insert) (FIG. 15A) and display of details from 500 second to 800 second (FIG. 15B).

FIG. 18 illustrates the ameprometric I-t curve of hydrolyzed wintergreen oil from 0, 0.1 to 1 mM on a bi-enzyme modified RDE.

FIG. 19A illustrates cyclic voltammetry responses of $SnO_2$—SP (a and a') and $TiO_2$—SP (b and b') with (a and b) and without (a' and b') the presence of 0.17 mM p-ethylguaiacol (FIG. 19A).

Figure 1:
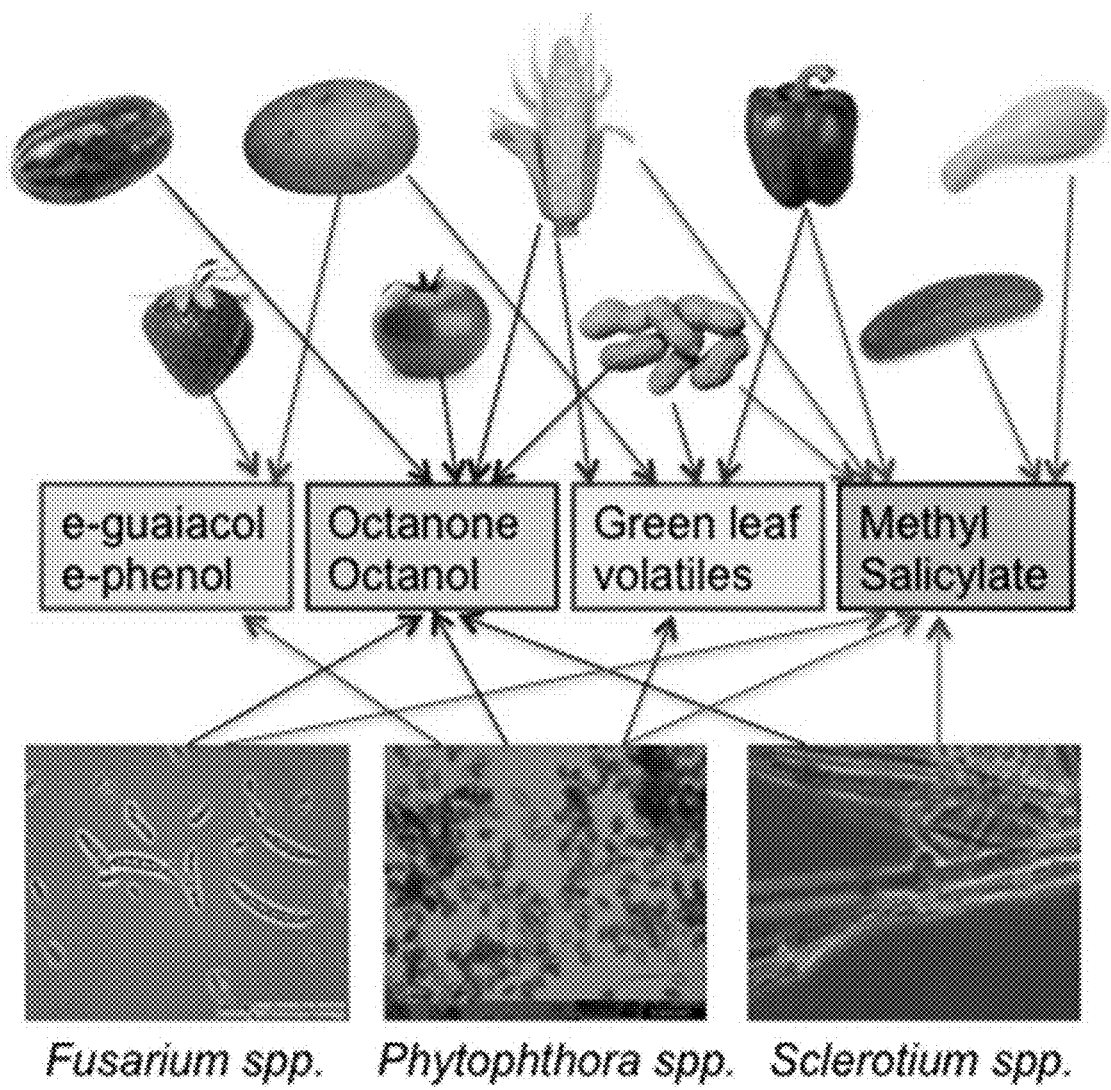
FIG. 1 illustrates a web showing the production of various volatile compounds by or as a result of infection of various fruits and vegetables by pathogens such as *Fusarium* spp., *Phytophthora* sp., and *Scelrotium* spp.

Methyl salicylate was hydrolyzed manually to generate salicylate and methanol (1). Salicylate, the main analyte was catalyzed by salicylate hydroxylase to generate catechol in presence of NADH and oxygen (2). Catechol is oxidized by tyrosinase to form 1,2-benzoquinone (3). The detection of methyl salicylate is finally realized by measuring the reduction of 1,2-benzoquinone to catechol on the electrode surface (4).

Figure 22:
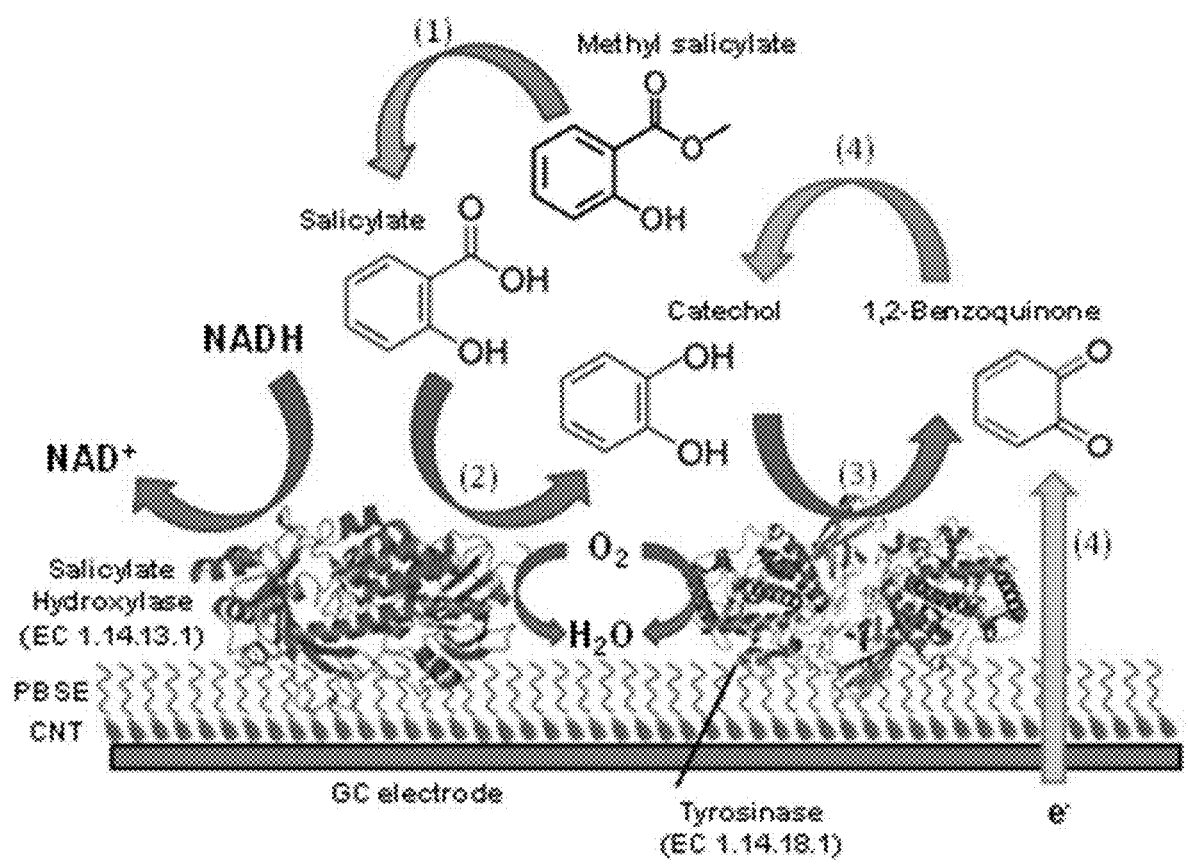
FIG. 22 is a schematic illustration of methyl salicylate detection on bi-enzyme (salicylate hydroxylase and tyrosinase) based carbon nanotube and PBSE modified biosensor.
Figure 23A:
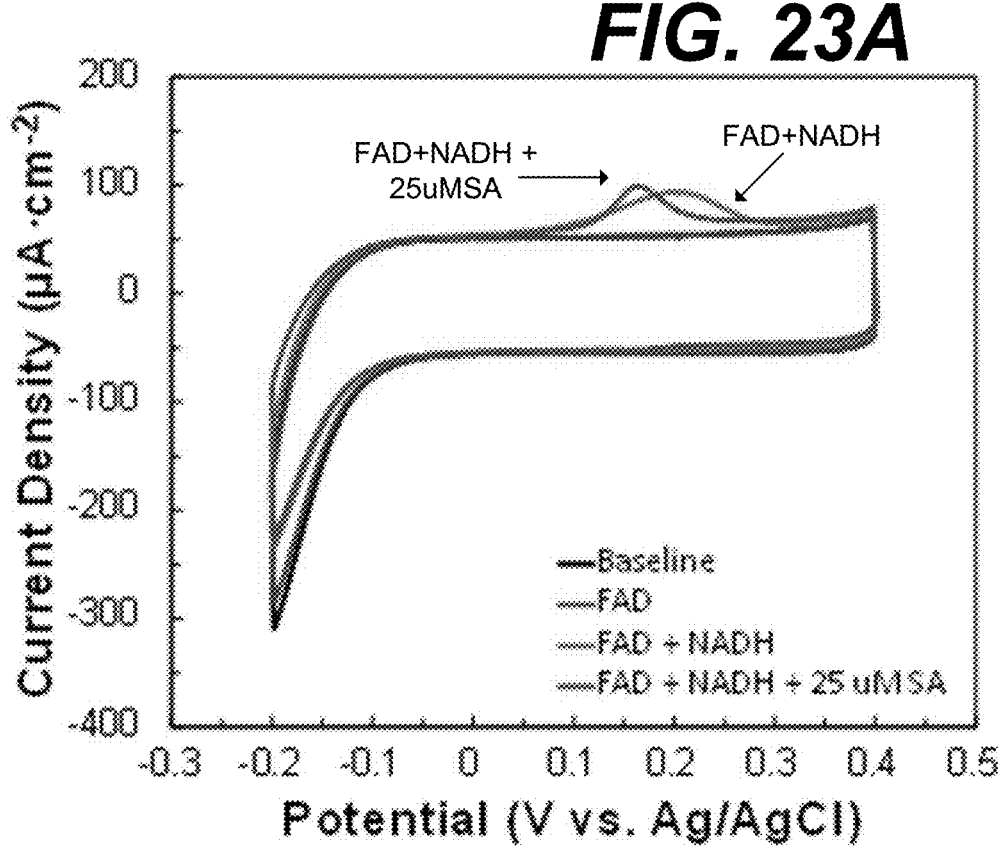
Figure 23B:
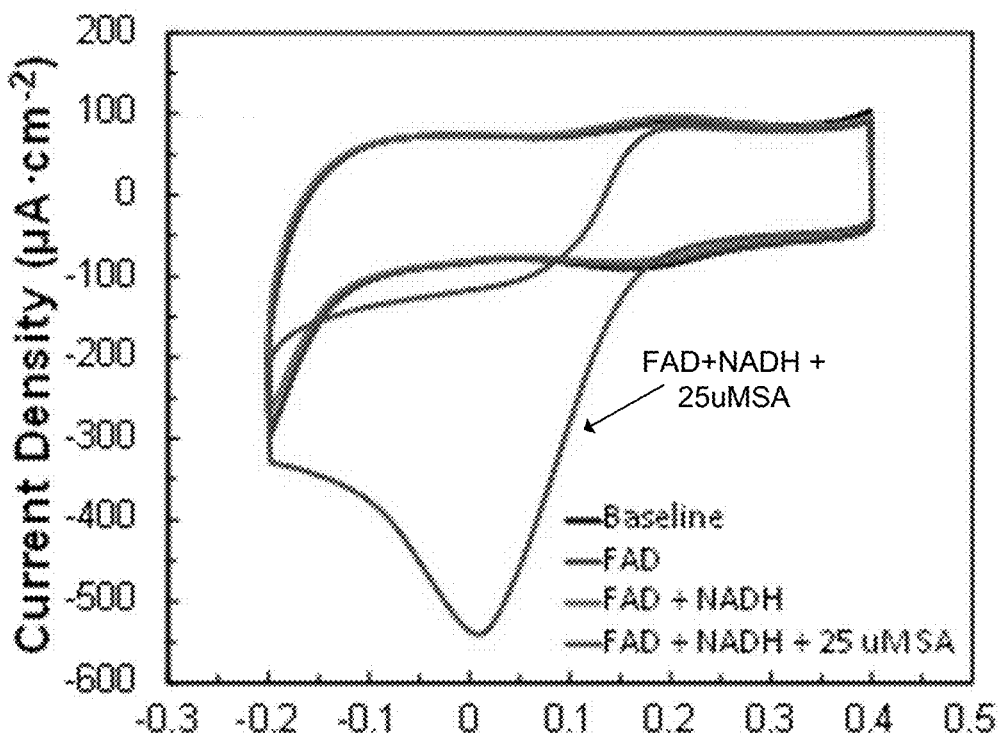

FIG. 23A illustrates cyclic voltammetry after sequential addition of 100 µL of 0.1 mM FAD, 50 µL of 10 mM NADH, and 25 µM salicylate, on salicylate hydroxylase immobilized mono-enzyme CNT electrode including SH. FIG. 23B illustrates cyclic voltammetry after the same additions carried out on bi-enzyme CNT electrode including SH and TYR. The reduction wave appearing below 0.15 V can be attributed to benzoquinone reduction described as step 4 in FIG. 22.

Figures 24A, 24B:
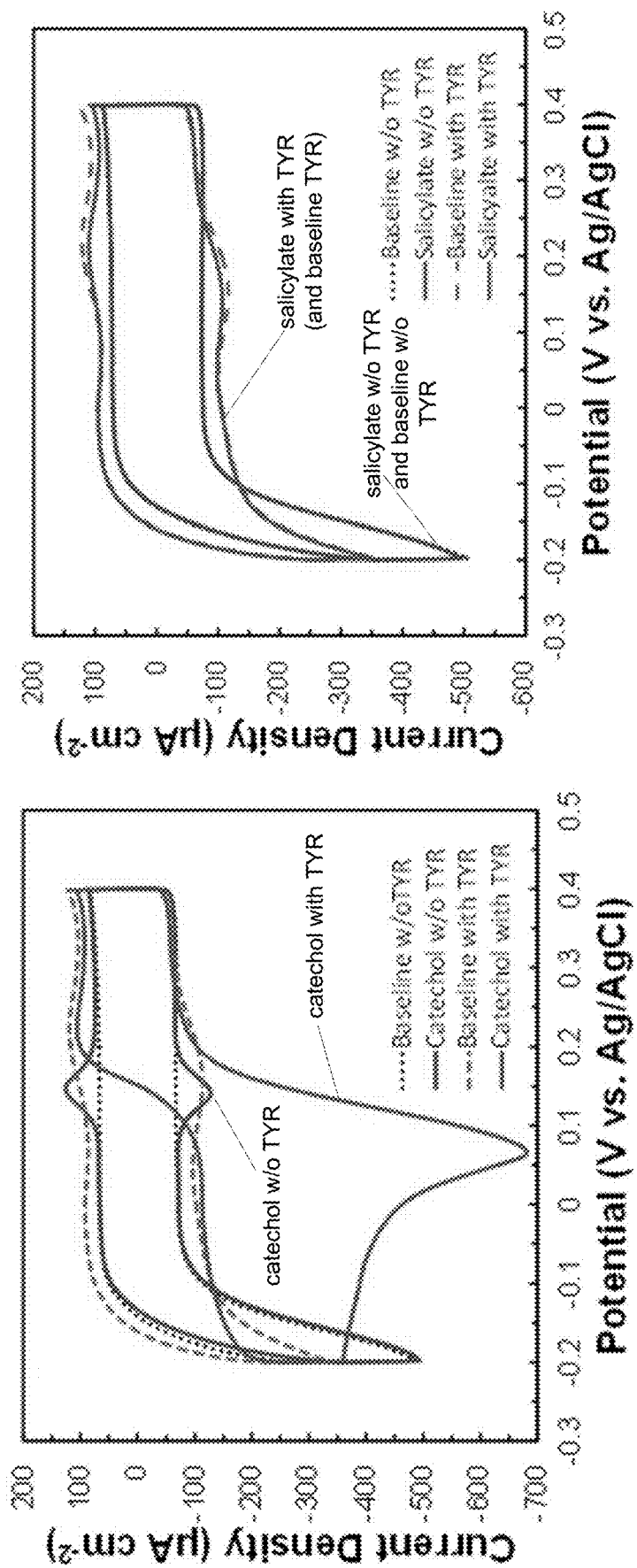

FIGS. 24A-24B illustrate cyclic voltammetry responses of unimmobilized and TYR-immobilized mono-enzyme CNT electrodes in the presence and absence of catechol (FIG. 24A) and salicylate (FIG. 24B) in the electrolyte.

Figure 25:
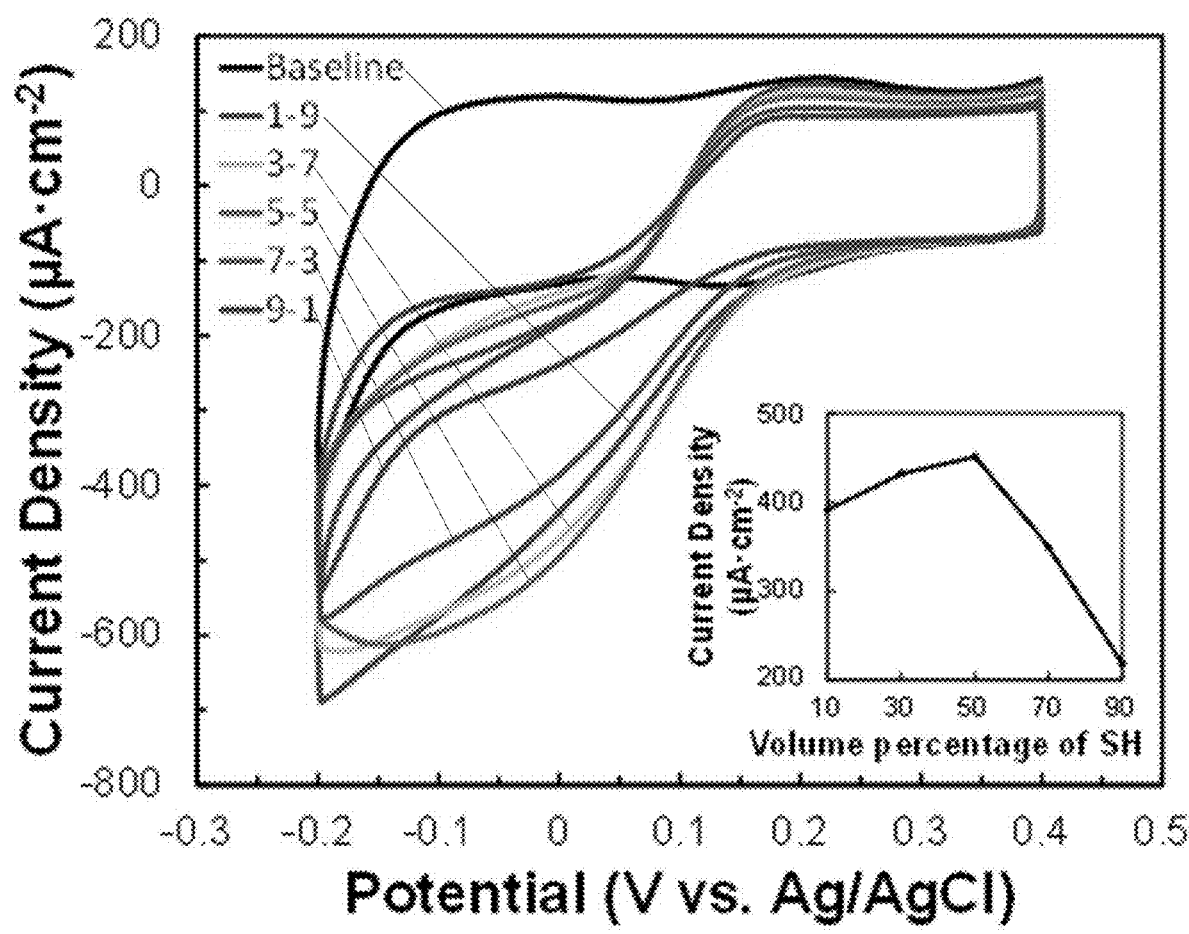

FIG. 25 illustrates cyclic voltammetry responses of the bi-enzyme biosensor containing immobilized salicylate hydroxylase and tyrosinase. The 2 mL electrolyte includes 25 µM salicylate with FAD (4.7 µM) and NADH (0.23 mM). The ratio of SH:TYR loadings by volume on the electrode respectively are 1:9, 3:7, 5:5, 7:3, and 9:1. Insert figure shows the current density of the sensor measured at 0.025 V for different enzyme loading ratios showing the maximum sensitivity was obtained when the enzyme volume ratio was 1:1.

Figure 26A:
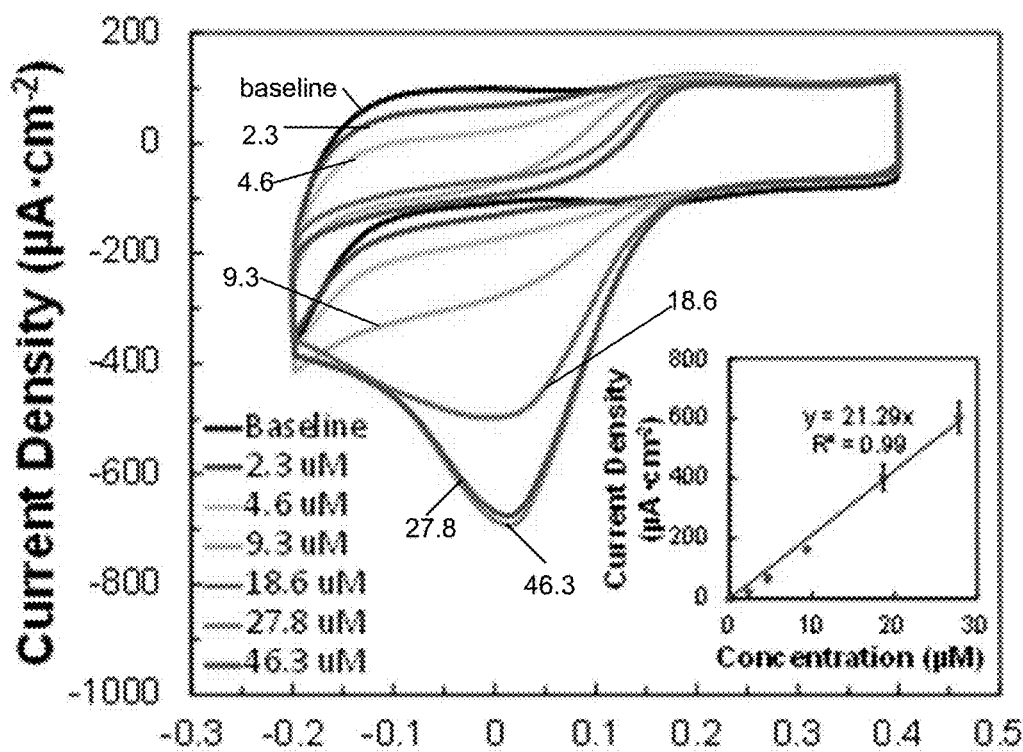
Figure 26B:
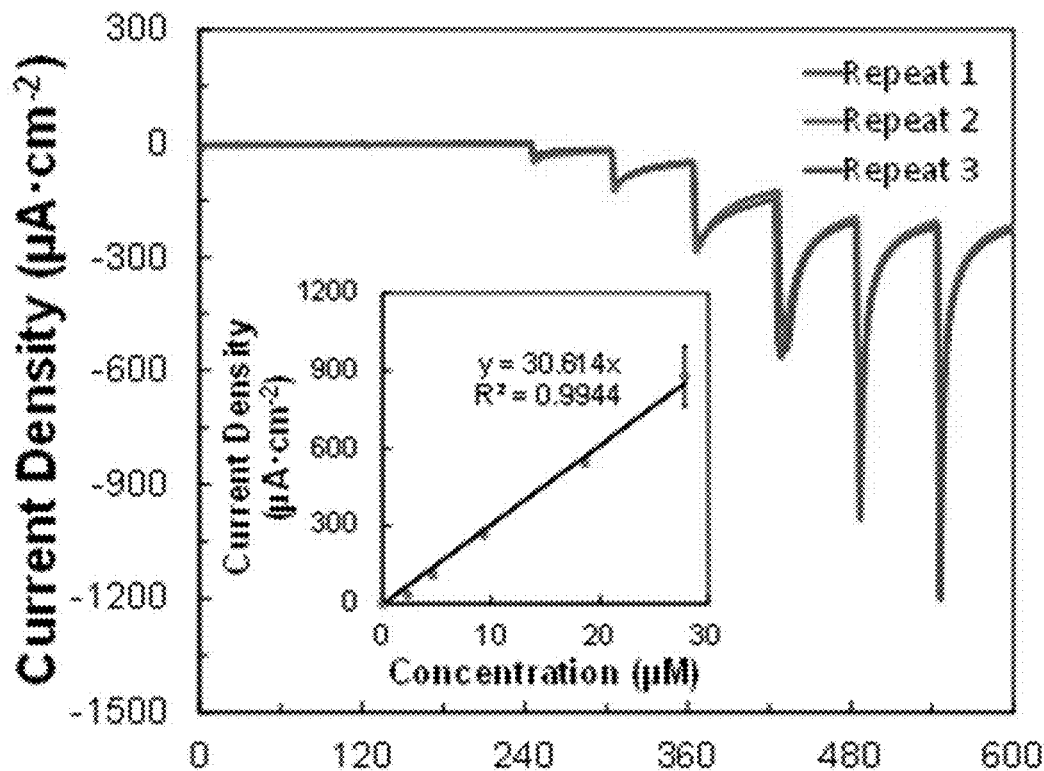

FIGS. 26A and 26B illustrate cyclic voltammetry (FIG. 26A) and constant potential amperometry (FIG. 26B) responses of salicylate with presence of FAD and NADH and sensitivity, linear range and $R^2$ value (Insert).

Figure 27A:
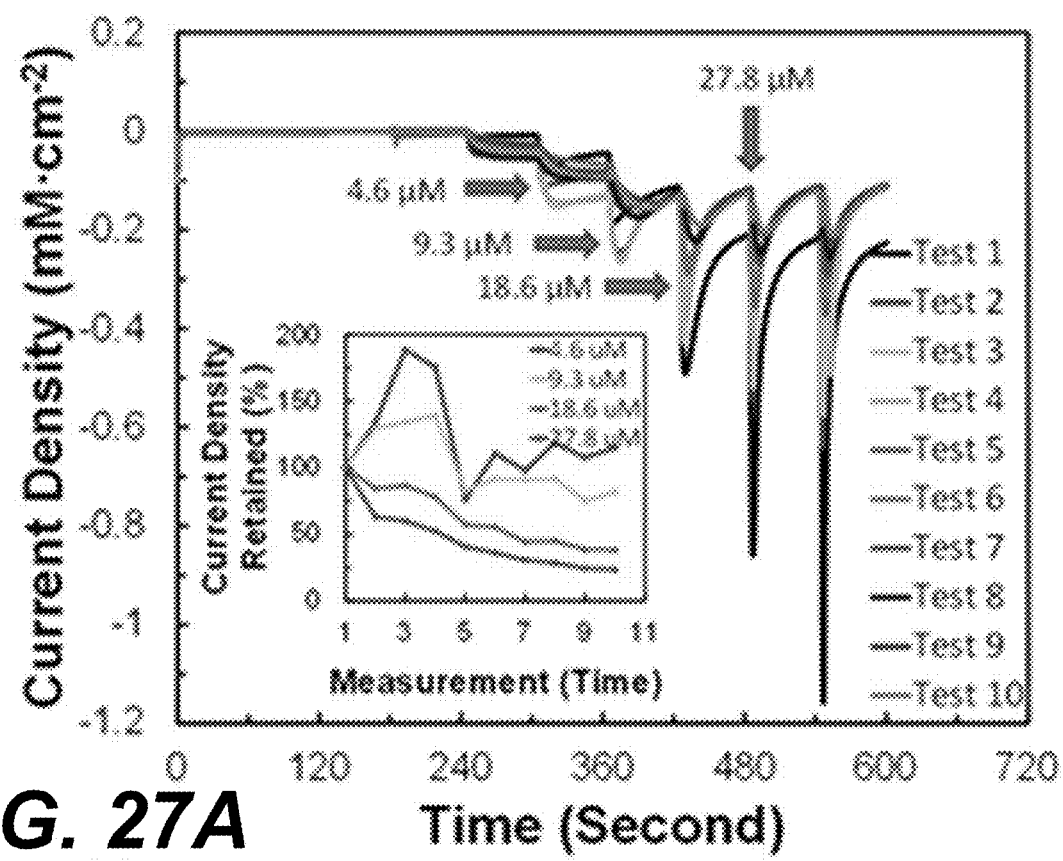
Figure 27B:
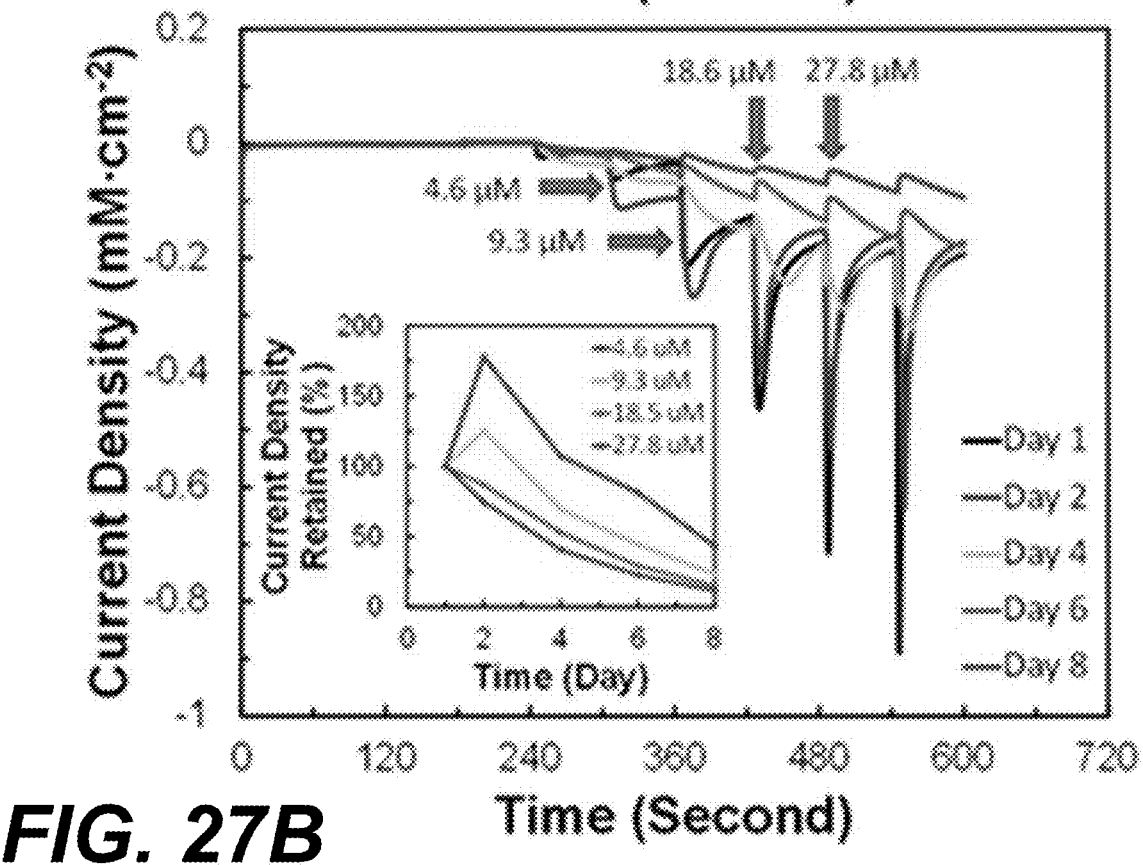

FIGS. 27A and 27B illustrate the reusability (27A) and stability (27B) of an embodiment of a bi-enzyme biosensor for salicylate from 2.3 µM to 46.3 µM (current plots are in reverse order: Test 1 is lowest line plot and Test 10 is the top line plot for FIG. 27A; Day 1 is lowest plot and Day 1 is top-most plot for FIG. 27B). Current density retention over measurements in reusability (FIG. 27A) and time in stability (FIG. 27B) are displayed in insets with two low concentrations (2.3 µM and 4.6 µM) and high concentrations (18.5 µM and 27.8 µM) (line plots in both inserts: top (4.6), middle-high: 9.3; middle-low: 18.5; bottom: 27.8)

Figure 28:
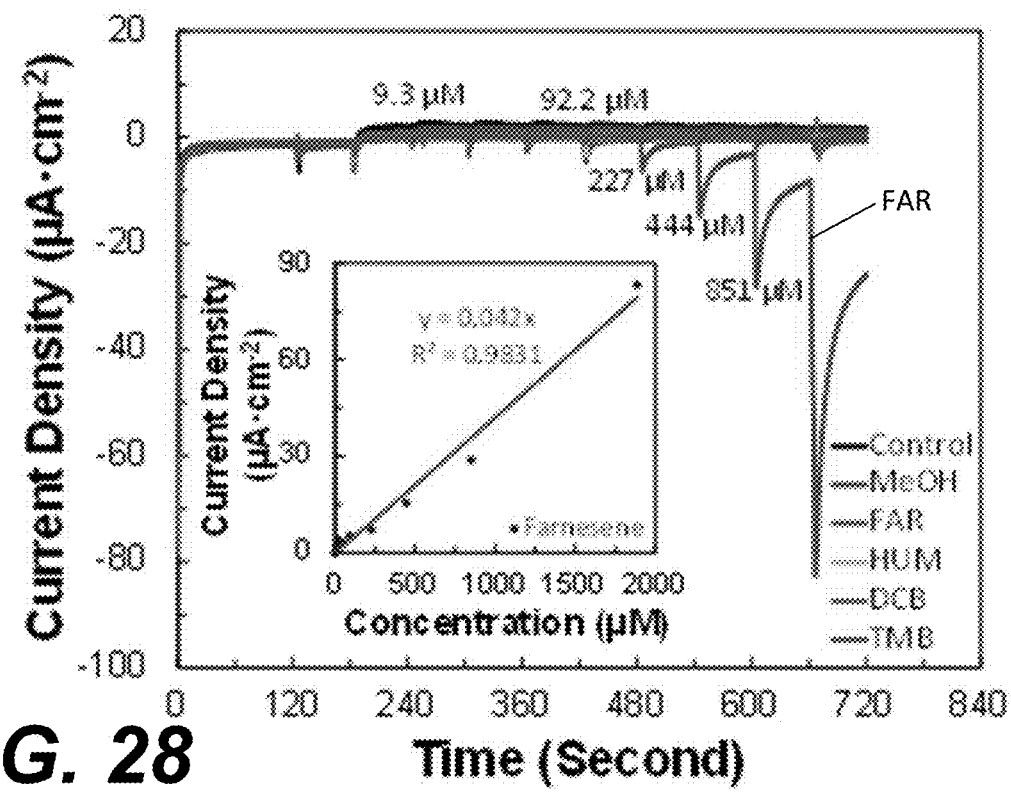

FIG. 28 illustrates constant potential amperometry responses of interference compounds: methanol (MeOH), farnesene (FAR), humulene (HUM), dichlorobenzene (DCB), 1,2,3-trichlorobenze (TCB) and that of the control (no interfering compound). The insert graph shows the linear increase in farnesene currents with its concentration with a sensitivity of 0.042 $\mu A \cdot cm^{-2} \cdot \mu M^{-1}$.

Figure 29:
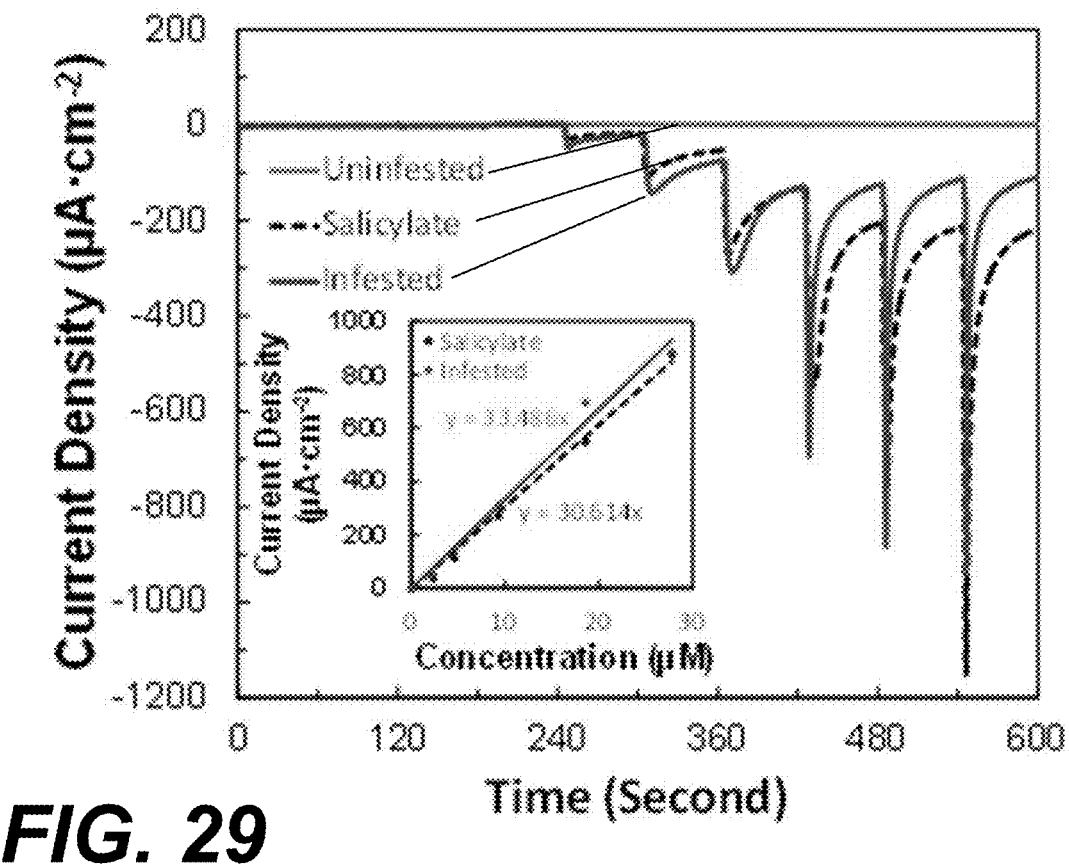

FIG. 29 illustrates constant potential amperometry responses of uninfested synthetic analyte and infested synthetic analyte in simulated sample study. The insert graph shows the sensitivity of the infected synthetic analyte and pure salicylate.

Figure 30:
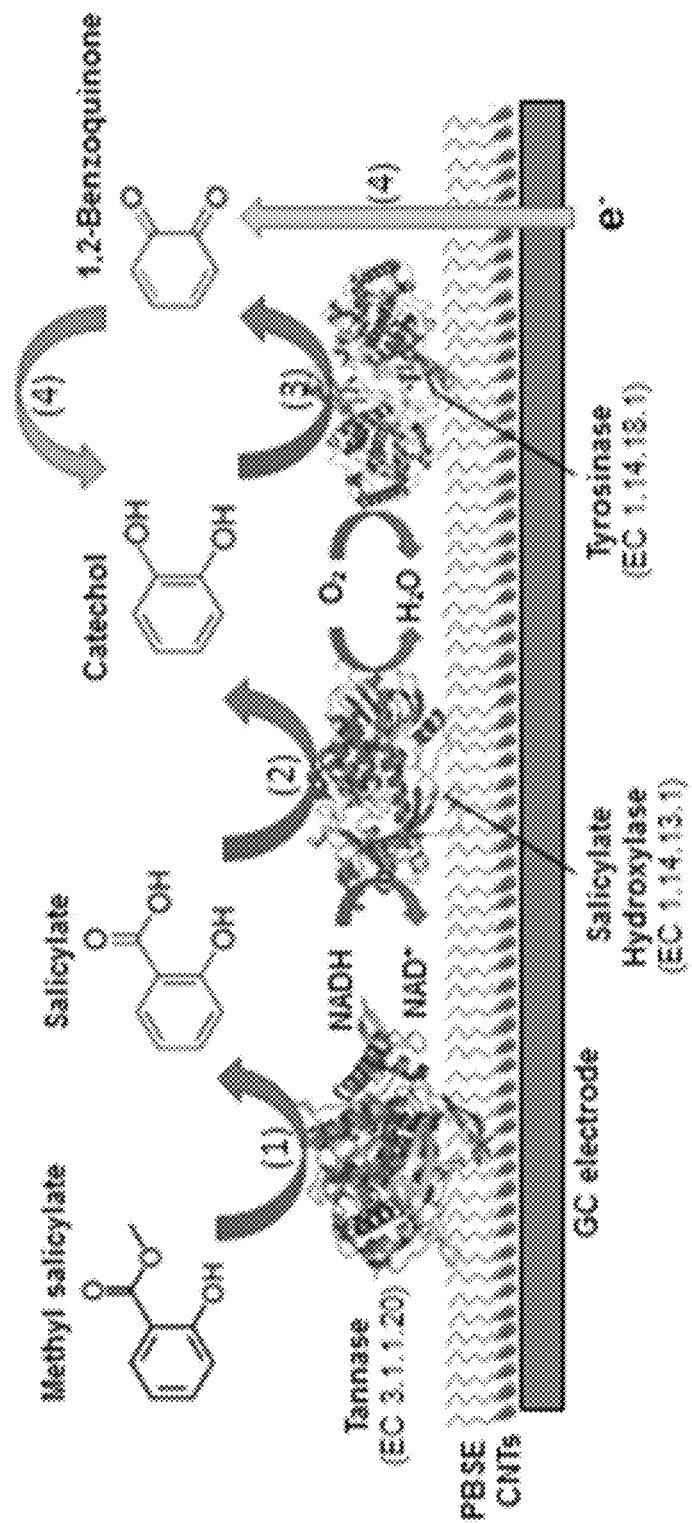

FIG. 30 is a schematic illustration of methyl salicylate detection on an embodiment of a tri-enzyme (tannase, salicylate hydroxylase and tyrosinase) based carbon nanotube and PBSE modified biosensor, where the immobilized enzyme tannase hydrolyses methyl salicylate to salicylate and methanol in step (1).

Figure 31:
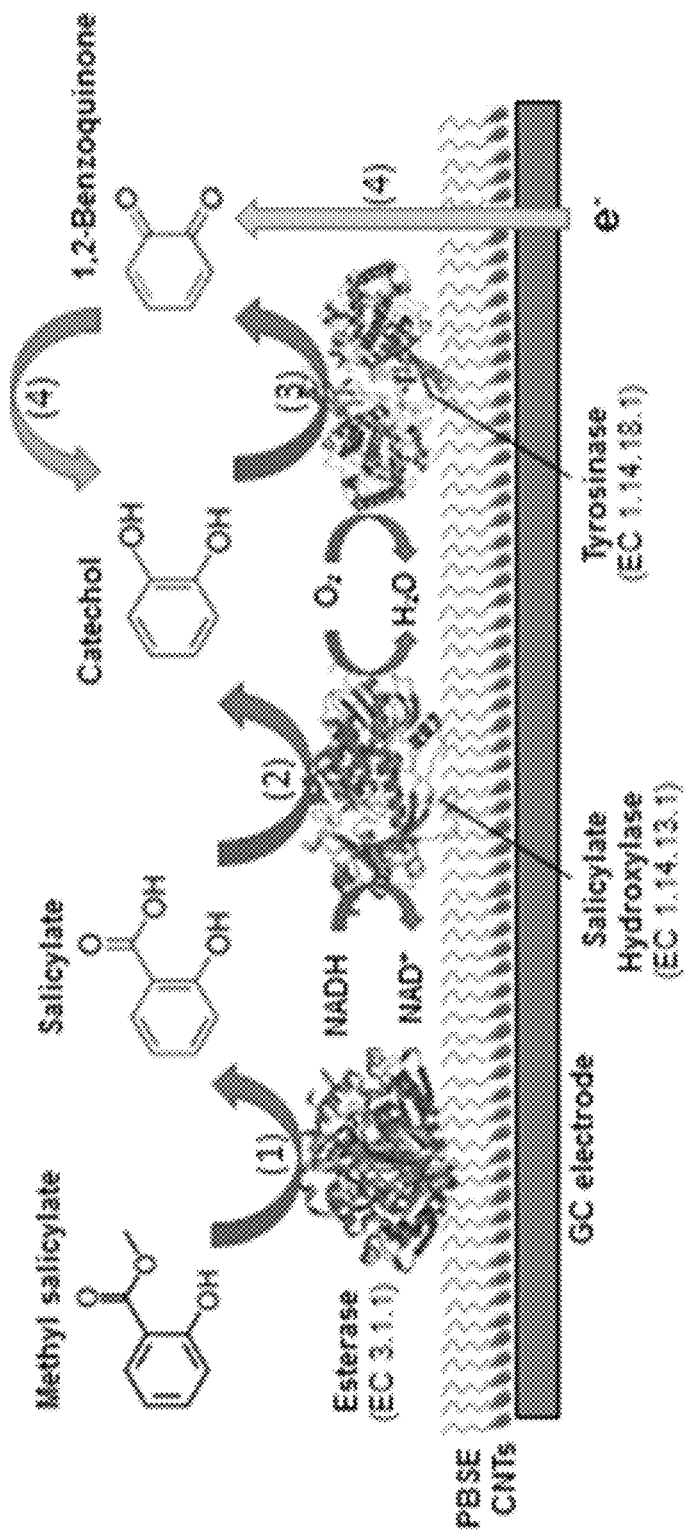

FIG. 31 is a schematic illustration of methyl salicylate detection on an embodiment of a tri-enzyme (esterase, salicylate hydroxylase and tyrosinase) based carbon nanotube and PBSE modified biosensor where the immobilized enzyme esterase hydrolyses methyl salicylate to salicylate and methanol in step (1).

FIGS. 32A-32D illustrate a series of cyclic voltammetry responses of methyl salicylate (FIGS. 32 A,B) and salicylate (FIGS. 32C,D) on salicylate hydroxylase (SH) and tyrosinase (TRY) immobilized bienzymatic biosensor (FIGS. 32A,C) and esterase (ES), SH and TYR immobilized trienzymatic biosensors (FIGS. 32 B,D).

Figure 33:
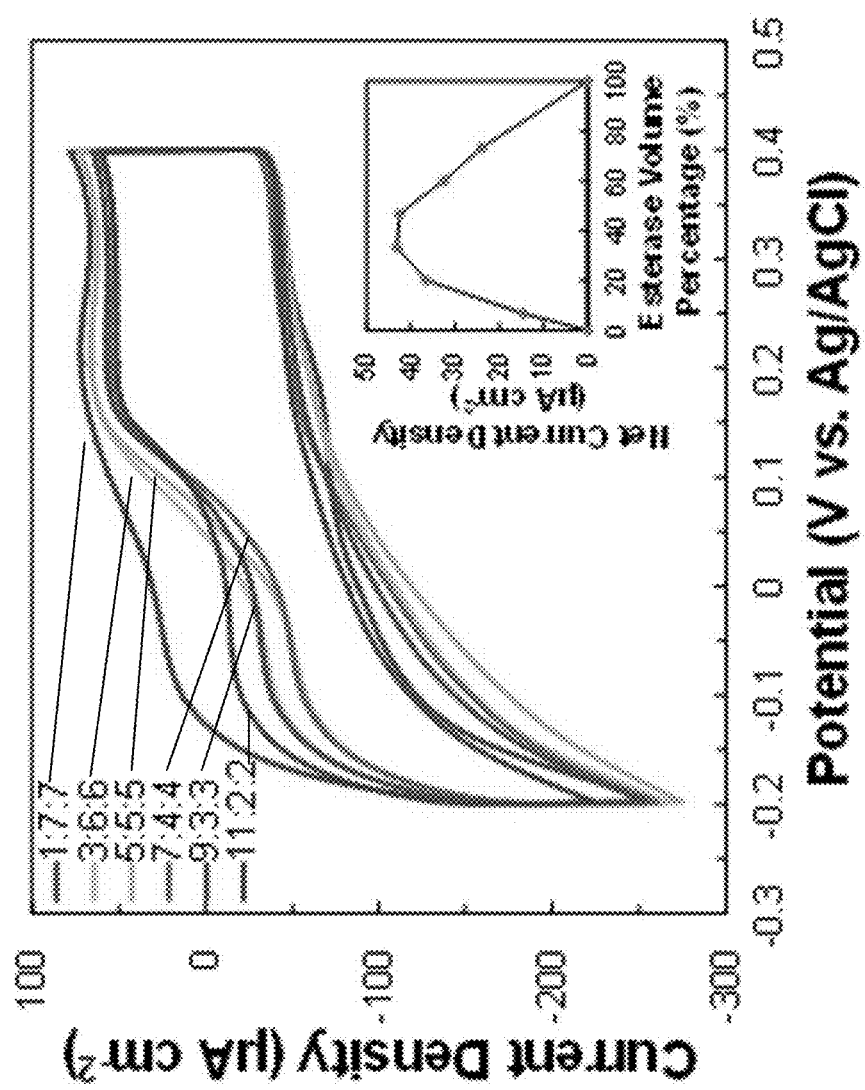

FIG. 33 illustrates cyclic voltammetry responses of 92 uM methyl salicylate on trienzymatic biosensor with different volume ratios of esterase (5 mg/mL), salicylate hydroxylase and tyrosinase (5 mg/mL) and the net current density against different esterase volume percentage (Insert).

Figure 34A:
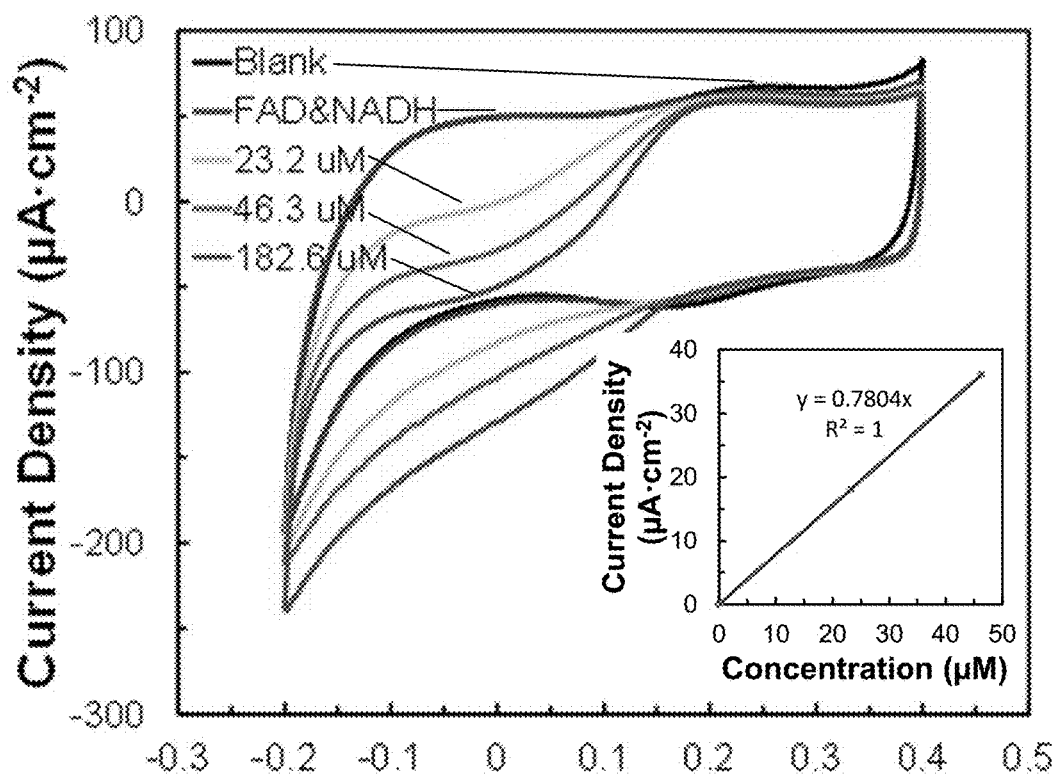
Figure 34B:
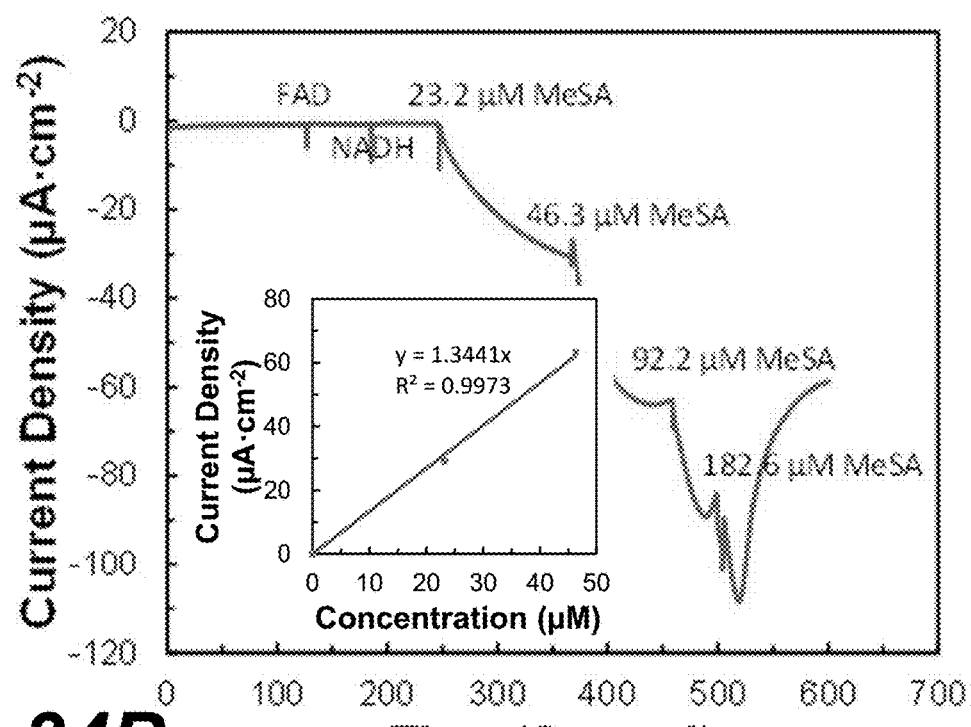

FIGS. 34A and 34B illustrate cyclic voltammetry (FIG. 34A) and constant potential amperometry (FIG. 34B) responses of a tri-enzymatic biosensor to different concentrations of methyl salicylate. Inserted graphs are current density versus concentration. Sensitivity is determined to be 0.78 $\mu A \cdot cm^{-2} \cdot \mu M$ and 1.34 $\mu A \cdot cm^{-2} \cdot \mu M$ by CV and CPA, respectively.

Figure 35:
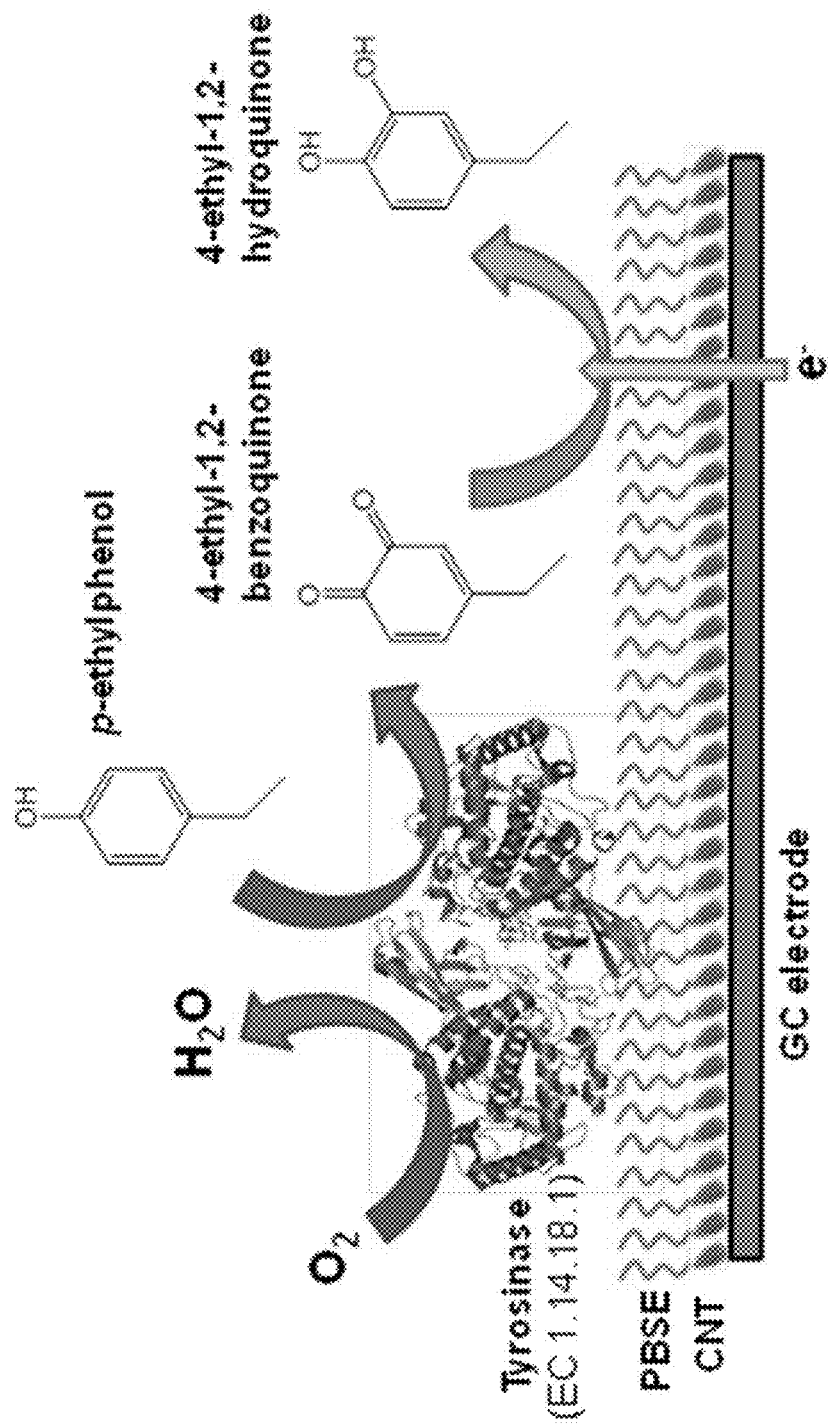

FIG. 35 is a schematic illustration of p-ethylphenol detection on an embodiment of a tyrosinase-immobilized biosensor. p-ethylphenol can be oxidized to 4-ethyl-1,2-benzoquinone by tyrosinase and the detection is based on the reduction of 4-ethyl-1,2-benzoquinone to 4-ethyl-1,2-hydroquinone.

Figure 36A:
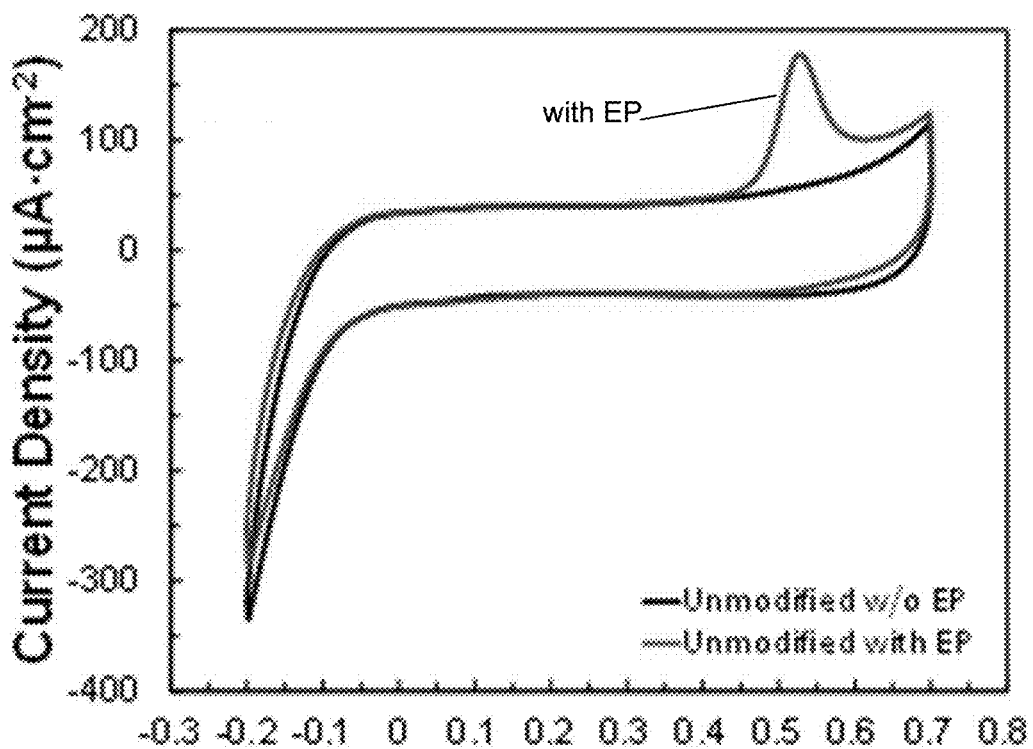
Figure 36B:
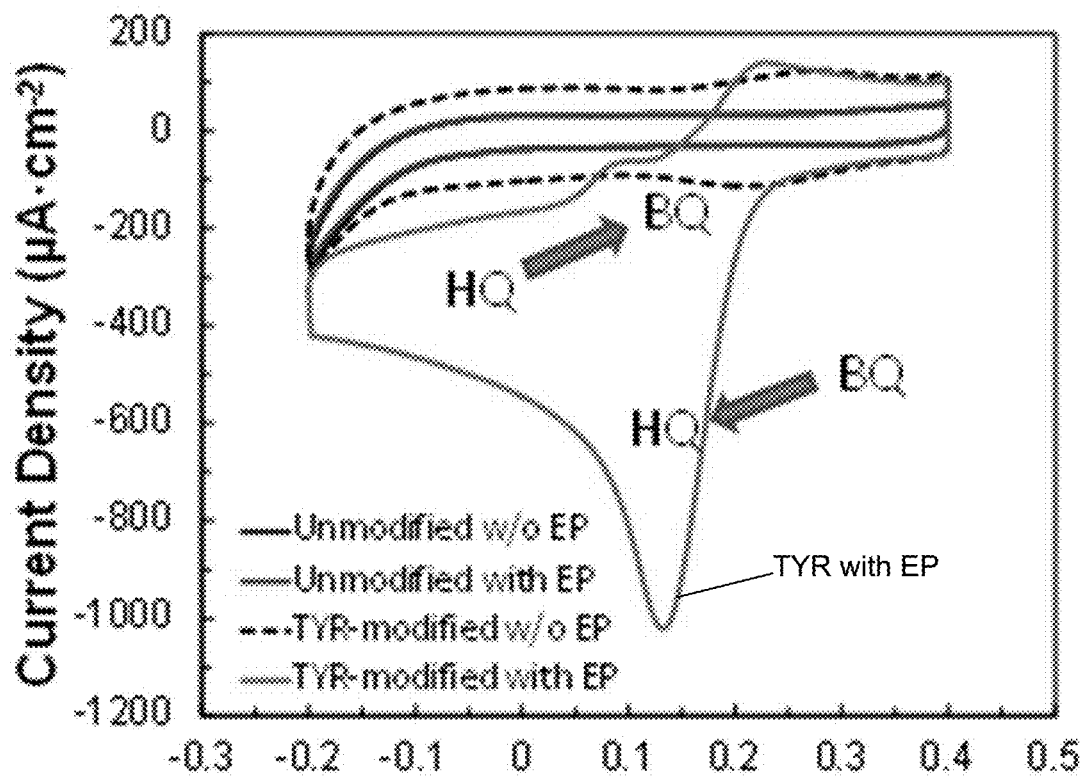

FIGS. 36A and 36B illustrate cyclic voltammetry responses of unmodified CNT electrode with and without p-ethylphenol (FIG. 36A) and TYR-modified electrode in the presence and absence of p-ethylphenol (FIG. 36B). BQ-4-ethyl-1,2-benzoquinone and HQ-4-ethyl-1,2-hydroquinone.

Figure 37A:
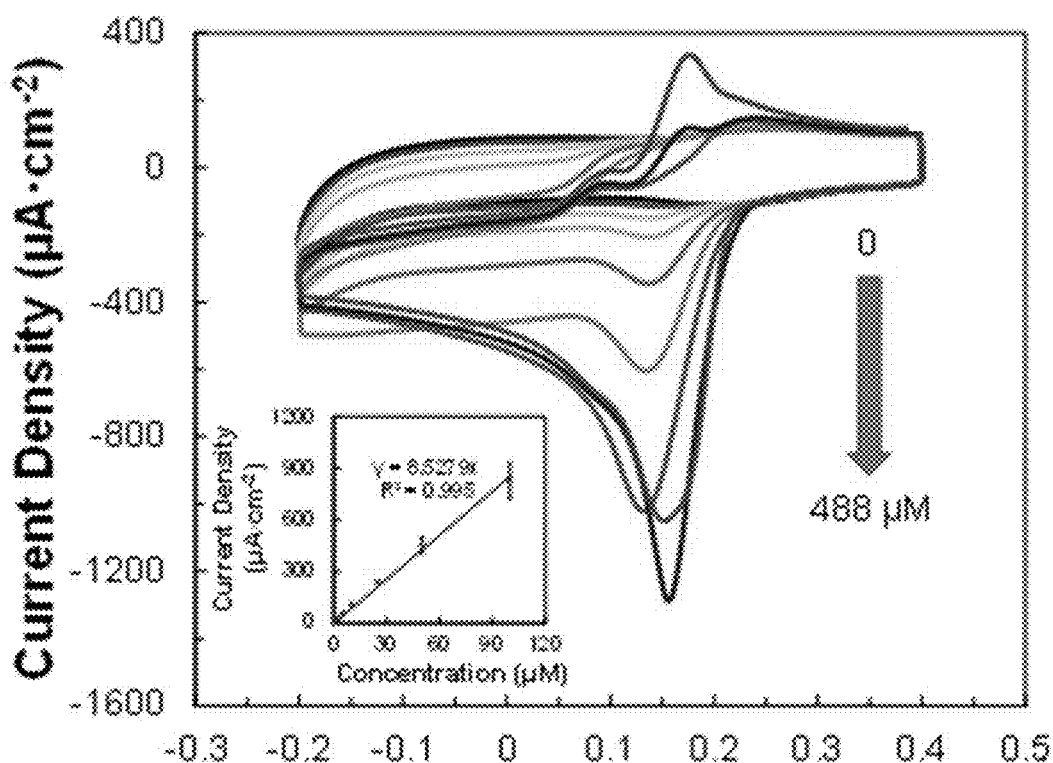
Figure 37B:
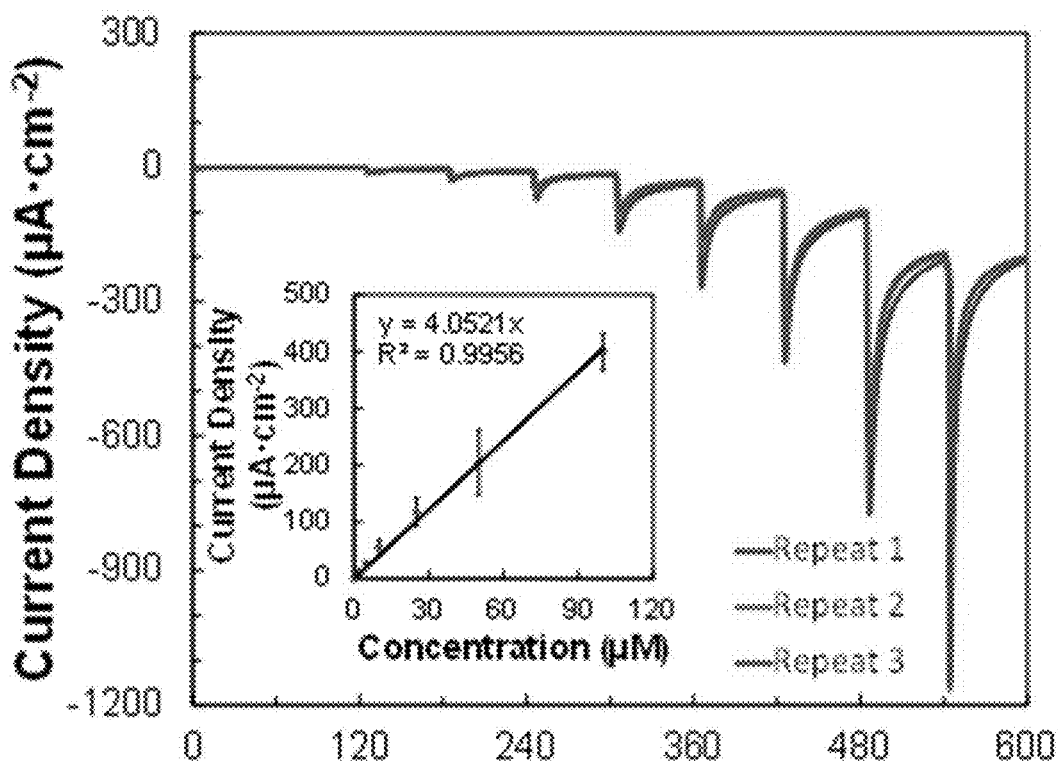

FIGS. 37A and 37B illustrate detection of p-ethylphenol with tyrosinase-modified biosensor using cyclic voltammetry (CV) (FIG. 37A), and constant potential amperometry at potential of 0.13 V (FIG. 37B). Insert graphs display linear range of reliable detection, sensitivity and $R^2$ value.

Figure 38:
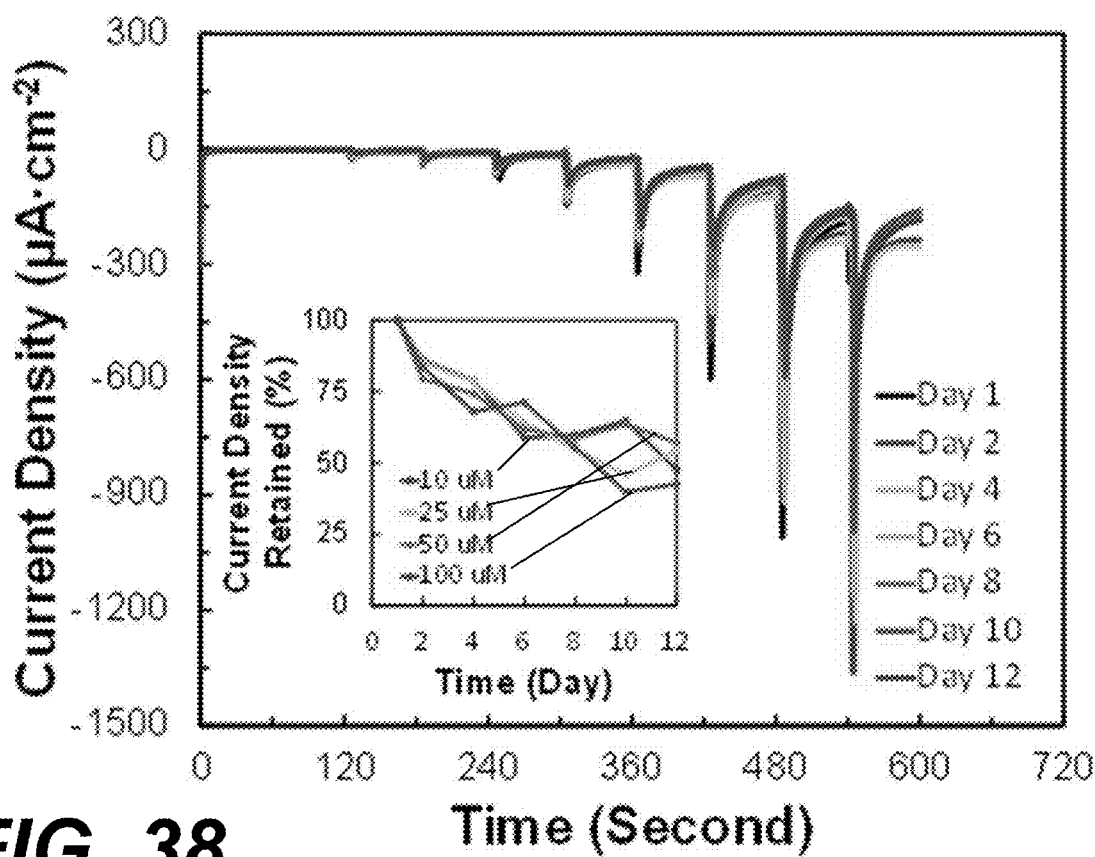

FIG. 38 illustrates the stability of p-ethylphenol detection in 10, 25, 50 and 100 µM p-ethylphenol solution on Day 1, 2, 4, 6, 8, 10 and 12. Percentage of current density retained is displayed (Insert).

Figure 39:
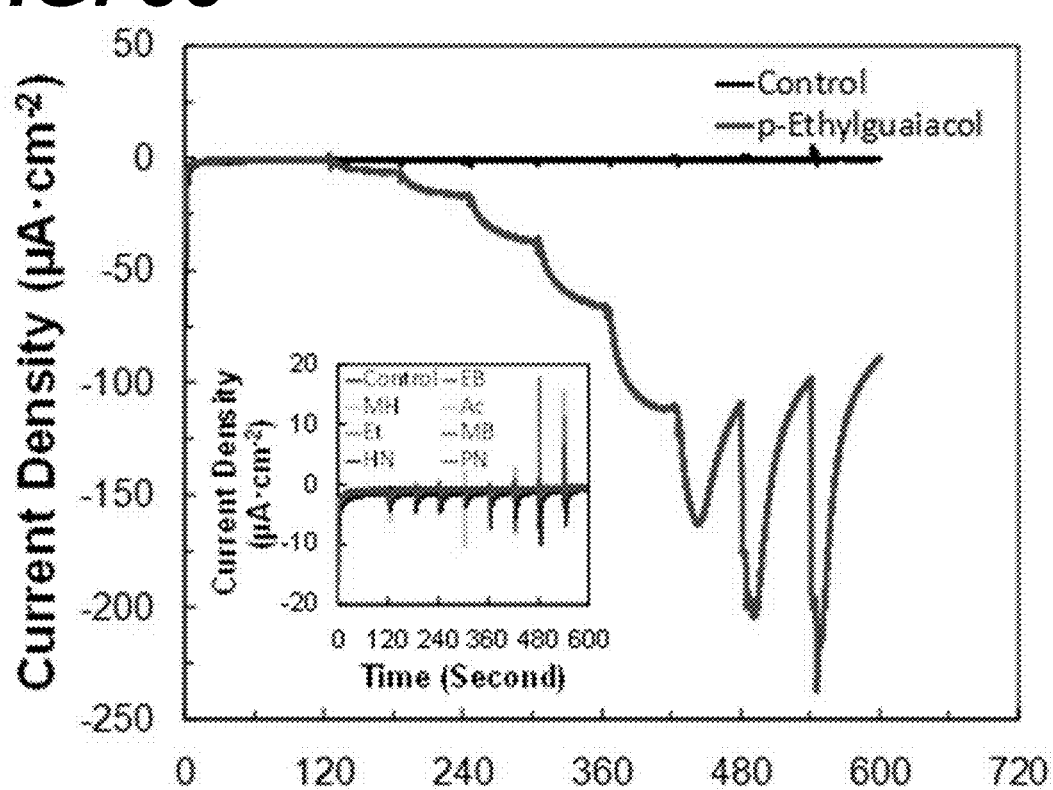

FIG. 39 illustrates constant potential amperometry of interference compound: ethyl butanoate (EB), methyl hexanoate (MH), acetone (Ac), ethanol (Et), methyl butanoate (MB), 2-heptanone (HN) and 2-pentanone (PN) (Insert) and p-ethylguaiacol and control.

Figure 40:
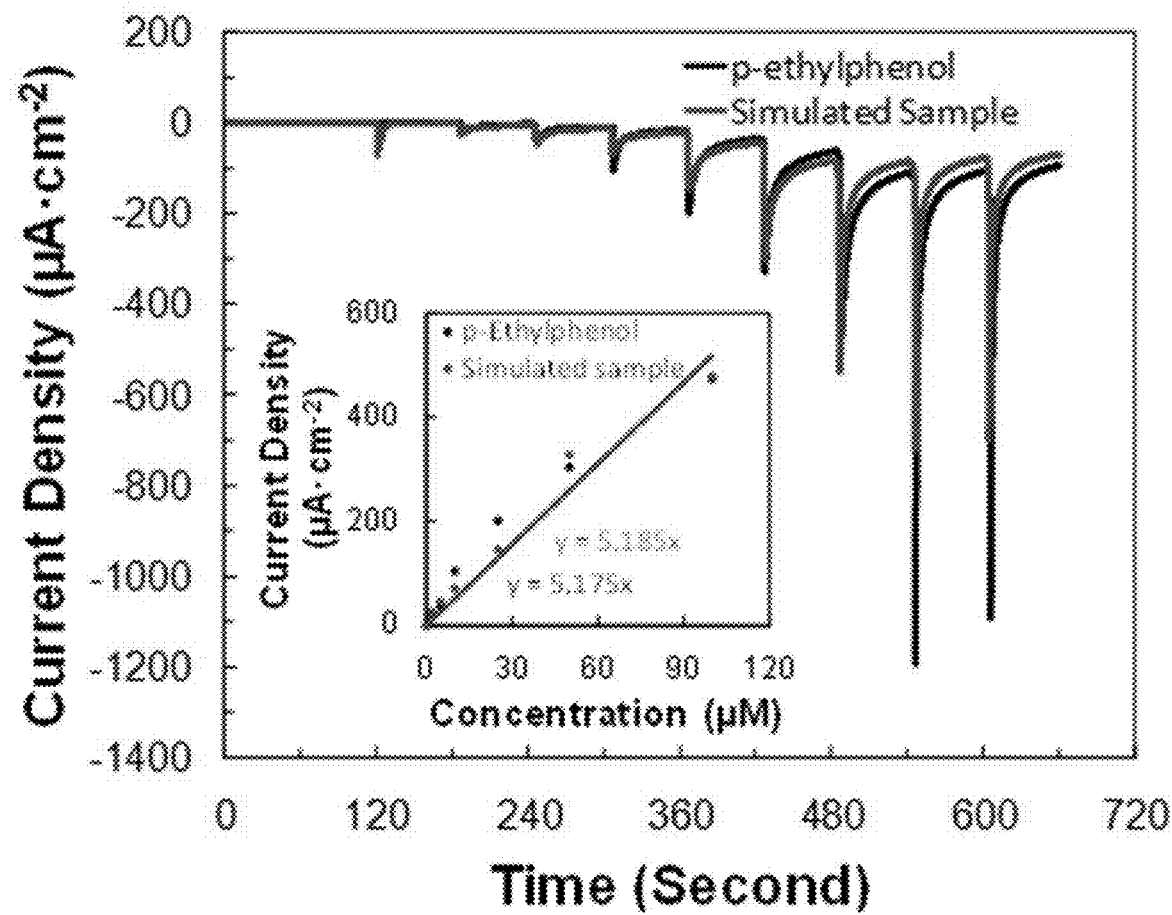

FIG. 40 illustrates Constant potential amperometry comparison of simulated sample and pure p-ethylphenol as control and sensitivity determination (Insert).

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification that are incorporated by reference, by notation in the application, are incorporated by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, organic chemistry, biochemistry, botany, electrochemistry, and the like, which are within the skill of the art. Such techniques are explained fully in the literature.

It must be noted that, as used in the specification and the appended embodiments, the singular forms "a," "an," and "the" include plural referents unless the context clearly dictates otherwise. Thus, for example, reference to "a support" includes a plurality of supports. In this specification and in the embodiments that follow, reference will be made to a number of terms that shall be defined to have the following meanings unless a contrary intention is apparent.

As used herein, the following terms have the meanings ascribed to them unless specified otherwise. In this disclosure, "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Definitions

In describing the disclosed subject matter, the following terminology will be used in accordance with the definitions set forth below.

As used herein, "about," "approximately," and the like, when used in connection with a numerical variable, generally refers to the value of the variable and to all values of the variable that are within the experimental error (e.g., within the 95% confidence interval for the mean) or within +/−10% of the indicated value, whichever is greater.

As used herein, "isolated" indicates removed or separated from the native environment. An isolated peptide or protein (e.g., an enzyme) indicates the protein is separated from its natural environment. Isolated peptides or proteins are not necessarily purified.

The term "polypeptides" and "protein" include proteins, such as enzymes, and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

Modifications and changes can be made in the structure of the polypeptides of this disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

As used herein "functional variant" refers to a variant of a protein or polypeptide (e.g., a variant of a plant enzyme) that can perform the same functions or activities as the original protein or polypeptide, although not necessarily at the same level (e.g., the variant may have enhanced, reduced or changed functionality, so long as it retains the basic function).

"Identity," as known in the art, is a relationship between two or more polypeptide sequences, as determined by comparing the sequences. In the art, "identity" also refers to the degree of sequence relatedness between polypeptides as determined by the match between strings of such sequences. "Identity" and "similarity" can be readily calculated by known methods, including, but not limited to, those described in Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

The terms "native," "wild type", or "unmodified" in reference to an organism (e.g., plant or cell), polypeptide, protein or enzyme, are used herein to provide a reference point for a variant/mutant of an organism, polypeptide, protein, or enzyme prior to its mutation and/or modification (whether the mutation and/or modification occurred naturally or by human design). Typically, the unmodified, native, or wild type organism, polypeptide, protein, or enzyme has an amino acid sequence that corresponds substantially or completely to the amino acid sequence of the polypeptide, protein, or enzyme as it generally occurs naturally.

As used in the present disclosure, two materials are in "electrochemical communication" when electrons generated by a chemical reaction of one material (e.g., chemical reaction of a plant volatile compound with an enzyme) can be transferred to and/or accepted by the other material (e.g., another enzyme complex, a transducer material, and/or an electrode) or vice versa.

As used in the present disclosure, a "transducer" describes a material capable of acting as an electronic transducer to transfer/deliver electrons from one material/reaction to another. For instance, in embodiments of the electrochemical sensors of the present disclosure, a sensor may include a transducer (e.g., a nanomaterial transducer) that is in electrical communication between an enzyme active site and the electrode. In embodiments, the electrode is formed from and/or functionalized with a transducer material and/or enzymes may be directly or indirectly associated with the transducer material (e.g., by immobilization on the nanomaterial transducer).

The term "bio-nanocomposite" refers to a material including both biologically derived material (e.g., proteins, enzymes, cells, other biological compounds) as well as a nanomaterial. In embodiments, a bio-nanocomposite includes a nanomaterial such as metal or metal-oxide nanoparticles, carbon based nanoparticles (e.g., carbon nanotubes), or polymeric materials, and a biological material, such as a protein (e.g., an enzyme). In embodiments of a bio-nanocomposite of the present disclosure, the nanomaterial is a nanomaterial transducer material, and the biological material is an enzyme that is directly or indirectly associated with and/or immobilized to and in electrical communication with the nanomaterial transducer material to form the bio-nanocomposite.

The term "detectable" refers to the ability to perceive or distinguish a signal over a background signal. "Detecting" refers to the act of determining the presence of and recognizing a target or the occurrence of an event by perceiving a signal that indicates the presence of a target or occurrence of an event, where the signal is capable of being perceived over a background signal.

Discussion

Embodiments of the present disclosure encompass methods and systems for electrochemically sensing plant pathogen infection. Embodiments include electrochemical sensors capable of detecting plant volatiles and/or plant pathogen volatiles associated with plant pathogen infection, systems including the sensors, and methods of using the sensors to detect pathogen infection in plants, crops, or harvested plants and/or plant parts.

Plants and plant parts (leaf, stem, fruit, etc.) release unique chemicals when they experience stress during a pest or pathogen attack (also referred to herein as "stress-induced plant volatile compound(s)"). In some cases, the attacking pathogens also emit some characteristic chemicals indicative of infection (also referred to herein as "pathogen-emitted volatile compound(s)"). Detecting these characteristic plant and/or pathogen chemicals at ultra low levels can be used as a reliable way to detect pathogenic diseases and biotic/abiotic stresses in crops. A reliable, easy-to-use sensing technology for detecting pathogen infections through chemical profiling at early stages of disease will alert the farmers to take preventive and control measures to contain the infection and avoid massive crop damage.

The sensors, systems, and methods of the present disclosure include novel bio-nanocomposite based electrochemical sensing technology for highly selective and sensitive detection of chemicals resulting from pathogen infection of plants, such as, but not limited to, those in agricultural crops. Enzyme enhanced electrochemical sensing technology offers many advantages, such as, accuracy, specificity, rapid detection, non-invasiveness, field applicability, portability, robustness, selectivity, and ultra-low detection limits. The sensors of the present disclosure offer many advantages over conventionally used methods for disease detection in the agricultural industry, which require molecular biology methods and expensive spectroscopy methods that can only be used to confirm the disease but cannot be used for early identification. In the bio-nanocomposite based electrochemical sensors of the present disclosure, the high sensitivity of the nanostructured materials combined with high selectivity of enzymes will allow detection of the target volatile compounds in ultra-low quantities with minimal interference from other volatile compounds. This can be achieved using enzyme-functionalized nanomaterial composites as detection elements for amperometric transduction in electrochemical sensors. This approach has thus far not been applied in the field of agricultural sensor development.

Plants and pathogenic fungi release a complex mixture of volatile organic compounds (VOCs), including, but not limited to, green leaf volatiles, flavor active alcohols, terpenes and other aromatic metabolites. Since the chemical signature of the volatile mixture is often unique to the type of crop or pathogen, detecting these volatiles at low levels can be used as a reliable method for detecting pathogenic diseases and biotic/abiotic stresses in crops. The present disclosure provides reliable, easy-to-use sensing technology for detecting pathogen infections through volatile profiling at early stages of disease, which will allow time for implementation of preventive and control measures. Embodiments of the present disclosure also provide a portable sensor system (e.g., a 'briefcase-biosensor') to serve as a handy tool for individual farmers to monitor their crops throughout the growth period. The provision of a portable system for real-time monitoring of crop conditions and early detection of pathogen infection will increase agricultural productivity. Embodiments of the present disclosure also include a mobile smartphone application to correlate results of the biosensor testing (e.g., a specific plant or crop volatile emission profile) with standard parameters for target volatile levels that associates types of pathogen infections with ranges of volatile types and VOC levels. The sensors and systems of the present disclosure allow farmers to evaluate their crop health independently without relying on outside experts and to initiate measures for early intervention of detected infections. This will facilitate development of disease management strategies that reduce fungicide use, improve fungicide effectiveness, minimize agricultural losses and environmental pollution, and save millions of dollars in lost productivity while improving product quality.

As discussed above, most fungal pathogens release unique volatile signatures upon attacking the host. In response, the plants and/or fruits also emit characteristic chemical signatures as a phytochemical defense. For example, *Phytophthora* sp. (a common oomycete) infection results in the release of octanone, ethyl phenol and ethyl guaiacol by the fungus itself, and the release of methyl salicylate by the infected crop. Detection of the pathogen volatiles would indicate the existence of fungal growth, and detection of the plant volatiles would indicate the existence of plant stress. However, detection of both at the same time could help relate the plant stress to the pathogen infection, which can deterministically confirm the onset of the disease. Therefore, in some embodiments, the electrochemical sensor of the present disclosure is capable of simultaneous detection of both the pathogen's activity and the host's response to the infection, which can result in highly selective detection of the disease at very early stages of infection.

As mentioned earlier, the VOCs released during an infection could come from both the pathogen and the plant parts (in response to the infection). Plant tissues infected by various pathogens are known to produce characteristic volatiles, stress-induced plant volatiles that can be used to differentiate infected and healthy plants. The compounds are widely diverse and produced through various biosynthetic pathways including the octadecanoid pathway leading to fatty-acid derived green leaf volatiles (GLVs), monoterpenes, diterpenes, sesquiterpenes, isothiocyanates and diverse groups of aromatic metabolites. Other classes of compounds also include benzene derivatives, indole derivatives, heterocyclic organic compounds, long chain aliphatic hydrocarbons, aliphatic ketones, carboxylic acids, aldehydes and alcohols. For instance, as illustrated in FIG. 1, VOCs such as methyl salicylate, octan-one/-ol, ethyl phenol, ethyl guaiacol and green leaf volatiles are characteristic of the chemical signature in nearly a dozen crops upon infection by *Fusarium* spp, *Phytophthora* spp, and *Sclerotium* spp. While some are released from the infected fruits, others are released from the stem and leaves. For example, strawberries infected with *Phytophthora cactorum* were found to release 4-ethyl phenol and 4-ethyl guaiacol. Methyl salicylate and methyl jasmonate are often found to be common and distinct odors of infected plants. Plants release high levels of methyl salicylate especially during pathogen or pest infestations through the Shikimate biosynthesis pathway. In controlled laboratory tests, significant levels of methyl salicylate were released by pepper plants when infected by *Phytophthora capsici*. Studies show that unhealthy soy pods also release methyl salicylate. Moreover, unlike GLVs, methyl salicylate is an allelochemical and is released not only at the infection site, but throughout the plant through a systematic response. Octanone and/or octanol are found in VOCs collected from the site of most fungal infections. GLVs such as hexenol, hexenal, hexyl acetate, hexenyl acetate, and terpenes are also released in excess, indicative of a stressed plant.

Basic electrochemical detection of some common GLVs such as cis-3-hexenol, hexyl acetate and hexenyl acetate was achieved using amperometric methods as described in Umasankar, Y., et al., Analyst 2012, which is incorporated by reference herein. Detection limits as low as 28 nM (~0.5 ppb), a value 138 times lower than the human odor threshold limit (OTL) of 3.89 µM, were achieved; however, bio-recognition elements (e.g., an enzyme specific for the target volatile compound) was not used for specific detection.

Amperometric detection of methyl salicylate and ethyl guaiacol was performed using gold and metal oxide nanoparticles as both detection elements and transducers on electrodes as described in Umasankar, Y. & Ramasamy, R. P., Analyst 2013 and Costello, et al., Sensors and Actuators B 1999, which are incorporated herein by reference. In the first study, the use of gold nanoparticle (AuNP) modified electrode for methyl salicylate detection resulted in a sensitivity increase by ~35 fold and widened range of detection over unmodified carbon electrodes. In a second study, described in more detail in Example 2, below, metal oxide nanoparticles such as $TiO_2$ and $SnO_2$ were used to functionalize an electrode for detection of ethyl guaiacol, which is a typical VOC of infected berries and grapes. Both metal oxides exhibited fairly good sensitivity towards ethyl guaiacol of ~0.23 mA/mM·cm$^2$ and ultra-low detection limits around 60 nM (~1.1 ppb), 46 fold lower than OTL of 2.78 µM, but specific recognition elements (e.g., enzymes) were not provided for specificity.

While these nanomaterial-modified electrodes provide high surface area for enhanced sensitivity, they do not offer high selectivity (i.e., specificity) towards the target compound for detection. Since multiple volatile compounds can contribute to the electrochemical signals in the same potential window, it would be challenging to identify/recognize, let alone confirm the presence of a particular compound in a mixture by using just the nanomaterials. The electrochemical sensors of the present disclosure overcome this difficulty by using enzymes as bio-recognition elements on the sensor electrode platform.

Figure 2A:
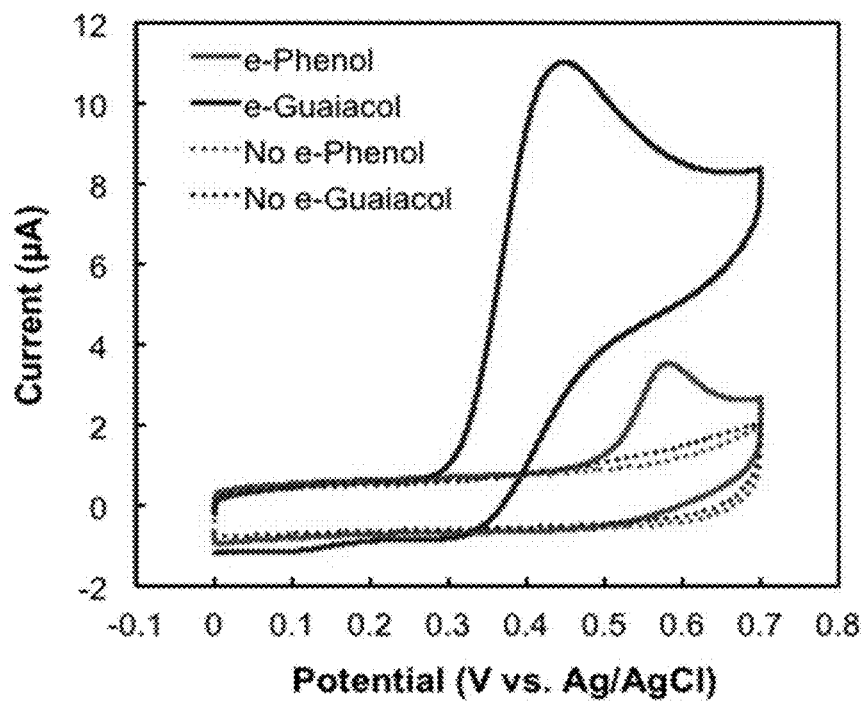
FIG. 2A illustrates cyclic voltammetry (CV) responses of ethyl phenol and ethyl guaiacol on an embodiment of a CNT/horseradish peroxidase (HRP) modified electrode.
Figure 2B:
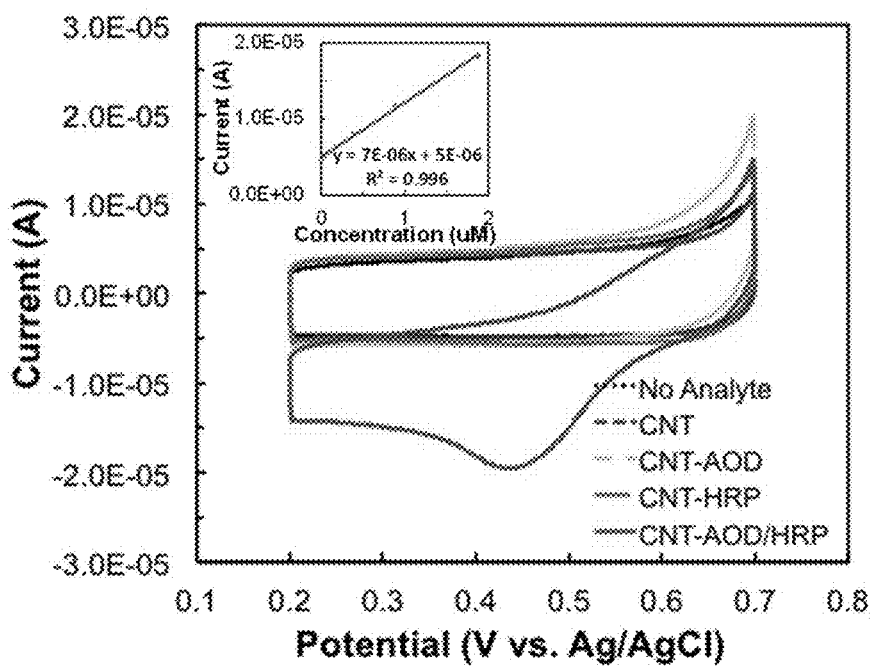
FIG. 2B illustrates CV responses of hydrolyzed methyl salicylate (salicylate and methanol) on various modified electrodes having no enzyme, 1 enzyme, and 2 enzymes (CNT only, CNT-AO, CNT-HRP, and CNT-AO/HRP).

Enzymes such as tyrosinase (TYR), laccase (Lc), bilirubin oxidase (BRO) and horseradish peroxidase (HRP) can be used to catalyze biochemical reactions involving oxygen or peroxide. Moreover, being phenol oxidases, these enzymes are also highly specific towards the reversible redox reactions of a wide number of phenolics and their corresponding quinone counterparts. The sensors and methods of the present disclosure demonstrate that when combined with nanomaterials such as carbon nanotubes (CNTs), graphene, gold, and metal oxide nanoparticles, the enzymes exhibit excellent bio-electrochemical activity towards the target analytes favoring fast and reliable amperometric detection. For example, as shown in FIG. 2A, an enhanced signal for ethyl phenol and ethyl guaiacol detection was observed when HRP was used as the bio-recognition element in a CNT-polymer matrix modified electrode. Also TYR and Lc can be used to electrochemically detect phenolic compounds with high specificity based on their quinone products (see Costello 1999 and Umasankar, Y. and Ramasamy, R. P., ECS Transactions 2013, both of which are incorporated by reference herein). Also, as described in more detail in Example 1, below, a highly selective detection of methyl salicylate was achieved using a bi-enzyme system using a combination of salicylate hydroxylase and tyrosinase (our NSF project) or in a second approach using a combination of alcohol oxidase (AO) and horseradish peroxidase, respectively. FIG. 2B also shows the voltammetric response of a bi-enzyme (AO) and (HRP) functionalized CNT electrode towards methyl salicylate in alkaline buffer with a sensitivity of 0.285 mA/mM·cm$^2$ and detection limit as low as 980 nM (~17 ppb), 2.3 times lower than OTL. With this capability (2 mL cell), a typical early release rate from the plants at 283 ng/hr/plant, would produce enough sample volume for detection within 1.05 hours, much earlier than visual symptoms occur. Currently no other method can achieve this without requiring expert analysis and expensive instrumentation.

Thus, the present disclosure provides electrochemical sensors, plant volatile detection systems, and methods for monitoring conditions of a plant or crop that utilize a bio-nanocomposite functionalized electrode for detection of volatile compounds indicative of plant stress and/or pathogen infection. In embodiments, the electrochemical sensors, detection systems, and methods of the present disclosure not only detect but can also quantify target volatile compounds. The bio-nanocomposite detection elements include a nanomaterial transducer material for enhanced sensitivity and enzymes capable of specific reaction with a target volatile for enhanced specificity. The volatile detection electrodes of the present disclosure are also configured to provide optimal electrochemical communication between the bio-nanocomposite and the electrode.

Volatile Detection Electrode

Embodiments of an electrochemical sensor of the present disclosure include a volatile detection electrode made of an electrode substrate and a bio-nanocomposite detection element on a surface of and/or in electrical communication with the electrode substrate. The bio-nanocomposite detection element includes a nanomaterial transducer material and at least one enzyme capable of specific reaction with a target volatile compound or its hydrolysis product. The nanomaterial transducer material act as nanomaterial supports for the enzymes as well as electronic transducers. This offers benefits including, but not limited to, enhanced surface area (providing enhancement of sensitivity), reliable support for enzyme attachment, and enhanced specificity due to high enzyme loading. In embodiments, the enzyme(s) are immobilized to the nanomaterial transducer material, and reaction between the enzyme(s) and the target volatile compound generates an electrical signal that is detected at the electrode. Detection of the electrical signal indicates the presence of the target volatile compound. The target volatile compound can be a stress-induced plant volatile compound and/or a target pathogen-emitted volatile compound. In embodiments, the electrochemical sensors of the present disclosure can detect both a stress-induced plant volatile and a pathogen-emitted volatile compound associated with a pathogen that induces the stress-induced plant volatile in the plant.

The electrode substrate can be any substrate capable of being functionalized with a nanomaterial transducer material and/or the bio-nanocomposite detection element. Examples of electrode materials include carbon, gold, platinum, silver, ruthenium, palladium, rhodium, osmium, iridium, or the like. In some embodiments, the nanomaterial transducer material can serve as the electrode and the transducer material. In such embodiments where the nanomaterial serves as the electrode, the substrate does not have to be electrically conductive and can be made of materials including, without limitation, ceramic materials, such as oxides (e.g., silica, fused silica, amorphous silica, fused amorphous silica, sapphire, or the like), nitrides (e.g., silicon nitride, boron nitride, or the like), carbides, oxycarbides, oxynitrides, or the like; polymeric materials (e.g., epoxies, phenolic papers, polyesters, or the like); fiberglass; or the like. In embodiments, the electrode substrate can be carbon, such as, but not limited to a modified screen printed carbon electrode (SPCE).

In embodiments, the nanomaterial transducer material is selected from carbon nanoparticles (e.g., multiwalled carbon nanotubes (MWCNTs)), metal nanoparticles, and metal oxide based nanomaterials. In embodiments, metal nanoparticles can include, but are not limited to, gold, silver, and/or platinum nanoparticles. In embodiments, the nanomaterial transducer material includes multiwalled carbon nanotubes.

Metal oxide ($MO_x$) nanomaterials are inexpensive alternatives to precious metals (Au, Ag or Pt), and offer characteristics important for electrochemical sensor applications at a fraction of the cost. Metal oxides can act as good catalysts for dehydrogenation and/or decomposition of VOCs such as aliphatic alcohols, ketones, acetic acid, and the like. Also, by varying the shape and size of $MO_x$, one can control their chemical adsorption properties. Third, intrinsically n-type semi-conducting $MO_x$ such as $TiO_2$, $SnO_2$, and $ZnO$ can be used for amperometric signal generation even in aqueous environments. In embodiments, metal oxide nanoparticles can include, but are not limited to, $TiO_2$, $SnO_2$, $ZnO$, and indium-tin oxide (ITO). In embodiments, the nanoparticles can be a specific shape, such as nanorods. In embodiments, the nanomaterial transducer material can be ITO nanoparticles, such as ITO nanorods. Some exemplary nanomaterial transducer materials for the electrochemical sensors of the present disclosure are discussed in greater detail below in conjunction with exemplary nanomaterial enzyme combinations as well as in the Examples below.

The enzymes for the sensors of the present disclosure include any enzymes capable of specific reaction with a target stress-induced plant volatile compound or a target pathogen-emitted volatile compound or the hydrolysis product of any of these compounds. In embodiments the enzyme is capable of specific reaction with a target stress-induce plant volatile compound or target pathogen-emitted volatile compound, but in other embodiments, the volatile compound is first hydrolyzed (e.g., by exposure to other chemicals in the sensor system or environment) and then one or more immobilized enzymes reacts with the hydrolysis product. In embodiments, there are more than one enzyme where each enzyme reacts with a different compound in a cascade of reactions beginning with the target volatile compound. In embodiments, target stress-induced plant volatile compounds include, but are not limited to, methyl salicylate, ethyl phenol, ethyl guaiacol, octanone, octanol, green leaf volatile compounds (e.g., hexenol, hexenal, hexyl acetate, hexenyl acetate, and terpenes), and derivatives of these volatile compounds. Exemplary plant pathogens for detection in the present disclosure include, but are not limited to, *Fusarium* species, a *Phytophthora* species, and a *Sclerotium* species. In embodiments, target pathogen-emitted volatile compounds include volatile compounds emitted from one or more of the above-listed plant pathogens. In embodiments, target pathogen-emitted volatile compounds include, but are not limited to ethyl phenol, ethyl guaiacol, octanone, and combinations of these volatile compounds. Additional details regarding some of the above-listed volatile compounds are provided below.

Exemplary enzymes capable of reaction with one or more of the above-listed volatile compounds or their hydrolysis products include, but are not limited to: tyrosinase (TYR), laccase (Lc), bilirubin oxidase (BRO), horseradish peroxidase (HRP), salicylate hydroxylase, alcohol oxidase (AO), alcohol dehydrogenase (ADH), tannase, esterase, and combinations of more than one of these enzymes. In some embodiments, one or more enzymes can be included in a volatile detection electrode, where the enzymes interact with the target volatile compound to produce a cascade of reactions, the product of which is detected by the sensor. For instance, in an embodiment of a multi-enzyme system, a bi-enzyme system may be used, where at least one enzyme reacts with the target volatile compound or its hydrolysis product to produce a first reaction product, and a second enzyme reacts with the first reaction product to produce a second reaction product, where the second reaction product or the second reaction produces an electrical signal capable of being detected by the electrode. In embodiments, a tri-enzyme system may also be employed, where at least one enzyme reacts with the target volatile compound producing a cascade of reactions involving the other enzymes of the system, where at least one of the reactions (e.g., the final reaction in the cascade) produces an electrical signal capable of being detected by the electrode. Although bi-enzyme and tri-enzyme systems are described in greater detail herein, variations on such multi-enzyme systems are contemplated within the scope of the present disclosure. Additional details with respect to some of the above-listed enzymes and enzyme systems are provided in the discussion below.

In embodiments, the electrochemical sensor of the present disclosure can specifically detect two or more different target volatile compounds. In embodiments, the electrochemical sensor includes two or more volatile detection electrodes, where at least one volatile detection electrode detects a different target volatile compound than at least one other volatile detection electrode. In other embodiments, a single volatile detection electrode may be configured with different areas for detection of different volatile compounds.

In some embodiments, the electrochemical sensor includes two or more volatile detection electrodes, where a first volatile detection electrode detects a target plant pathogen-emitted volatile compound and a second volatile detection electrode detects a target stress-induced plant volatile associated with infection by a plant pathogen that emits the target plant pathogen-emitted volatile compound. In this manner, the sensor can detect both the pathogen as well as that the plant is in stress from the pathogen, providing further verification of infection. For instance, in some embodiments, the stress-induced plant volatile is methyl salicylate and the target plant pathogen-emitted volatile compound is selected from the group of VOCs including, but not limited to: octanone, ethyl phenol, and ethyl guaiacol. Other embodiments include other combinations of plant pathogen-emitted volatile compounds and stress-induced plant volatile compounds.

Figure 3A:
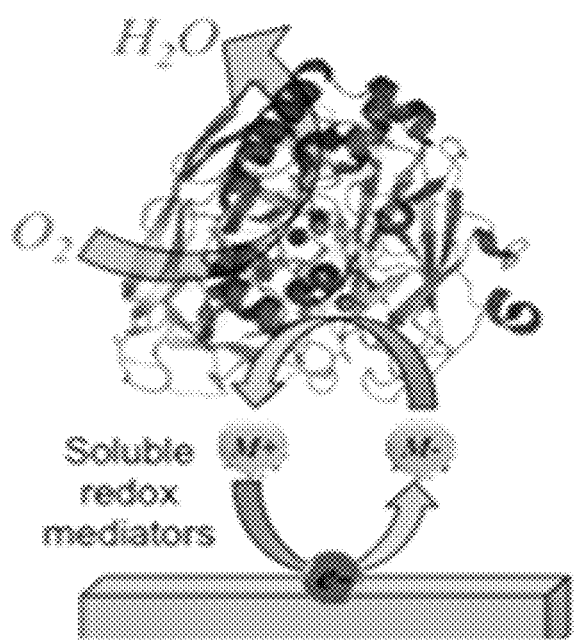
FIGS. 3A and 3B are schematic illustrations of electron transfer between an enzyme and the electrode surface, showing mediator facilitated electron transfer (FIG. 3A) vs. direct electron transfer (FIG. 3B).
Figure 3B:
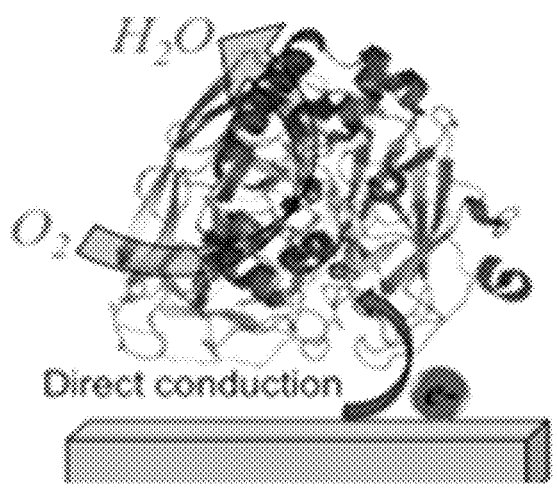

Functionalizing nanomaterials with enzymes to provide the bio-nanocomposite detection element of the biosensor involves an intimate attachment between the two, so that an electrical communication can be established between the nanomaterial transducer and enzyme active site. The enzyme active site is often buried deep inside the insulating polypeptide matrix and may be unavailable for direct communication with the electrode. To overcome this, in embodiments, a "redox shuttle" or "mediator" could be used to facilitate the electron transfer, as shown in FIG. 3A. In embodiments of the present disclosure, nanomaterial supports and immobilization methods are selected that favor direct electrical communication (FIG. 3B).

Various approaches known to those of skill in the art for enzyme immobilization to carbon, metal, and metal oxide based nanomaterials can be employed for the sensors of the present disclosure. Immobilization can be by direct or indirect linking so long as it provides for electrochemical communication between the enzyme and the nanomaterial. For example, a non-covalent sidewall functionalization can be effective for direct electrical communication between metalloenzymes and carbon nanotube/graphenes (for example as described in Ramasamy, et al., Chem Commun 2010, Parimi, et al., Acs Catal 2012, and Calkins, et al., Energ Environ Sci 2013, which are hereby incorporated by reference herein). Dendrimer based covalent strategies can be used in embodiments to bind enzymes onto gold nanoparticles (for example as described in Umasankar and Ramasamy, ESC Transactions 2013 (incorporated by reference above)). In other embodiments, a two-step immobilization procedure can be used to immobilize multiple enzymes onto metal oxide nanostructures, resulting in high bio-electrocatalytic activity.

In embodiments, enzyme immobilization is achieved using an approach in which the nanomaterial transducer material (such as, but not limited to, ITO nanoparticles) is functionalized with a silane cross-linker having terminal amine groups (e.g., APTES) as illustrated in FIG. 5. Then an amine-amine crosslinker (e.g., 1,5-difluro-2,4-dinitrobenzene) can be used to establish protein attachment linkers on the surface to which the enzymes will be covalently attached through imide-bonds. The length of cross-linker can be adjusted to accommodate different enzyme sizes. In embodiments, such as with a multi-enzyme system, two or more crosslinkers of varying lengths can be employed to accommodate two or more layers of enzymes.

Figure 6:
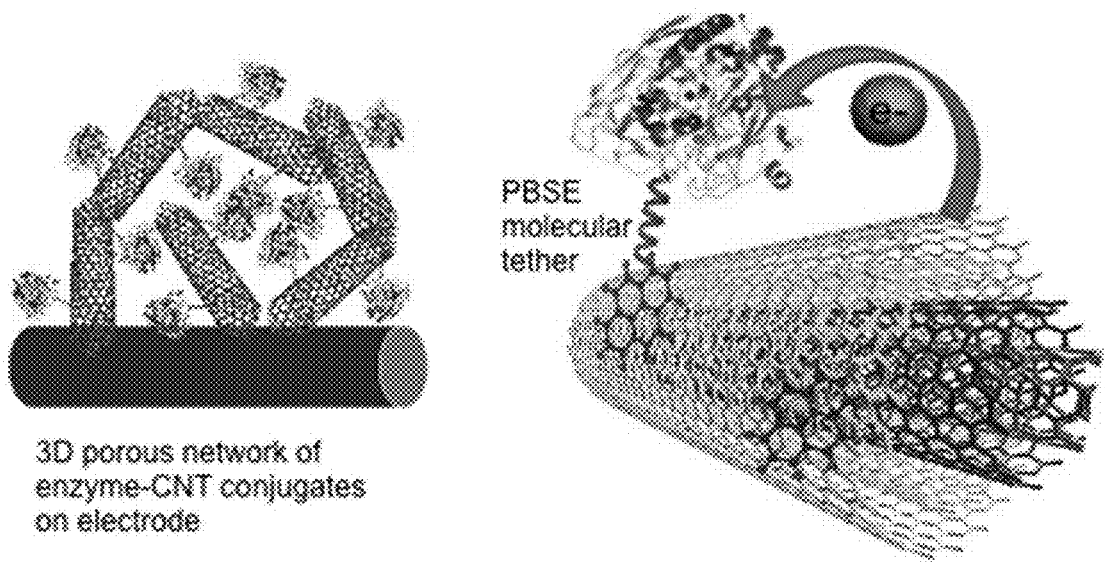
FIG. 6 illustrates embodiments of an electrode modified with a three dimensional matrix of carbon nanotubes functionalized with enzymes attached to the CNTs with a molecular tether.
Figure 7A:
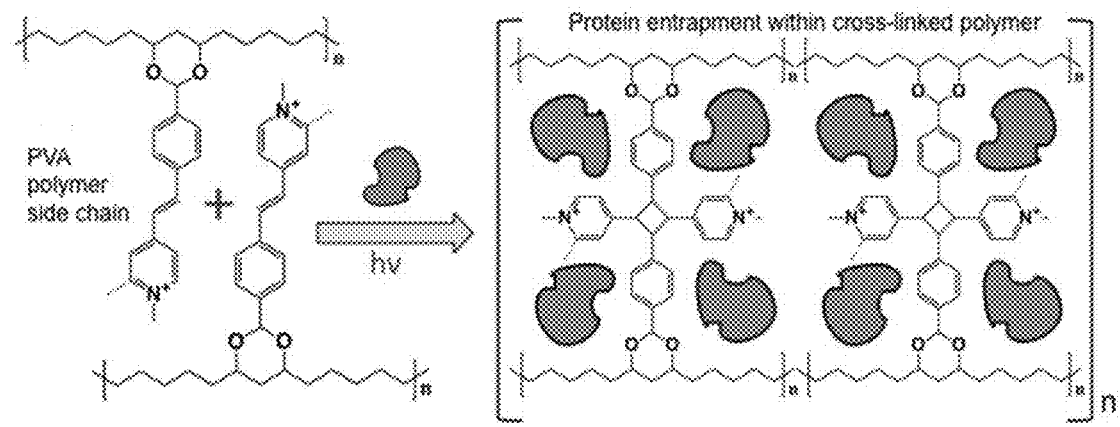
FIGS. 7A and 7B illustrate an embodiment of a method of functionalizing a CNT surface with enzymes using crosslinked PVA polymers to tether/entrap the enzymes to form a CNT/enzyme 3D matrix on an electrode surface.
Figure 7B:
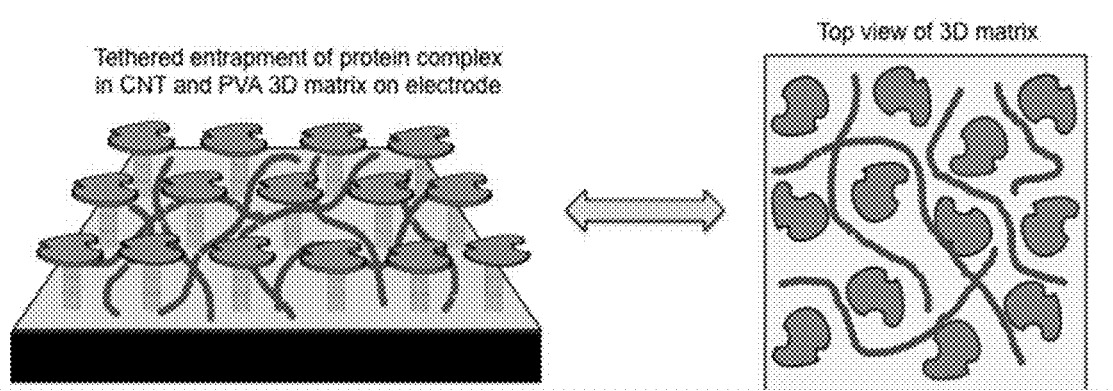

In other embodiments, such as when the nanomaterial transducer material is MWCNTs, the nanomaterial is non-covalently functionalized with a tethering agent, such as, but not limited to, 1-pyrene butanoic acid succinimidyl ester (PBSE), as illustrated in FIG. 6. In embodiments, the tethering agent can be other heterobifunctional tethering agents of the PBSE-type, such as, but not limited to 4,4'-[(8,16-dihydro-8,16-dioxodibenzo[a,j]perylene-2,10-diyl) dioxy] dibutyric acid di(N-succinimidyl ester) (DPPSE). The NHS-ester groups of the molecular tethers can be covalently linked to amine groups of the one or more enzymes to be used for specific detection. In embodiments, such as illustrated in FIGS. 7A and 7B, the surface of carbon nanotubes as the transducer material is modified with polyvinylalcohol-N-methyl-4(4'-formylstyryl) pyridinium-methosulfateacetal (PVA-SbQ) polymer, a polymer that enhances conductivity and facilitates charge transfer in the bio-nanocomposites via electrostatic interactions. In addition, this photo-switchable polymer can also be activated by UV light to cross-link the SbQ side chains, thereby entrapping the enzyme and nanomaterials resulting in high enzyme stability over time.

Example Volatile Detection Enzymes

Some exemplary enzyme/volatile compound detection combinations are described in additional detail in the present section, but one of skill in the art will understand that these are not intended to be limiting examples and other combinations and variations are possible.

Methyl Salicylate: In embodiments of the electrochemical sensor of the present disclosure for methyl salicylate detection, a multi-enzyme system can be used for detection. In an embodiment, a bi-enzyme system is used for amperometric detection as shown in FIG. 4A and described in Example 1 below. The detection is based on cascade enzyme reactions: (i) room temperature hydrolysis of methyl salicylate to produce methanol; (ii) the enzymatic conversion of oxygen and methanol to hydrogen peroxide and $H_2O_2$ by alcohol oxidase (AO) enzyme; and, finally, (iii) the enzymatic electrochemical reduction of $H_2O_2$ to water using horseradish peroxidase (HRP). The electrons used for the HRP reaction will generate an amperometric signal that can be correlated to the concentration (quantity) of methyl salicylate in the analyte. This method of detection is highly selective and only happens when both enzymes are present, with little or no interference from other reaction products. Also it provides more reliable detection over methods based on salicylate hydroxylase and methanol dehydrogenase enzymes.

Another embodiment of a bi-enzyme system for detection of methyl salicylate is described below in Example 3. In an embodiment, the bi-enzyme system includes salicylate hydroxylase (SH) and tyrosinase (TYR). The system is based on the following cascade of reactions: (i) hydrolysis of methyl salicylate to salicylate; (ii) the enzymatic conversion of salicylate to catechol by SH; and, finally, (iii) the enzymatic oxidation of catechol to 1,2-benzoquinone by TYR. The reduction current of the 1,2-benzoquinone produced by the final reaction can be detected and measured at the electrode.

In another embodiment, a tri-enzyme system, such as described in greater detail in Example 4, below, can be used for methyl salicylate detection. In embodiments, the tri-enzyme system employs another enzyme at the beginning of the cascade to catalyze the initial hydrolysis of methyl salicylate, for a total of 3 enzymes in the cascade. Thus, the three enzyme system employs a first enzyme for the hydrolysis of methyl salicylate and then two additional enzymes, such as described above. In embodiments, the first enzyme in the tri-enzyme system can be tannase, esterase, or other enzymes capable of hydrolysis of methyl salicylate to salicylate and methanol. The two other enzymes can be an enzyme pair such as, but not limited to: SH/TYR or AO/HRP, as described above.

Ethyl-phenol and Ethyl-guaiacol: In embodiments of the electrochemical sensor of the present disclosure for ethyl phenol and ethyl guaiacol detection, phenol oxidases that possess good selectivity towards either of these compounds can be used. Both tyrosinase (TYR) and horseradish peroxidase (HRP) enzymes exhibit high electrochemical activity towards ethyl phenol and ethyl guaiacol oxidations (see FIGS. 2A-2B). As shown in FIG. 4B, in the absence of $O_2$ and $H_2O_2$, the enzymes TYR or HRP oxidize phenolic compounds and deliver the electrons to the electrode, which can be captured as an amperometric signal for the analyte detection.

Non-enzyme based detection of ethyl-guaiacol is described in Example 2 below. Such embodiments can be modified with enzyme systems as described herein for improved specificity.

An embodiment of an enzyme based electrochemical sensor for detection of ethyl phenol is described in greater detail in Example 5, below. An embodiment of an electrochemical sensor of the present disclosure for p-ethylphenol detection includes tyrosine as the enzyme in electrical communication with the nanomaterial transducer material (such as MWCNTs, metal oxide nanoparticles, and the like as described above). In such embodiments, tyrosinase enzymatically oxidizes p-ethylphenol to 4-ethyl-1,2-benzoquinone. The reduction of 4-ethyl-1,2-benzoquinone to 4-ethyl-1,2-hydroquinone is detected at the electrode. Additional description of this embodiment is provided in Example 5, below.

Octanone: This long chain aliphatic ketone is typically hard to detect selectively using conventional nanomaterials. However, in embodiments of the electrochemical sensor of the present disclosure for detecting octanone, upon functionalizing the nanomaterials with alcohol dehydrogenase (ADH) enzymes, the compound and its corresponding reduced form, octanol can be selectively detected based on the NADH oxidation currents, as NADH progressively gets consumed in the reaction, as shown in FIG. 4C. Regeneration of cofactors such as NADH is not critical, as the sensor electrode strips are not meant to be re-used. This enzyme has been used before for demonstrating ketone reduction, but not for electrochemical sensing.

A challenge in dealing with enzymes is to create a compatible environment for both the reactants (target compounds) and the enzymes used for the reactions. Ideally the VOCs are solubilized in desired concentrations. Most of the target VOCs are sufficiently soluble in aqueous buffer at enzyme relevant pH. However, in case of solubility issues (possibly with octanone), biocompatible, water soluble, ionic liquid electrolytes (e.g AMMOENG™ 101) can be used as prescribed in the literature, for example Kohlmann, C. et al., Environ Entomol 2003; van Rantwijk, F. and Sheldon, R. A., Chem Rev 2007; and roosen, C. et al., Appl Microbiol Biot. 2008, which are incorporated by reference herein.

Green leaf volatiles: Various routes exist for electrochemical detection of common green leaf volatiles (GLV) such as hexenol, hexanone and hexyl acetate using electrochemical biosensors (see, Umasankar, Y., et al., Electroanalytical studies on green leaf volatiles for potential sensor development. Analyst 2012, 137, 3138-3145, incorporated by reference herein). Such systems can be integrated into the enzyme based electrochemical biosensors of the present disclosure. GLV have also been evaluated in the examples below as potential interfering compounds for the above-described biosensors, as GLV are commonly released under all conditions, but at varying concentrations.

Example Enzyme-Nanomaterial Composite

Some exemplary enzyme-nanomaterial composite combinations are described in additional detail in the present section, but these are not intended to be limiting examples, and other combinations and variations are possible.

Due to their low active site loading per unit area, for the sensors of the present disclosure, enzymes are immobilized on nanomaterial supports that also act as electronic transducers. This forms a bio-nanocomposite detection element that provides multiple benefits (i) enhanced surface area (sensitivity enhancement); (ii) reliable support for enzyme attachment and (iii) enhanced specificity due to high enzyme loading. However, the choice of nanomaterials depends on their properties and the type of enzyme immobilization methods. Some non-limiting examples discussed in greater detail here include indium-tin oxide (ITO) and carbon nanotubes, described briefly above, both of which provide desirable properties for the target reactions and enzymes.

Indium Tin Oxide Nanostructures

Metal oxide (MOx) nanomaterials are inexpensive alternative to precious metals (Au, Ag or Pt), and offer many characteristics desirable for electrochemical sensor applications, at a fraction of the cost. Metal oxides have been reported to act as good catalysts for dehydrogenation and/or decomposition of VOCs such as aliphatic alcohols, ketones, acetic acid, etc. By varying their shape and size, one can control their chemical adsorption properties. Intrinsically n-type semi-conducting MOx such as $TiO_2$, $SnO_2$, ZnO can be used for amperometric signal generation even in aqueous environment as demonstrated in Example 2, below. Finally, the surface of MOx nanoparticles can be functionalized with enzymes for bioelectrochemical reactions, such as illustrated in FIG. 5A and as demonstrated in Zhou, Y., et al., 225th Electrochemical Society Meeting, Orlando, 2014 and Zhou, Y. et al., Acs Catal 2014, incorporated by reference above.

Embodiments of two architectures of highly conducting indium-tin oxide (ITO) nanomaterials can be used as enzyme supports. One type is commercially available ITO nanoparticles in different sizes that can be deposited on the strip electrodes. Another type is ITO nanorod arrays, which can be directly grown on the surface of ITO coated conducting glass slides or strips electrodes using oblique angle physical vapor deposition (PVD) process as described in Wolcott, A. et al., Small 2009. The length, diameter and spacing (density) of the ITO nanorods can be controlled by varying the PVD parameters.

The ITO nanoparticles and nanorods can then be subject to enzyme immobilization. In embodiments, an immobilization approach is used as described in Zhou, $225^{th}$ Electrochemical Society Meeting 2014 and Zhou ACS Catal 2014, incorporated by reference above. Briefly, as shown in FIG. 5B, first the ITO nanostructures (particles, rods, or spheres) are functionalized with a silane cross-linker terminating with amine groups (e.g., APTES). Next an amine-amine crosslinker (e.g., 1,5-difluro-2,4-dinitrobenzene) is used to establish protein attachment linkers on the surface to which the enzymes will be covalently attached through imide-bonds. The length of cross-linker can be adjusted to accommodate different enzyme sizes. The choice of enzyme will depend on the type of target compound as discussed herein. For bi-enzyme systems, in embodiments two cross-linkers of varying lengths can be used to accommodate two layers of enzymes or co-immobilize them if pH conditions permit.

Carbon Nanotubes

In embodiments multi-walled carbon nanotubes (MWCNTs) can be used both as stand-alone material and as enzyme immobilization supports for sensor electrode development. CNT have high affinity towards aromatic moieties, present in VOCs. For linking enzymes and CNTs to establish direct electrical communication, in some embodiments a molecular tethering method can be used, such as described in Ramasamy, et al., Chem Commun 2010, incorporated by reference above. In this method, MWCNT can be non-covalently functionalized with 1-pyrene butanoic acid succinimidyl ester (PBSE), such as illustrated in FIG. 6, or other similar tethering agents such as N-1(1-pyrenyl maleimide), 4,4'-[(8,16-dihydro-8,16-dioxodibenzo[a,j]perylene-2,10-diyl)dioxy] dibutyric acid di(N-succinimidyl ester) (DPPSE) and other PBSE-type heterobifunctional tethering agents (see Atanassov, et al., 2014, incorporated by reference herein). Then, the NHS-ester groups of the molecular tethers will be covalently linked to the amine groups of the enzyme. Since the diameters (curvature) and chirality plays an important role in this type of immobilization, they will be varied as needed using commercially available nanotubes. This method suits both AO and HRP for developing bi-enzyme systems.

Figure 8:
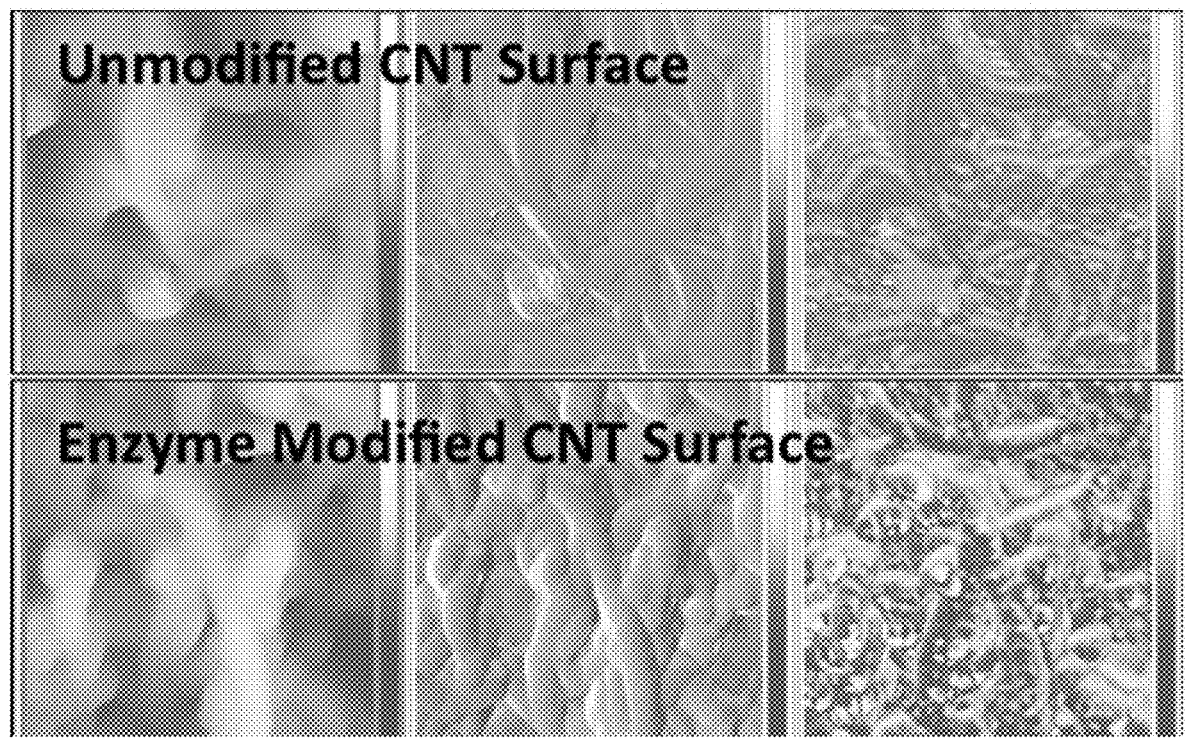
FIG. 8 are AFM digital images illustrating the difference in morphology between unmodified (top) and enzyme modified (bottom) CNT surfaces.

In embodiments, such as illustrated in FIGS. 7A and 7B, the surface of CNT was modified with poly-vinylalcohol-N-methyl-4(4'-formylstyryl) pyridinium-methosulfateacetal (PVA-SbQ) polymer (see Nam, et al., Org Electron 2009, which is hereby incorporated by reference herein), which was found to enhance conductivity and facilitates charge transfer in the bio-nanocomposites via electrostatic interactions. In addition, this photo-switchable polymer can also be activated by UV light to cross-link the SbQ side chains, thereby entrapping the enzyme and nanomaterials resulting in high enzyme stability over time. Magnified images of enzyme modified and unmodified CNT surfaces are illustrated in FIG. 8.

Systems

In embodiments, the electrochemical sensors of the present disclosure are part of a detection system. In embodiments, the volatile detection electrode is a working electrode of an electrochemical cell, such as a standard 3 electrode cell. In embodiments, the electrochemical cell also includes a counter electrode and reference electrode in electrochemical communication with the working electrode and a potentiostat to supply an electrical current to the electrochemical cell and monitor changes in the electric current generated at the working electrode. In embodiments, the changes in the electric current in the electrochemical cell are recorded as a cyclic voltammogram, differential pulse voltammogram or some other form of current response to an applied potential or voltage.

In embodiments, the electrochemical sensor is part of a plant volatile detection system. In embodiments, plant volatile detection systems of the present disclosure include a volatile collection reservoir adapted to collect volatile compounds emitted from a plant, an electrochemical sensor, and a signal processing mechanism. In embodiments, the electrochemical sensor includes an electrochemical cell having a volatile detection electrode as described above (the working electrode), counter and reference electrodes, and a potentiostat to supply an electric current to the electrochemical cell and monitor changes in the electric current produced at the working electrode. The volatile detection electrode is in fluid communication with the volatile collection reservoir such that volatile compounds collected in the reservoir can be transferred to a detection surface of the volatile detection electrode, and the counter and reference electrodes are in electrochemical communication with the volatile detection electrode. In embodiments, the signal processing mechanism in operative communication with one or more elements of the electrochemical sensor, and the signal processing mechanism has data transfer and evaluation software protocols configured to transform raw data from the electrochemical sensor into diagnostic information regarding the presence or absence or levels of the plant volatile compound.

In embodiments, the signal processing mechanism can be, but is not limited to, a personal computer, a mainframe, a portable computer, a personal data assistant, a smart phone, and a tablet computer, or a combination thereof. In embodiments, the plant volatile detection system is portable and adapted for sampling volatiles in a field environment. Other embodiments include a smart phone application configured to receive information from the signal processing mechanism and transform the information into alerts, recommendations, or both for a user.

In general, detection systems of the present disclosure include additional instrumentation for the system (e.g., signal processing circuitry, a reference electrode, a counter electrode, a potentiostat, and/or an electrochemical workstation), and a signal processing mechanism (e.g., a personal computer, mainframe, portable computer, personal data assistant, or the like), each of which could be in operative communication with one or more of the other components. For instance, in embodiments, the electrochemical sensor systems and detection systems of the present disclosure may include or may be integrated with at least one of the following: a reference electrode and a counter/auxiliary electrode; one reference electrode and one counter/auxiliary electrode for each volatile detection electrode in a system; an electrochemical workstation; a signal processing mechanism, wherein the signal processing mechanism comprises data transfer and evaluation software protocols configured to transform raw data into diagnostic information; a temperature control mechanism; or a fluid control mechanism.

By way of example, the volatile detection system can be configured such that the volatile detection electrode (working electrode) is coupled to counter and reference electrodes and an electrochemical workstation that provides a current or voltage source to the electrodes to effect a flow of electrons to the electrochemical cell that is monitored and measured at the workstation by a computer, which reports and records the voltammetric current. The voltammetric current, and changes therein, can be recorded as a cyclic voltammogram. The computer system can include data transfer and evaluation protocol capable of transforming raw data from the volatile detection electrode into information regarding the presence and/or absence of a target analyte. The computer can also be capable of providing diagnostic information regarding the target analyte. In certain situations, the computer is a portable personal computer that includes data transfer and evaluation software capable of storing and analyzing the recorded signals. Under these circumstances, the biosensor instrument can provide a diagnostic tool that itself is portable and is powered from the laptop computer.

The electrochemical sensors of the present disclosure are capable of providing a specific electrochemical excitation signal that is optimized to yield the maximum diagnostic value. These systems thus can represent a complete diagnostic package with the capability to aid rapid analysis by a person who has minimum technical training. In exemplary embodiments, the raw electrochemical output from the electrochemical sensor of the present disclosure is collected and transferred to the memory of a computer, which includes a pattern recognition evaluation program that can be "trained" to identify a specific binding event and also the degree of the matching between the capture molecule and the target analyte (e.g., stress-induced plant volatile and/or pathogen emitted volatile), and thus recognize the signature of a particular binding event for which it was "trained". Such a detection system provides a complete diagnostic package whose purpose is to aid rapid screening, detection, and analysis of a target analyte, without elaborate preparation, by a person who has minimum technical training and to enable portability of such a system, bringing heretofore unavailable diagnostic and monitoring capabilities to large and/or remote areas.

The various electrodes can be in operative communication with an electrochemical workstation that provides a current or voltage source to the three electrode cell. This provides a flow of electrons to the three-electrode cell(s) that is monitored and measured at the workstation by a signal processing mechanism, which reports and records the voltammetric current. The voltammetric current, and changes therein, can be recorded as a cyclic voltammogram. The workstation may provide a voltage source to the electrode and measure a current, but it is also capable of working in reverse providing a current source and measuring a voltage. Either set-up is acceptable for operating the biosensor instruments of the present disclosure.

The signal processing mechanism can be a personal computer, mainframe, portable computer, personal data assistant, or the like. The signal processing mechanism can include data transfer and evaluation protocol capable of transforming raw data from the biosensor array into information regarding the presence, absence, and the extent of the interaction of a target volatile compound(s). The signal processing mechanism can also be capable of providing diagnostic information regarding the target volatile(s).

Generally, the solid state electronics, including, for example, a potentiostat circuit connected to working and reference electrodes, as described above for performing electrochemical measurements, are external to the volatile detection electrode (and any printed circuit board package associated with the volatile detection electrode to enable connection to other elements of an electrochemical cell potentiostat circuitry, etc.). Notwithstanding this, the volatile detection electrode, reference and counter/auxiliary electrodes, electrochemical workstation, and signal processing mechanism can be arranged in a variety of configurations, when in combination with other components that are known to those of skill in the art.

Again, the volatile detection electrode can also include signal processing circuitry, as discussed above. The electrode is then contacted with a sample to be analyzed (e.g., in sufficient contact with the sample for a target volatile compound contained in the sample to interact with the enzyme(s) on the volatile detection electrode), and the system is interrogated using standard electrochemical techniques. As discussed above, the electrochemical sensor/detection system includes a current source to provide a flow of electrons to drive the electrochemical processes at the volatile detection electrode and a signal processing mechanism for detecting and reporting any change at the electrode. As discussed above, some embodiments of the volatile detection system also include a data analysis component (e.g., data analysis software on a computer system coupled to the biosensor array described above) for storing and evaluating the electrochemical signal produced by the biosensor-chip array.

Those skilled in the art to which this disclosure pertains will also appreciate that the sensing portion of the biosensor instrument (e.g., volatile detection electrode) can be reusable. The sensor can be washed and reused to detect the same volatile compound(s) in a different sample. Those of skill in the art will also understand that the electrochemical volatile sensor of the present disclosure, prepared in an array format, can be adapted to detect many different volatile compounds and used for high throughput applications.

In embodiments, the plant volatile detection system of the present disclosure can be portable and adapted for sampling volatiles in a field environment. In some such embodiments, the signal processing mechanism may be a portable personal computer, such as a laptop, tablet, or the like. In embodiments, the plant volatile detection system of the present disclosure can also include or be configured to interact with a smart phone application configured to receive information from the signal processing mechanism and transform the information into alerts, recommendations, or both for a user. Such portable systems can be useful for field application, so that farmers or other professionals or technicians can carry the equipment to the field for testing, rather than bringing a sample back to a laboratory or sending it off for testing.

Methods for Monitoring Plants

The present disclosure also includes methods of using the sensors and systems of the present disclosure to monitor the condition plants, crops, harvested plants and plant parts (e.g., fruits, vegetables, etc.). In embodiments, the methods include monitoring for infection by a plant pathogen, such as but not limited to a fungus, insect, or bacterial organism that produces volatile compounds and/or induces the infected plant to produce certain stress-induced volatile compounds.

In embodiments, methods of the present disclosure for monitoring a condition of a plant or crop of plants include periodically sampling volatile emissions from the plant or one or more crop plants using the electrochemical sensors and/or plant volatile detection systems of the present disclosure and analyzing the information provided by the signal processing mechanism, where the presence or amount of one or more target plant volatile compounds indicates the presence of a plant disease associated with the one or more volatile compounds. In embodiments, the method may include using an application that interacts with the signal processing mechanism of the detection system and provides information and/or recommendations based on the information provided by the signal processing mechanism based on the data received from the electrochemical sensor. In embodiments, methods of the present disclosure also include treating the plant or crop for a disease/pathogen when the volatile detection system indicates infection by a plant pathogen.

Additional details regarding the methods and compositions of the present disclosure are provided in the Examples below. The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following claims.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

EXAMPLES

Figure 9:
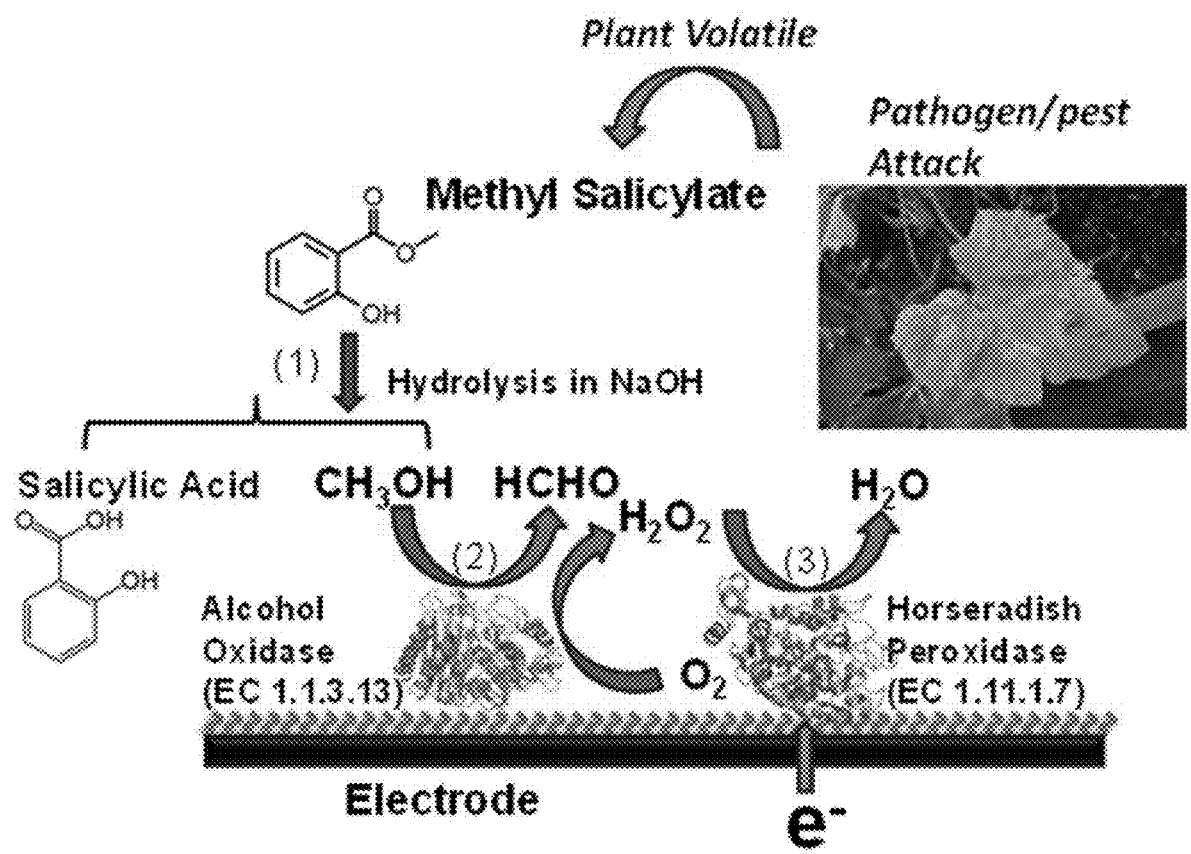
FIG. 9 is a schematic illustration of methyl salicylate detection by an embodiment of a bi-enzyme modified electrode with alcohol oxidase (AO) and horseradish peroxidase (HRP). The process carries out as hydrolysis of methyl salicylate to form salicylic acid and methanol (1), oxidation of methanol and production of hydrogen peroxide (2) and direct electron transfer from electrode to hydrogen peroxide by horseradish peroxidase (3).

Now having described the embodiments of the present disclosure, in general, the following Examples describe some additional embodiments of the present disclosure. While embodiments of present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure Example 1—Bi-Enzyme Sensor Detection of Methyl Salicylate with AO and HRP The present example and accompanying drawings describe an embodiment of a electrochemical biosensor of the present disclosure for detecting methyl salicylate, such as illustrated in FIG. 9. An embodiment of a methyl salicylate electrochemical biosensor can be constructed using enzyme functionalized nanomaterial composite that selectively detects hydrolyzed methyl salicylate. The conduction of the biosensor is described below.

Figure 10:
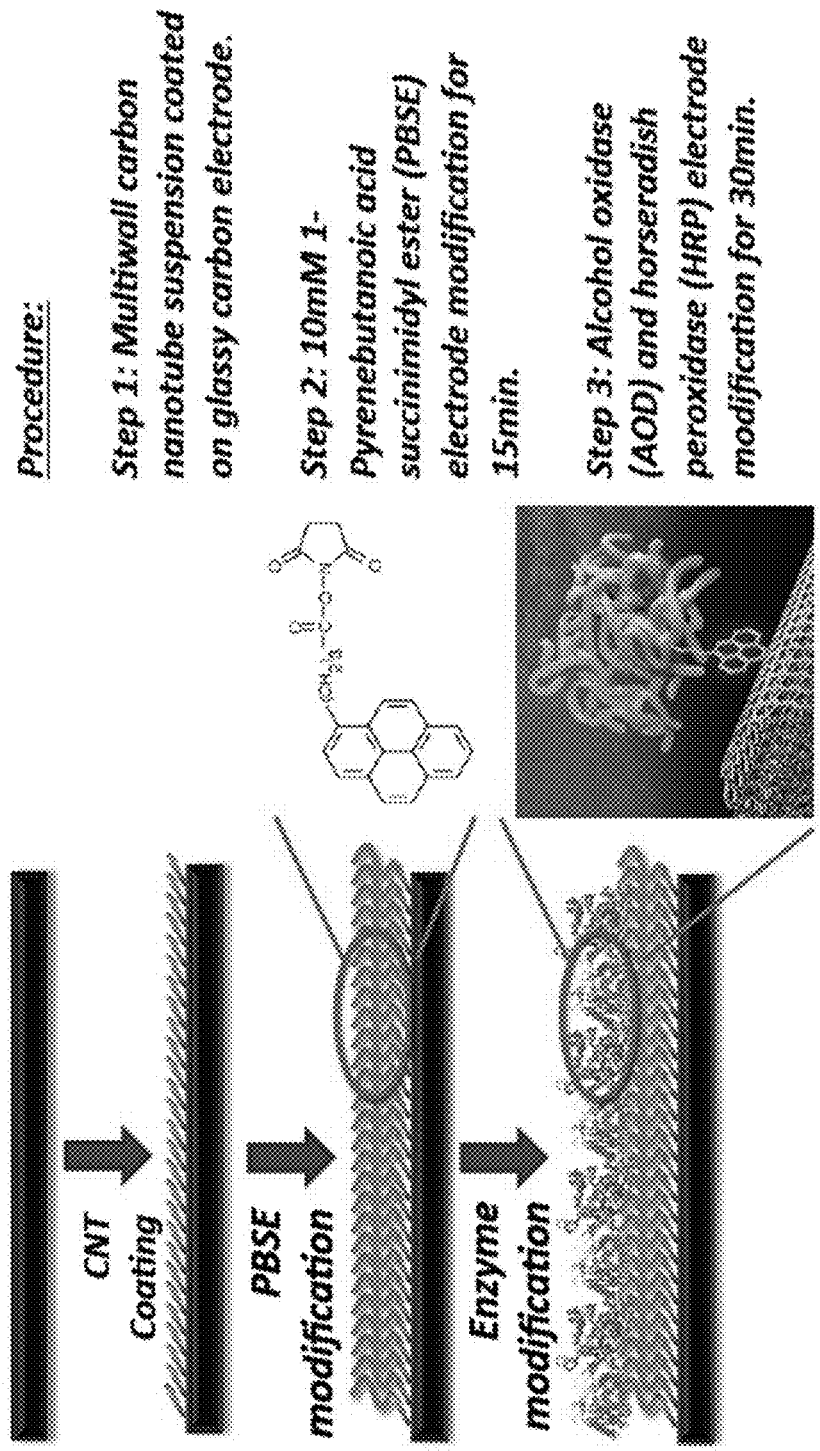
FIG. 10 is a schematic illustration of a method of preparing an embodiment of an enzyme modified sensor of the present disclosure showing coating an electrode substrate with a multiwall carbon nanotube transducer material, modifying the MWCNT coated substrate with PBSE, and finally functionalizing the prepared electrode with enzymes AO and HRP.

A screen-printed carbon electrode (strip electrode) was modified with multi-walled carbon nanotubes. The carbon nanotubes provide the high surface area for enzyme-electrochemical reactions, while at the same act as immobilization support for the enzymes. Two enzymes, alcohol oxidase (AO) and horseradish peroxidase (HRP) (bio-recognition elements) were immobilized onto the carbon nanotubes (transducer), using a hetero-bifunctional tethering agent, namely 1-pyrene butanoic acid succinimidyl ester (PBSE) as shown in FIG. 10.

The resulting bi-enzyme carbon nanotube composite carries out a cascadic conversion of hydrolyzed methyl salicylate into hydrogen peroxide. This cascadic conversion proceeds as follows: The first step involves the hydrolysis of methyl salicylate into methanol and salicylic acid in basic medium (NaOH) as illustrated in step (1) of FIG. 9. The second step involves the enzymatic oxidation of methanol to formaldehyde and simultaneous reduction of oxygen to hydrogen peroxide by the enzyme alcohol oxidase as illustrated in step (2) of FIG. 9. The third step involves the selective reduction of hydrogen peroxide to water using a coupled electro-enzymatic reaction by the enzyme horseradish peroxidase as illustrated in step (3) of FIG. 9. The hydrogen peroxide reduction results in the amperometric signal, which can be detected at the electrode.

This electrode was attached to a standard 3 electrode cell, with potentiostat, and changes in amperometric signal at the working electrode (volatile detection electrode) were measured by cyclic voltammetry as shown in the figures. Details about fabrication and the experimental conditions and results are presented below an in FIGS. 9-20.

Experimental

Materials

Alcohol Oxidase (EC 1.1.3.13) solution from Pichia pastoris was purchased from Sigma-Aldrich and used as it received. Horseradish Peroxidase with activity 281.0 U/mg was purchased from Calbiochem. Multiwall carbon nanotube (MWNT) was obtained from DropSens. 1-pyrenebutanoic acid, succinimidyl ester (PBSE) was purchased from AnaSpec Inc., Fremont Calif. Dimethylformamide (DMF) was purchased from Acros Organics. Chemicals for interference study like cis-3-hexenol, hexyl acetate and cis-hexen-1-yl acetate obtained from TCI America (Portland, Oreg.) were used as received. Wintergreen oil purchased from Piping Rock Health Products, LLC was used as obtained for real sample study. Methyl salicylate (MeSA) was used as received from Sigma-aldrich. All other chemicals were used as analytical grade. 100 mM phosphate buffer (pH 7.6) was prepared for all experiments. All the aqueous solutions were prepared using 18.2 MΩ nano pure de-ionized (DI) water. Solutions were oxygenated by purging with purified oxygen for 15 min before each experiment.

Apparatus

Cyclic voltammetry and constant potential amperometry was performed using CHI 920c potentiostat. A conventional three-electrode system having a Pt wire as the counter electrode and 3 M Ag/AgCl as the reference electrode was used for electrochemical measurement. The working electrodes, both modified with multiwall carbon nanotube (MWNT), 1-Pyrenebutanoic acid, succinimidyl ester (PBSE), alcohol oxidase (AO) and horseradish peroxidase (HRP) are glassy-carbon (GC) electrode from CH Instrument, Inc. for cyclic voltammetry and rotating disk electrode (RDE) from Pine Instrument Company for constant potential amperometry. Rotating electrode speed control was also used. All experiments were carried out at 25±2° C.

Electrode Preparation and CV, I-t Measurement

Enzyme functionalized nanocomposite electrodes were prepared as illustrated in FIG. 10. GC and RDE electrodes were first polished on polishing pad with 0.05 micron allumina polishing powder from CH Instrument Inc. before each experiment. The electrodes were then sonicated and rinsed by DI water to remove the fine powder adhered to the electrode surface. MWNT suspension was prepared by ultrasonication of 1 mg of MWNT in 1 mL DMF for 1 hour. The MWNT modified electrodes were prepared by drop casting 8 μL (in 8 steps of 1 μL) for GC electrode and 12 μL (in 3 steps of 4 μL) for RDE followed by drying at 70° C. MWNT modified electrodes were placed on the ice and allowed to cool down before 2 μL and 4 μL of 10 mM PBSE in DMF were added on GC and RDE respectively. The electrodes were incubated for 15 min to allow the non-covalent linkage between MWNT and PBSE. Then the electrodes were rinsed by DMF and 100 mM PBS pH 7.6 sequentially to remove excessive PBSE. HRP solution was prepared by weighing 5 mg HRP dissolving into 1 mL 20 mM PBS pH 7.6. The bi-enzyme solution was simply prepared by mixing 5 μL of alcohol oxidase solution and 5 μL HRP solution. 10 μL of bi-enzyme solution was drop casted on the electrodes and incubated on ice for 30 min for enzyme immobilization. The electrodes were rinsed with 100 mM PBS pH 7.6 to remove unimmobilized enzyme.

For cyclic voltammetry, the potential range for bi-enzyme modified GC was performed from 0.7 V to 0.2 V with scan rate 20 mVs$^{-1}$ and sample interval 0.001 V for one cycle. The initial potential for amperometric I-t curve collected by constant potential amperometry with rotating disc electrode was 0.45 V with 0.1 s interval for data collection.

Hydrolysis of Methyl Salicylate

The methyl salicylate was mixed with 0.1866 M KOH in 15 mL falcon tube. The falcon tube was sealed and placed in boiling water bath for 30 minutes hydrolysis. Then the falcon tube was cooled down to room temperature before adding phosphoric acid to neutralize the pH to 7.6.

Results and Discussion

Electrochemical Response of Methanol on Bi-Enzyme Modified Electrode

Figure 12:
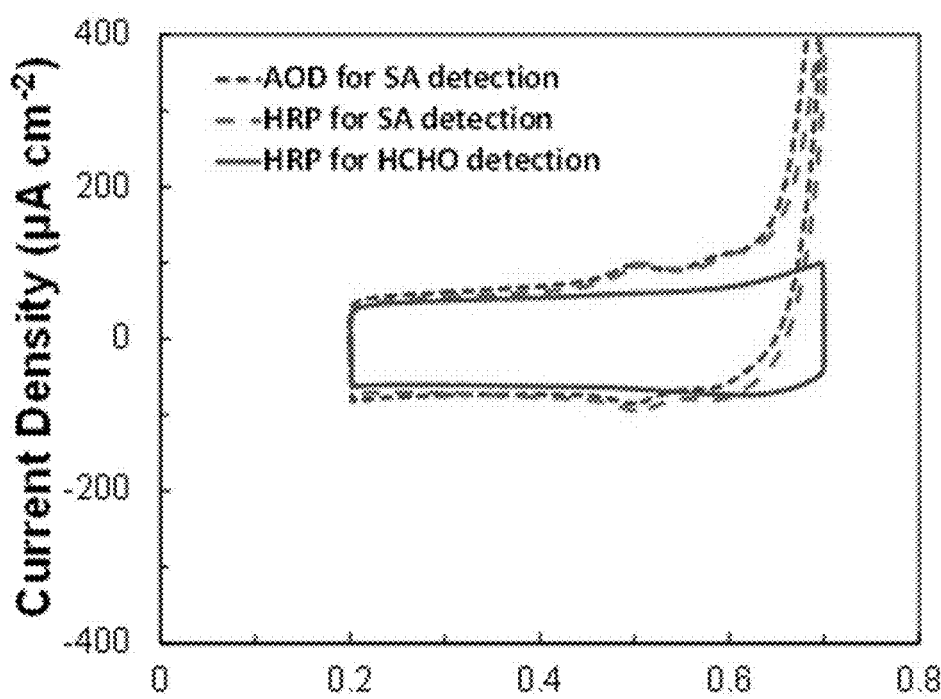
FIG. 12 illustrates CV responses of 5 mM formaldehyde and 5 mM salicylic acid on a monoenzyme (HRP or AO) modified electrode.
Figure 13:
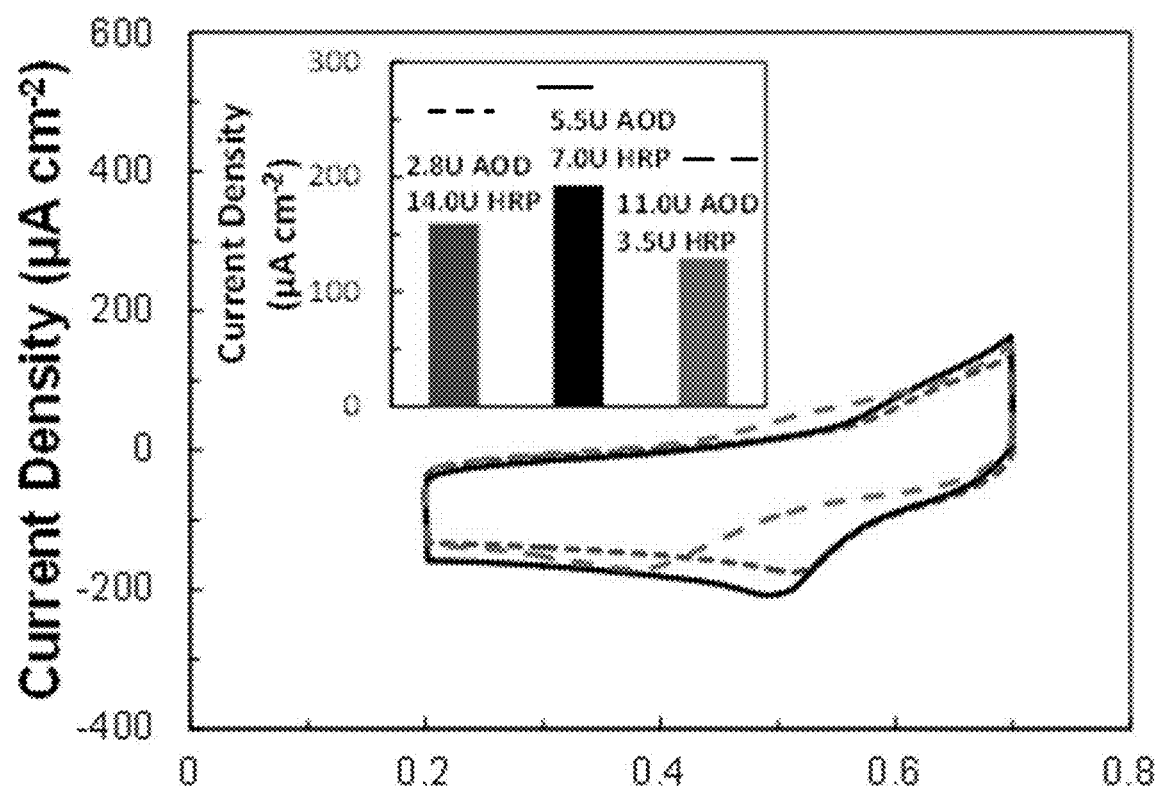
FIG. 13 illustrates CV responses of 1.88 hydrolyzed methyl salicylate on GC electrodes modified by a different ratio of AO and HRP enzymes.

The bi-enzyme modified GC electrode prepared as described above was characterized by 3 mM methanol in electrochemical cell by CV. In order to compare the behavior of bi-enzyme modified GC electrode, monoenzyme modified GC (GC electrodes only modified by alcohol oxidase or horseradish peroxide) were also characterized by 3 mM methanol, respectively. In the FIG. 11(a), the reduction of hydrogen peroxide catalyzed by HRP was observed with an onset of reduction of 0.6 V and peak current of 0.45 V. However, by only modification of AO or HRP, no significant redox peak can be observed, this demonstrates methanol cannot be directly detected on the electrode with no functional enzyme to catalyze reaction, nor by hydrogen peroxide produced by AO without further electron transfer. However, the possibility also exists that the produced formaldehyde after oxidation of methanol with AO can be reduced on the electrode to display reduction signal. Moreover, the methanol based methyl salicylate detection can also be interfered by salicylic acid produced after the hydrolysis of methyl salicylate. Thus, the experiment was also carried out to illustrate that the produced formaldehyde by methanol oxidation by AO does not have any electrochemical signal because no redox peak appears at the potential range of interest (FIG. 12). The salicylic acid produced after hydrolysis of methyl salicylate, although detectable through oxidation and reduction, is much weaker and negligible compared to the electrochemical signal from methanol (FIG. 12). It demonstrates the methanol is the only compound which can be reliably detected on the bi-enzyme modified electrode, and further illustrates that the methanol can be detected on the electrode and corresponds to the amount of methyl salicylate in the sample.

Electrochemical Response of Hydrolyzed Methyl Salicylate on Bi-Enzyme Modified Electrode Similarly, the behavior of bi-enzyme modified GC electrode prepared as stated in introduction section was evaluated by 1.88 mM hydrolyzed methyl salicylate in electrochemical cell by CV. In order to evaluate the function of bi-enzyme modified sensor compared to the monoenzyme and non-enzyme modified cases, in addition to the bi-enzyme modified GC electrode, monoenzyme and non-enzyme modified (AO modified only, HRP modified only, and no enzyme modified GC electrodes) were also evaluated to determine the behavior of bi-enzyme modified electrode for methyl salicylate measurement. Similar results to methanol evaluation can be obtained from FIG. 11B, which demonstrates the bi-enzyme modified electrode can be applied for methyl salicylate detection based on the reduction peak of hydrogen peroxide appears at 0.45 V. In this reaction, the hydrolyzed methyl salicylate containing methanol was added into the electrochemical cell. The methanol was oxidized to formaldehyde and oxygen was reduced to hydrogen peroxide, which further obtained the electron from the electrode and displays the reduction current. The non-enzyme modified and monoenzyme modified cases do not have the similar electrochemical reduction signal obtained from the bi-enzyme modified electrode. In the AO modified-only case, although methanol within the hydrolyzed methyl salicylate can be oxidized and hydrogen peroxide was produced as the product, hydrogen peroxide was not quite electrochemically active among that potential region which limits the electrochemical signal directly produced by hydrogen peroxide reduction without the help of HRP. In the HRP modified-only and non-enzyme modified only cases, methanol can neither react with HRP nor directly reduced on the electrode to give out signal. Additionally, salicylic acid, which is also present in the sample, can give little electrochemical signal. This demonstrates only the bi-enzyme modified electrode can be applied to methyl salicylate detection.

Enzyme ratio of AO and HRP was also optimized to achieve the highest sensitivity of methyl salicylate detection. This was carried out by different combination of enzyme ratios (2.8 U AO/14.0 U HRP, 5.5 U AO/7.0 U HRP and 11.0 U AO/3.5 U HRP). The results showed 5.5 U AO/7.0 U HRP (5 μL AO and 5 μL 5 mg/mL HRP) was the ratio providing highest sensitivity and will be applied to modify the electrode for following quantitative determination FIG. 13).

Figure 14A:
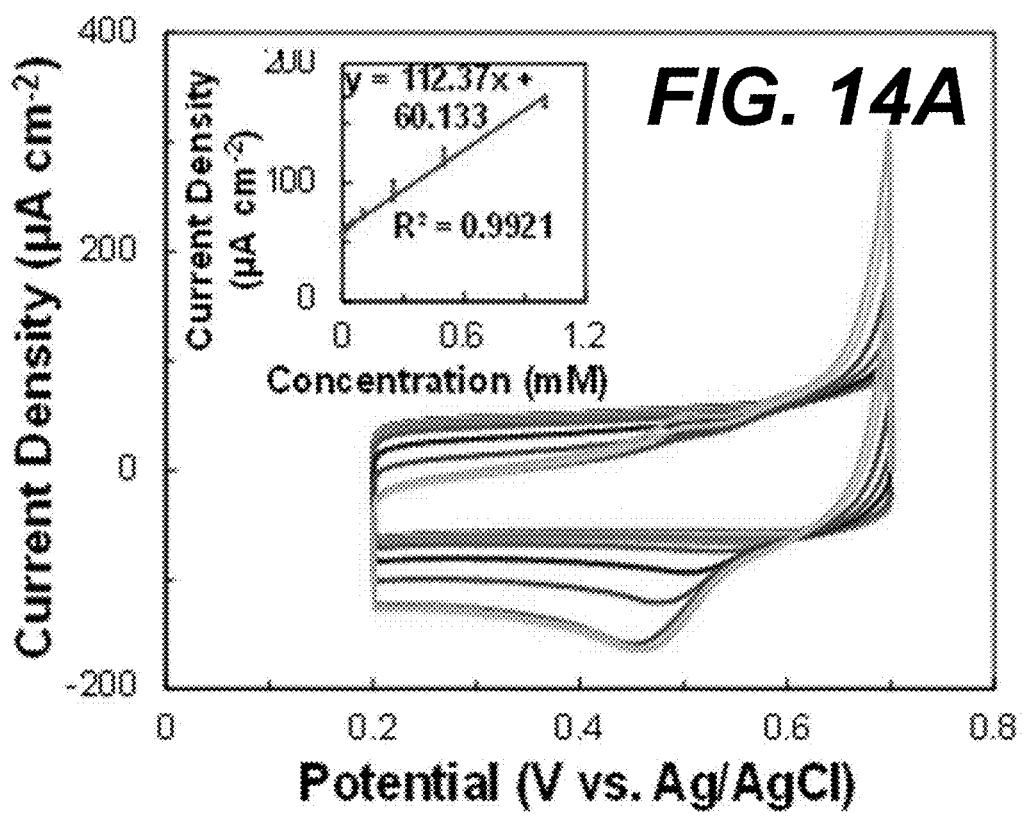
FIGS. 14A and 14B illustrate CV responses of hydrolyzed methyl salicylate from 0, 1 μM to 3 mM on a bi-enzyme modified GC electrode (FIG. 14A) (insert shows current density versus concentration) and ameprometric 1-t curve of hydrolyzed methyl salicylate from 0, 0.1 to 1 mM on a bi-enzyme modified RDE (FIG. 14B) (insert shows current density versus concentration).
Figure 14B:
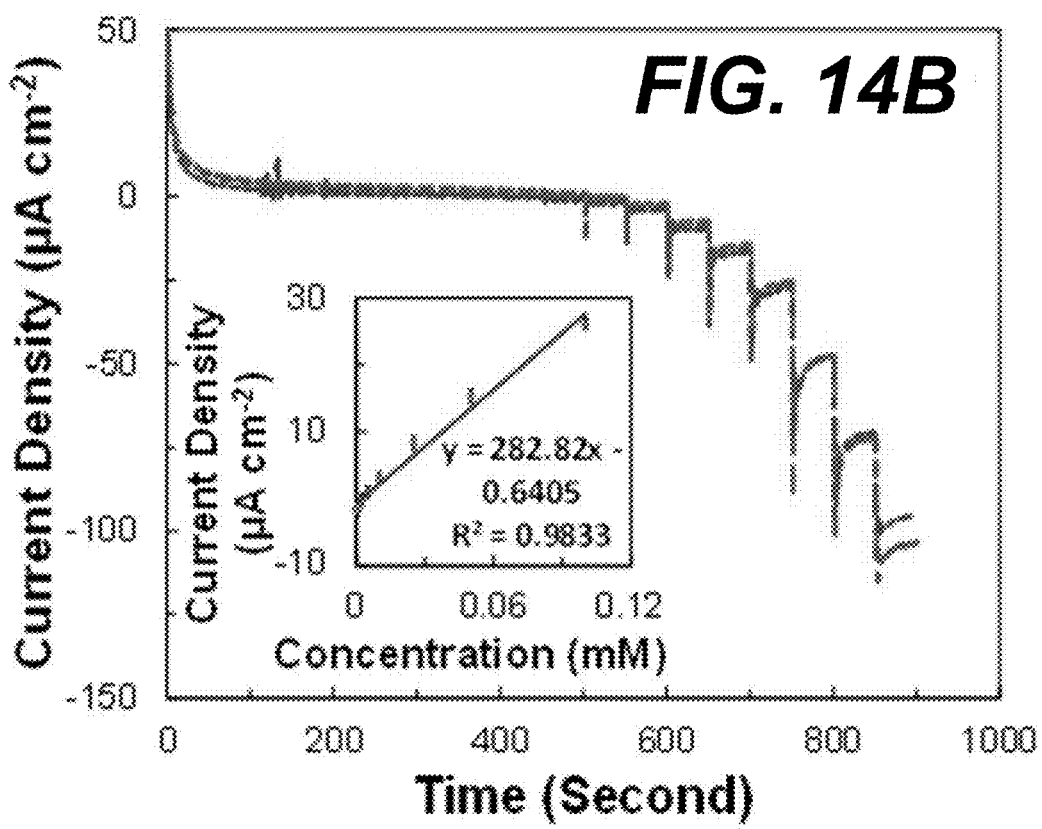

Electrochemical Responses of Hydrolyzed Methyl Salicylate by Cyclic Voltammetry and Constant Potential Amperometry The GC electrode was prepared and modified as described in experiment. Hydrolyzed methyl salicylate was added stepwise to form different concentration gradient from 1 μM to 3 mM followed by the cyclic voltammetry measurement. The above concentration range was chosen by a series of experiments, where the lowest limit was determined based on the noticeable increase in reduction current upon an incremental addition of hydrolyzed methyl salicylate into the electrolyte. Similarly, the upper concentration limit was chosen based on the rate of decrease in oxidation current during subsequent additions of hydrolyzed methyl salicylate. FIG. 14(a) indicates the CV without addition of hydrolyzed methyl salicylate does not display any redox peak due to no reactant in the electrochemical cell. As the concentration of hydrolyzed methyl salicylate increased to 10 µM, small reduction peak for hydrogen peroxide was observed at 0.6 V and the peak current ($I_{pc}$) increases and peak potential ($E_{pc}$) moves negatively to 0.45 V due to the increasing concentration of hydrolyzed methyl salicylate in the electrochemical cell. On the other hand, an oxidation peak around 0.5 V can be observed when the concentration of hydrolyzed methyl salicylate reaches 1 mM and the oxidation peak increases as the concentration of hydrolyzed methyl salicylate increased to 3 mM. This could be attributed to the oxidation of salicylic acid after hydrolysis of methyl salicylate. The electrochemical data such as sensitivity, limit of detection (LOD), limit of quantification (LOQ), were derived from equation 1, 2 and 3 (SD is standard deviation), as well as linear range and initial response (Table 2).

$$\text{Sensitivity} = \frac{\text{Slope of calibration curve } (AM^{-1})}{\text{Area of electrode } (cm^2)} \quad (1)$$

$$LOD = 3.3 \times \frac{SD \text{ of peak current in the absence of analyte } (A)}{\text{Slope of linear calibration curve } (AM^{-1})} \quad (2)$$

$$LOQ = 10 \times \frac{SD \text{ of peak current in the absence of analyte } (A)}{\text{Slope of linear calibration curve } (AM^{-1})} \quad (3)$$

Although CV provides firsthand information of electrochemistry, biosensor applications demand chronoamperometric to eliminate the noise caused by the capacitance and resistance in order to improve overall electroanalytical measurement accuracy. Therefore, constant potential amperometry was performed with RDE. The modified RDE prepared as introduced in experiment was stabilized until 300 second and hydrolyzed methyl salicylate was added stepwise at 50 second interval to generate different concentration gradient from 0.1 µM to 1 mM. The methodology of determining the concentration range was similar to that for CV above. The first observable stepwise increase appears at the concentration of 0.5 µM as it shows in FIG. 14(b). The comparison of electrochemical data was also conducted (Table 2).

The data indicates higher sensitivity for constant potential amperometry (282.82 µA cm$^{-2}$ mM$^{-}$) as opposed to that for cyclic voltammetry (112.37 µA cm$^{-}$mM$^{-1}$). Furthermore, the limit of detection for constant potential amperometry can be lowered down to 0.98 µM as opposed to cyclic voltammetry (22.95 µM) which uses about 1.05 hours accumulating enough sample for detection in a 2 mL electrochemical cell, given that the methyl salicylate production rate is 283 ng hr$^{-1}$ plant$^{-1}$ (Table 2). Though the linear range for constant potential amperometry is narrower than cyclic voltammetry, it is more favored for sensor development due to its high sensitivity and low limit of detection.

Interference of Other Green Leaf Volatiles in Methyl Salicylate Determination

Methyl salicylate is not the only plant volatile that will be produced during the plant infection. The infected plant volatiles contain other compounds which are non-specific to the infection are often released at much higher concentration. A representative set of compounds—cis-3-hexenol, hexyl acetate and cis-3-hexenyl acetate were studied by constant potential amperometry because they are common to most plants. The fungus infection usually results in production of 10 µM of cis-3-hexenol, 1.2 µM of hexyl acetate and 20 µM of cis-3-hexenyl acetate.[23] Constant potential amperometry with RDE was performed to implement interference study. The RDE was preconditioned until 300 second and hydrolyzed methyl salicylate was added to maintain 50 µM of working concentration which is at the middle of linear range. The RDE was further stabilized to 500 second and hydrolyzed green leaf volatiles were added to maintain the working concentration from 10 µM, 50 µM to 1 mM at 50 second interval. The experiment was conducted for all three green leaf volatiles respectively and by adding the same volume of 100 mM phosphate buffer (pH 7.6) as the control. In the interference study, instead of using the common concentration of green leaf volatiles, stepwise addition of green leaf volatiles until 1 mM was conducted.

From FIG. 15, the absolute reduction current density decreases as more phosphate buffer was added into electrochemical cell due to the dilution of hydrolyzed methyl salicylate. However, after adding hexyl acetate, although current density also decreases, it does not decrease as the same pace of control. After adding cis-3-hexenol and cis-3-hexenyl acetate, instead of decreasing, current density increased, which indicates the presence of interference from the three green leaf volatiles. Data further indicate the current density interference increase from 0 (when concentration of green leaf volatile is 0) to 10.30%, 6.50% and 11.59%, respectively (when concentration of cis-3-hexenol, hexyl acetate and cis-3-hexenyl acetate increases to 1 mM) (Table 3). Although there appeared to be high interference, 1 mM is much higher than the maximum green leaf volatile production in natural cases. In presence of 100 µM green leaf volatile, which is also reasonably higher than the usual production of 10 µM of cis-3-hexenol, 1.2 µM of hexyl acetate, and 20 µM of cis-3-hexenyl acetate, results in only 2.36%, 2.14% and 3.43%. With all the interference less than 5.0% at the interference concentration of 100 µM, it is obvious that the interference from green leaf volatiles is not significant in the expected natural situation, although slight interference can be observed in the experimental conditions. The interference from cis-3-hexenol may be attributed to the activity of alcohol oxidase to cis-3-hexenol, although the activity towards cis-3-hexenol is weaker compared to methanol due to its long carbon chain. The same phenomenon was observed from hexyl acetate, whose hydrolysis product also contains cis-3-hexenol. The interference from cis-3-hexenyl acetate might result from the electrochemical activity of cis-3-hexene after the hydrolysis.

Stability and Repeatability

Figure 16:
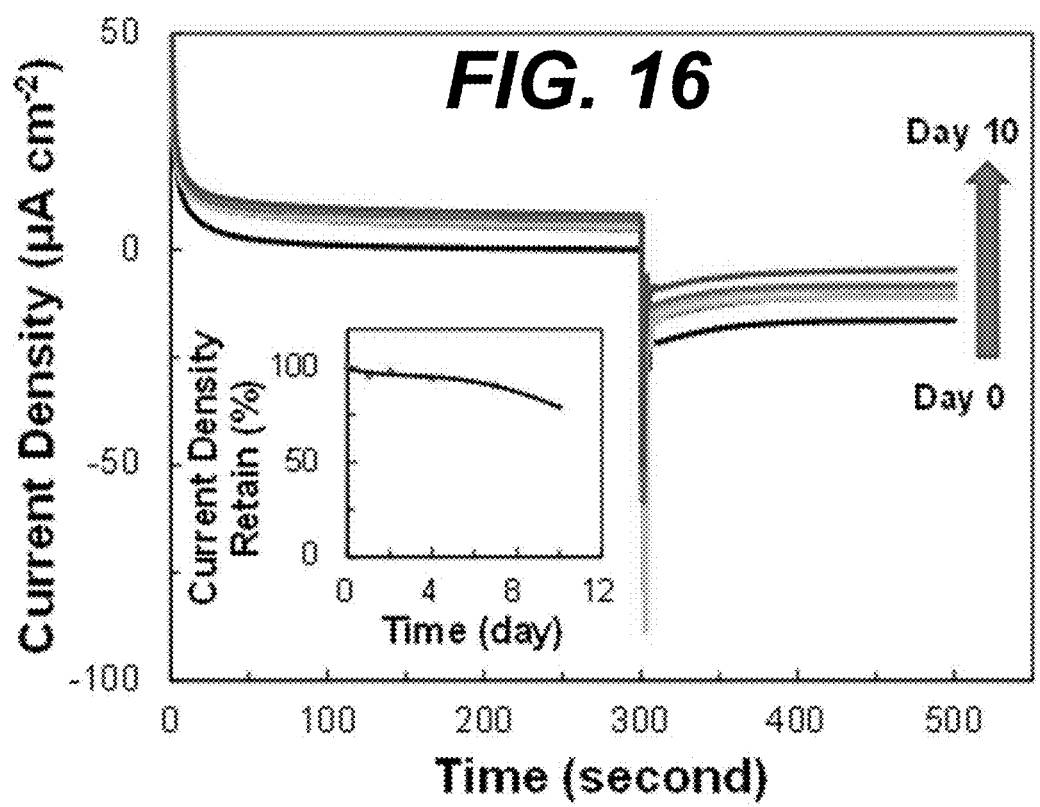
FIG. 16 illustrates the stability of a bi-enzyme modified electrode with 50 μM hydrolyzed methyl salicylate from Day 0 to Day 10 and current density retained against time (insert).

A qualified electrode should also have satisfactory stability. Constant potential amperometry was conducted with 50 µM hydrolyzed methyl salicylate on Day 0, and the net current density was calculated from the current density before and after addition of the hydrolyzed methyl salicylate. The RDE was stored in 100 mM phosphate buffer (pH 7.6) at 4° C. The experiments were repeated on Day 1, 2, 4, 7 and 10 by using the same method. The days were decided by each measurement until a significant decrease of reduction was observed. FIG. 16 shows the current density decreased gradually from Day 0 to Day 10. In Day 1, the current dropped from 100% to 95.27%. However, from Day 1 to Day 4, the electrode behaved relatively stable with retained current density ranges from 94.27% to 98.52%, which could be attributed to the measurement variances rather than losing the stability itself. The study further indicates the electrode was relatively stable for 7 days after the bi-enzyme modified sensor was fabricated, given that more than 90% of the current density was retained. However, on Day 10, the retained current density sharply decreased to 79.13% which might be attributed to the loss of enzyme activity (Table 4). Although the bi-enzyme based sensor stability decreased after 7 days, it had more than 90% activity during the first week after the enzymatic sensor was fabricated. This stability is considered satisfactory, particularly if the sensor is implemented as a one-time use strip.

Figure 17:
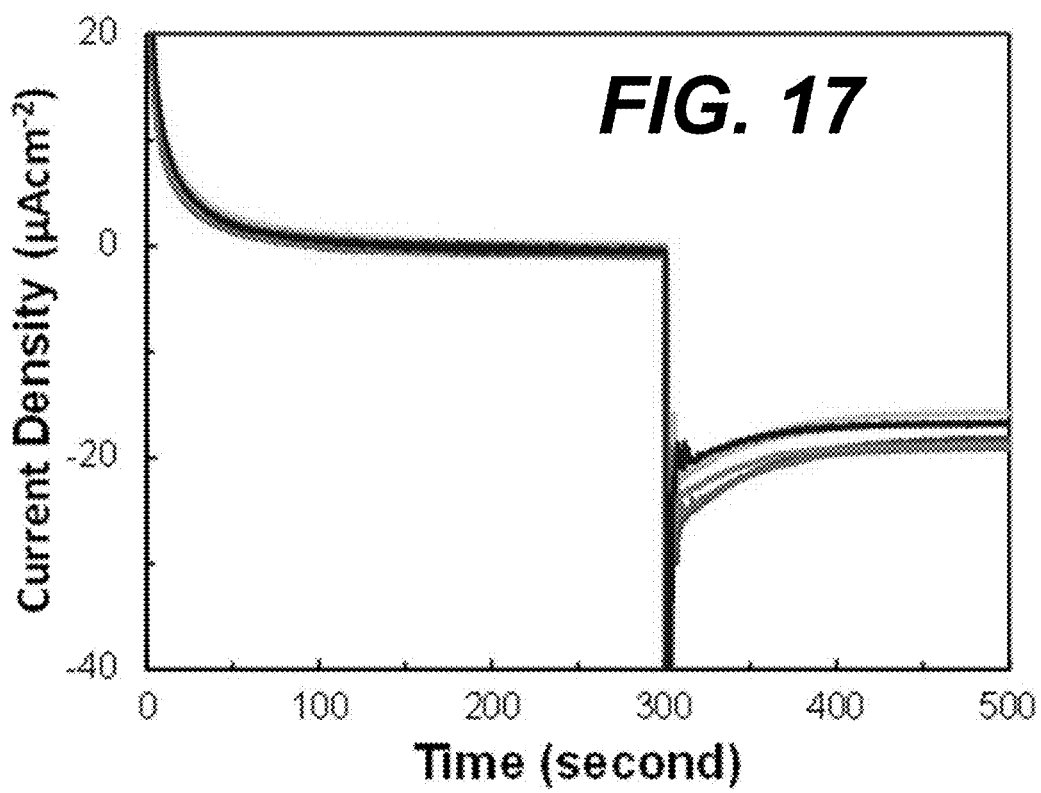
FIG. 17 illustrates the repeatability of a bi-enzyme modified electrode with 50 μM hydrolyzed methyl salicylate.

The repeatability test was also performed to evaluate the data reliability for each electrode prepared. Bi-enzyme modified RDE was used to carry out the measurement with 50 µM hydrolyzed methyl salicylate as illustrated in FIG. 17. Although similar current density was observed initially, after adding 50 µM hydrolyzed methyl salicylate, the current density behaves differently, which could be attributed to difference amount or orientation in enzyme that attached on the electrode and slight difference of each experiment condition. Difference before and after adding hydrolyzed methyl salicylate was used for relative standard deviation (RSD) calculation. The results displays the RSD obtained as 6.6% (Table 5), which is acceptable based on the enzyme modified electrode due to the random orientation and slight differences in each electrode preparation.

Real Sample Study

Real sample study was used for evaluating the behavior of the electrodes of the present example for field application. Wintergreen oil, which is extracted from wintergreen and essentially contains 98% of methyl salicylate, was hydrolyzed as stated before. However, methyl salicylate, which is the main compound in wintergreen oil, is not present in the plant initially. It is only produced enzymatically from a glucoside within the leaves when they are macerated in warm water. In this experiment, wintergreen oil was introduced to simulate the situation when plant produces methyl salicylate due to plant infection. Different amounts of hydrolyzed wintergreen oil with known concentration of MeSA (standard concentration provided in Table 1) were added into the electrochemical cell, and current was collected and compared standard I-t curved collected from pure MeSA (black curve) to calculate MeSA concentration (Table 1). Recovery was determined from calculated concentration divided by standard concentration.

Three replicates were repeated by adding hydrolyzed wintergreen oil for I-t curve collection. The trend is almost the same as pure methyl salicylate (FIG. 18). From Table 1, RSD ranges from 91% to 136%, which demonstrates the capability of the bi-enzyme modified electrode for methyl salicylate detection in natural case. The bias might be derived from other unexpected electrochemical active compounds in wintergreen oil such as α-pinene, myrcene, δ-3-carene, limonene, 3,7-guaiadiene and δ-cadinene reacted directly on electrode. From the RSD in Table 1, it was demonstrated that the real sample experiments were highly repeatable when the concentration is at the center of the linear range due to less than 5%. However, the repeatability decreased when the concentration pushes to the edge of the linear range (upper and lower linear range).

Conclusion

An embodiment of a bi-enzyme modified electrode as a biosensor for methyl salicylate was successfully fabricated and characterized with hydrolyzed methyl salicylate by cyclic voltammetry and constant potential amperometry. Constant potential amperometry demonstrates higher sensitivity and lower limit of detection, which allows short-time sample collection for methyl salicylate. The interference study with three green leaf volatile indicates the biosensor for methyl salicylate detection will not be significantly interfered by green leaf volatile. The biosensor also displays satisfactory stability and acceptable repeatability. Wintergreen oil which was used for real sample study further proved the biosensor fabricated in this example was suitable for on-field demonstration.

TABLE 1

Standard concentration, calculated concentration, recovery, SD and RSD of hydrolyzed Wintergreen oil for real sample study

| Std. Con. (µM) | Cal. Con. (µM) | Recovery (%) | SD (µM) | RSD (%) |
|---|---|---|---|---|
| 2.45 | 2.24 | 91 | 0.28 | 12.38 |
| 4.90 | 5.78 | 118 | 0.28 | 4.90 |
| 9.80 | 12.64 | 129 | 0.29 | 2.29 |
| 24.5 | 31.38 | 128 | 0.96 | 3.06 |
| 49.0 | 59.81 | 122 | 2.71 | 4.53 |
| 98.0 | 133.09 | 136 | 25.36 | 19.05 |

TABLE 2

Electrochemical data for hydrolyzed methyl salicylate from CV and I-t curve

| | Electrode | Sensitivity (µA cm$^{-2}$ mM$^{-1}$) | LOD (µM) | LOQ (µM) | Linear Range (mM) | Initial Response (µM) |
|---|---|---|---|---|---|---|
| CV | GC | 112.37 | 22.95 | 69.55 | 0-1.0 | 10.0 |
| I-t Curve | RDE | 282.82 | 0.98 | 2.97 | 0-0.1 | 0.5 |

TABLE 3

Current density interference of different concentration of green leaf volatiles in 50 µM in hydrolyzed methyl salicylate

| | Current density interference percentage in 50 µM hydrolyzed methyl salicylate (%) | | |
|---|---|---|---|
| Concentration of GLV (µM) | cis-3-Hexenol | Hexyl Acetate | cis-3-Hexenyl Acetate |
| 0 | 0 | 0 | 0 |
| 10 | 0.03 | 0.39 | 0.37 |
| 50 | 0.98 | 0.22 | -0.03 |
| 100 | 2.36 | 2.14 | 3.43 |
| 250 | 3.04 | 1.94 | 3.46 |
| 500 | 6.11 | 3.49 | 6.95 |
| 1000 | 10.30 | 6.50 | 11.59 |

TABLE 4

Stability study of bi-enzyme modified electrode with 50 µM hydrolyzed methyl salicylate

| Time (Day) | Current Density (µA cm$^{-2}$) | Current Density Retained (%) |
|---|---|---|
| 0 | 16.42 | 100 |
| 1 | 15.64 | 95.27 |
| 2 | 16.17 | 98.52 |
| 4 | 15.47 | 94.27 |
| 7 | 14.85 | 90.44 |
| 10 | 12.99 | 79.13 |

TABLE 5

Repeatability study of bi-enzyme modified electrode with 50 μM hydrolyzed methyl salicylate

| Experiment | Background Current Density (μA cm$^{-2}$) | MeSA Current Density (μA cm$^{-2}$) | Net Current Density (μA cm$^{-2}$) |
|---|---|---|---|
| #1 | −0.18 | −18.31 | 18.13 |
| #2 | 0.08 | −15.77 | 15.85 |
| #3 | −0.95 | −19.16 | 18.21 |
| #4 | −0.78 | −16.77 | 15.99 |
| #5 | −0.21 | −18.79 | 18.59 |
| #6 | −0.41 | −16.79 | 16.39 |
| Average | | | 17.19 |
| SD | | | 1.14 |
| RSD | | | 6.6% |

Example 2—Electrochemical Detection of p-Ethylguaiacol on Metal Oxide Nanoparticle Sensor This example describes an embodiment of biosensor electrodes functionalized with metal oxide nanoparticles for detection of p-ethylguaiacol. In other embodiments of the present electrodes described in this example, the metal oxide nanoparticles can also be functionalized with enzymes specific for target stress-induced plant volatiles and/or target plant pathogen-emitted volatile compounds.

The use of metal oxide nanoparticles as the nanoparticle transducer material for an electrode detection surface was explored due to their advantages compared to commonly used nanomaterials. The advantages include the following: metal oxide nanoparticles are catalyst for the dehydrogenation of alcoholic compounds such as aliphatic alcohols, acetic acid etc., which could enhance the plant volatile reaction on the transducer; metal oxides are inexpensive compared to noble metal nanoparticles; some metal oxides have large band gap (greater than 3.3 eV), which can enable them for amperometric signal generation in aqueous solution; and the preparation methods for obtaining desired sizes and shapes of these nanoparticles are easier compared to other nanostructure synthesis. This example describes embodiments with one of two metal oxides, $SnO_2$ or $TiO_2$, as electrochemical detection elements for amperometric sensing. Screen-printed carbon (SP) electrodes were modified with nanoparticles of $SnO_2$ or $TiO_2$ and used for the electrochemical detection of p-ethylguaiacol in simulated fruit volatile samples.

Experimental

Materials

Tin (IV) oxide (<100 nm) and titanium (IV) oxide (~21 nm) nanoparticles obtained from Sigma-Aldrich were used for preparing nanoparticle suspensions. p-ethylguaiacol from Frinton Laboratories, Inc., (New Jersey, US) was used as received. p-ethylphenol was purchased from Sigma-Aldrich and used for interference and synthetic real sample studies. cis-3-hexenol, hexyl acetate, cis-hexen-1-yl acetate, 1-octen-3-ol and 3-octanone obtained from TCI America (Portland, Oreg.) were used as received. All other chemicals used were of analytical grade. All aqueous solutions were prepared using 18.2 MΩ nanopure de-ionized (DI) water. 0.1M electrolyte solution of potassium hydrogen phthalate (KHP) (pH 4) was prepared for all the experiments. Solutions were deoxygenated by purging with pre-purified nitrogen gas for 15 min before each electrochemical measurement.

Apparatus

The working electrode was a screen-printed carbon electrode (SP) modified either with $SnO_2$ nanoparticles or $TiO_2$ nanoparticles. All other conditions were the same as described in Example 1, above.

Electrode Preparation $SnO_2$ and $TiO_2$ nanoparticle suspensions were prepared by ultrasonication of 1 mg of the respective nanoparticles in 1 mL DI water. The $SnO_2$ and $TiO_2$ nanoparticle modified SP electrodes were prepared by drop casting 18 μL (in three steps of 6 μL additions) of the nanoparticle suspension on the SP, followed by drying at 70° C. The cyclic voltammogram (CV) and differential pulse voltammogram (DPV) studies were done in a 10 mL voltammetry cell containing $N_2$ saturated 0.1M potassium hydrogen phthalate (KHP) electrolyte for $SnO_2$ as well as $TiO_2$. The potential range scanned for CV studies were for metal oxide modified SP electrodes at the scan rate of 0.02 Vs$^{-1}$. For DPV the potential scanned was from −0.1 to 0.7 V with the increment of 0.004 V, amplitude 0.05 V, pulse width 0.2 s and pulse period 0.5 s for all electrodes.

Results and Discussion

Electrochemical Response of p-Ethylguaiacol on Metal Oxide Modified SPs

The metal oxide modified electrodes were characterized using cyclic voltammetry in the presence and absence of p-ethylguaiacol. Although acidic conditions favor p-ethylguaiacol oxidation as found in our experiments (data not shown), a pH 4 KHP electrolyte was used in our studies to avoid reaction between metal oxides and electrolyte. The cyclic voltammograms of $SnO_2$ and $TiO_2$ modified electrodes in the presence and absence of p-ethylguaiacol are shown in FIG. 19A and the results demonstrate the better sensitivity of p-ethylguaiacol detection by metal oxide nanoparticle modified electrodes when compared with unmodified screen printed (SP) carbon electrode. In the absence of p-ethylguaiacol, $TiO_2$ showed no redox activity, and $SnO_2$ exhibited broad redox peaks in the potential window of −0.1 to 0.4 V, which correspond to the adsorption and desorption of phthalate ions, a known behavior for $SnO_2$ in KHP electrolyte. In the presence of p-ethylguaiacol, both metal oxides exhibited irreversible peaks at 0.62 V (oxidation) and at 0.2 V (reduction). The irreversible oxidation of p-ethylguaiacol at 0.62V, occurs as per equation 1, where p-ethylguaiacol forms phenoxy radical intermediate, which then reacts with phthalate anion in the electrolyte to form benzoic acid derivative and $H_3O^+$ (second step in equation 4). The irreversible reduction peak in the cyclic voltammograms at 0.2 V could be due to the reduction of phenoxy radical to p-ethylguaiacol. The result suggests that at potentials below 0.2 V, the p-ethylguaiacol oxidation is reversible.

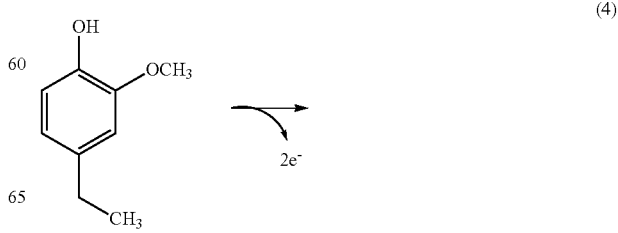

(4)

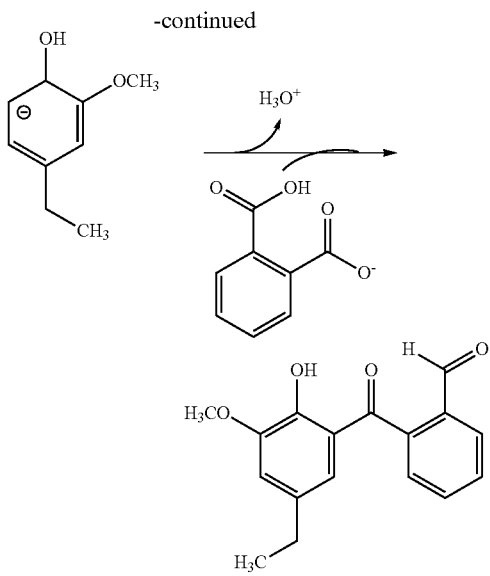

Figure 19B:
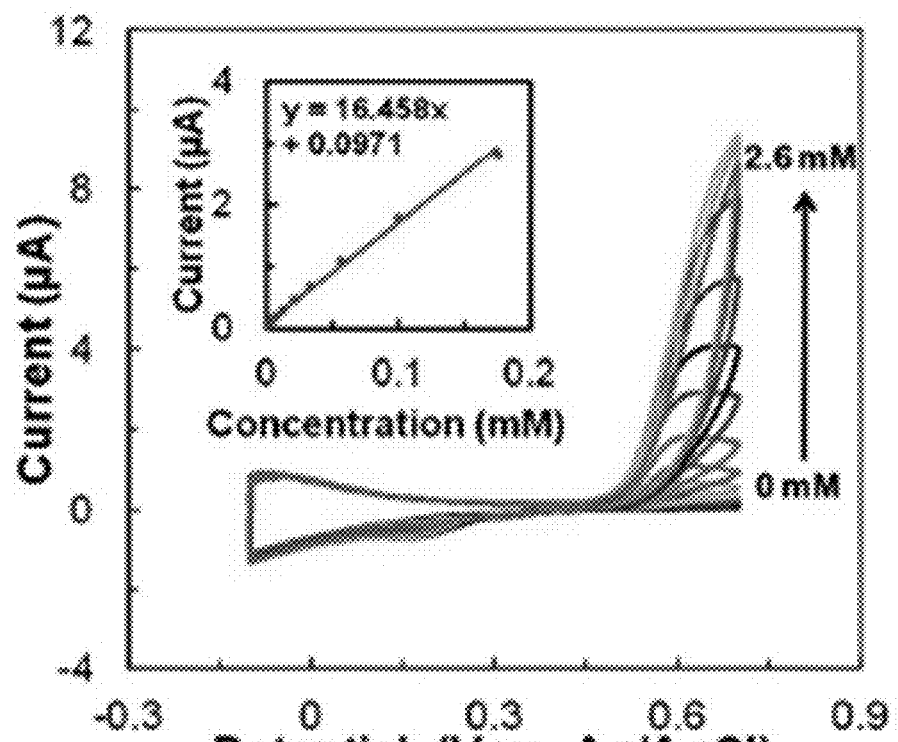
FIGS. 19B and 19C illustrate the concentration effect of ¬p-ethylguaiacol at $SnO_2$—SP (FIG. 19B) and $TiO_2$—SP (FIG. 19C) electrodes.
Figure 19C:
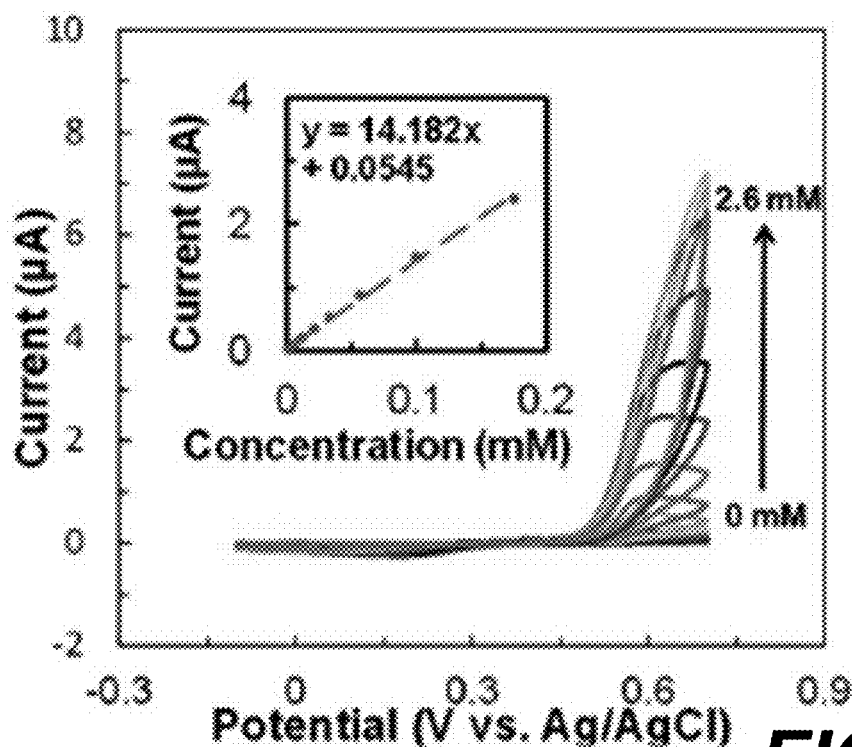

Comparison of p-ethylguaiacol oxidation peaks (at 0.62 V) shows both $SnO_2$ and $TiO_2$ possess similar oxidation currents. The effect of p-ethylguaiacol concentration on the oxidation currents was studied and reported in FIGS. 19B and 19C for $SnO_2$ and $TiO_2$, respectively. The stepwise increase in p-ethylguaiacol concentration from 0.2 µM to 2.6 mM in the electrochemical cell was achieved by adding p-ethylguaiacol from the series of standard concentrations. The above concentration range was chosen by a series of experiments, where the lowest limit was determined based on the noticeable increase in oxidation current upon an incremental addition of p-ethylguaiacol into the electrolyte. Similarly, the upper concentration limit was chosen based on the rate of decrease in oxidation current during subsequent additions of p-ethylguaiacol. The cyclic voltammetry results in FIGS. 19B and 19C show that increasing concentration of p-ethylguaiacol increased the oxidation peak current ($I_{pa}$) of p-ethylguaiacol oxidation on both $SnO_2$ and $TiO_2$ electrodes. The initial response to p-ethylguaiacol additions showed a shift in the p-ethylguaiacol oxidation peak potential ($E_{pa}$) from 0.62 V to 0.7 V. This could be attributed to the increase in acidity of the electrolyte due to more $H_3O^+$ formation (equation 4).

The electroanalytical data such as sensitivity, limit of detection (LOD) at the signal to noise ratio of 3, and limit of quantification (LOQ) of both $SnO_2$ and $TiO_2$ electrodes derived using the equations 1, 2, and 3 from Example 1, above, and are listed in Table 6 respectively.

Comparison of sensitivity values obtained through cyclic voltammogram given in Table 6 reveals that $SnO_2$ had higher sensitivity, lower LOD and LOQ than $TiO_2$ although the difference was not significant. CV provides a firsthand understanding of the electrochemistry of the system. Biosensor applications can also use chronoamperometric or pulse methods to eliminate the noise caused by the capacitance and resistance in order to improve overall electroanalytical measurement accuracy.

Figure 20A:
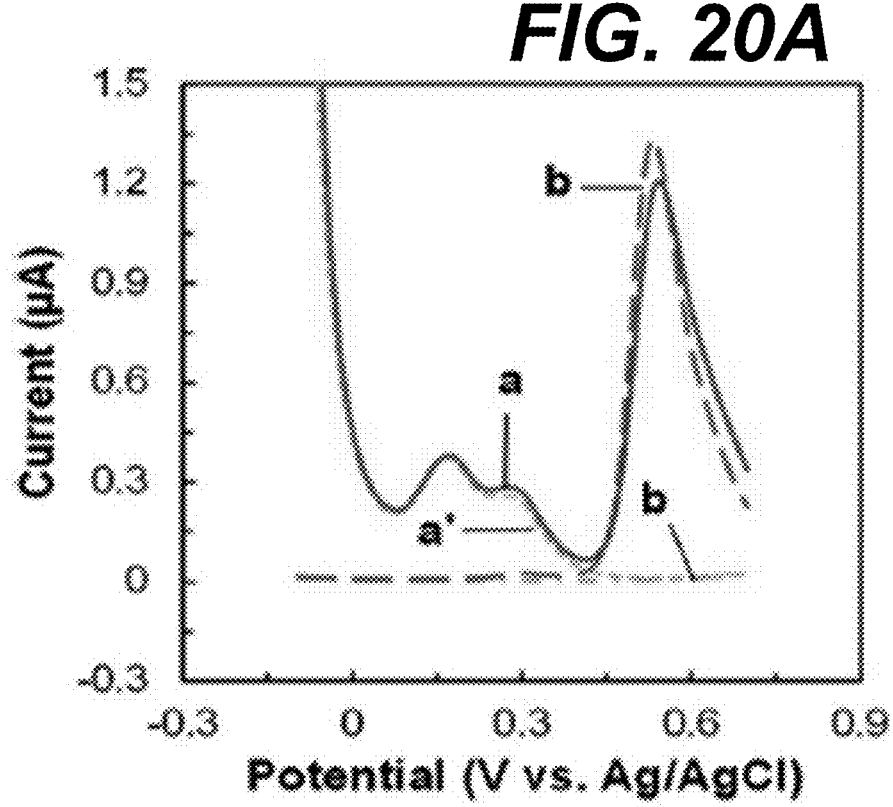
FIG. 20A illustrates differential pulse voltammetry (DPV) responses of $SnO_2$—SP (a and a') and $TiO_2$—SP (b and b') with (a and b) and without (a' and b') the presence of 0.17 mM p-ethylguaiacol.
Figure 20B:
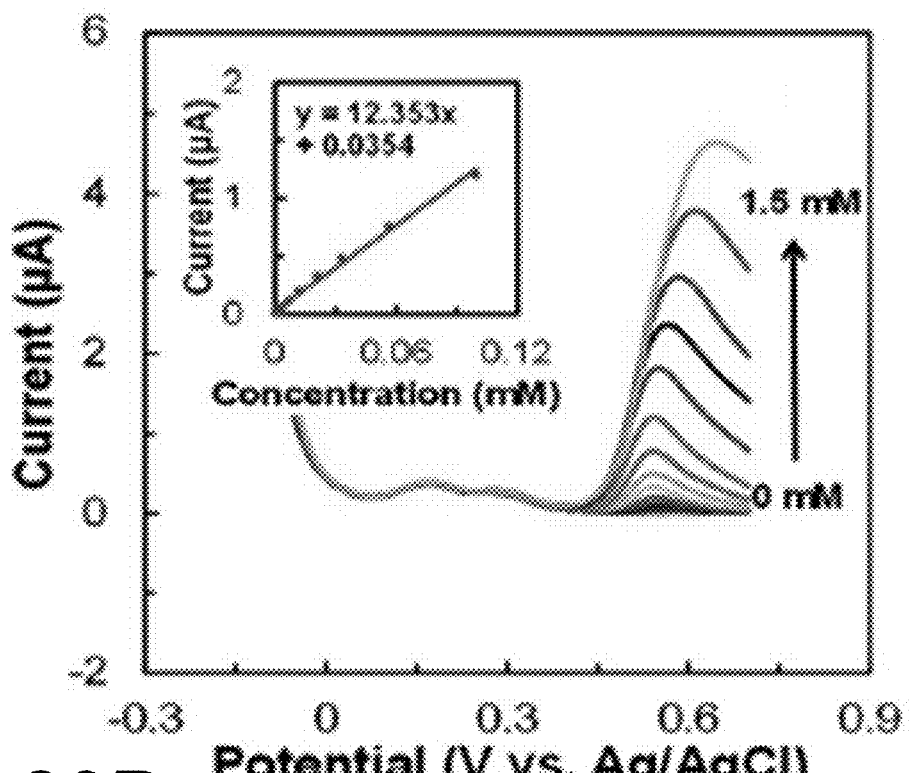
FIGS. 20B and 20C illustrate concentration effect of p-ethylguaiacol on $SnO_2$—SP (FIG. 20B) and $TiO_2$—SP (FIG. 20C) electrodes.
Figure 20C:
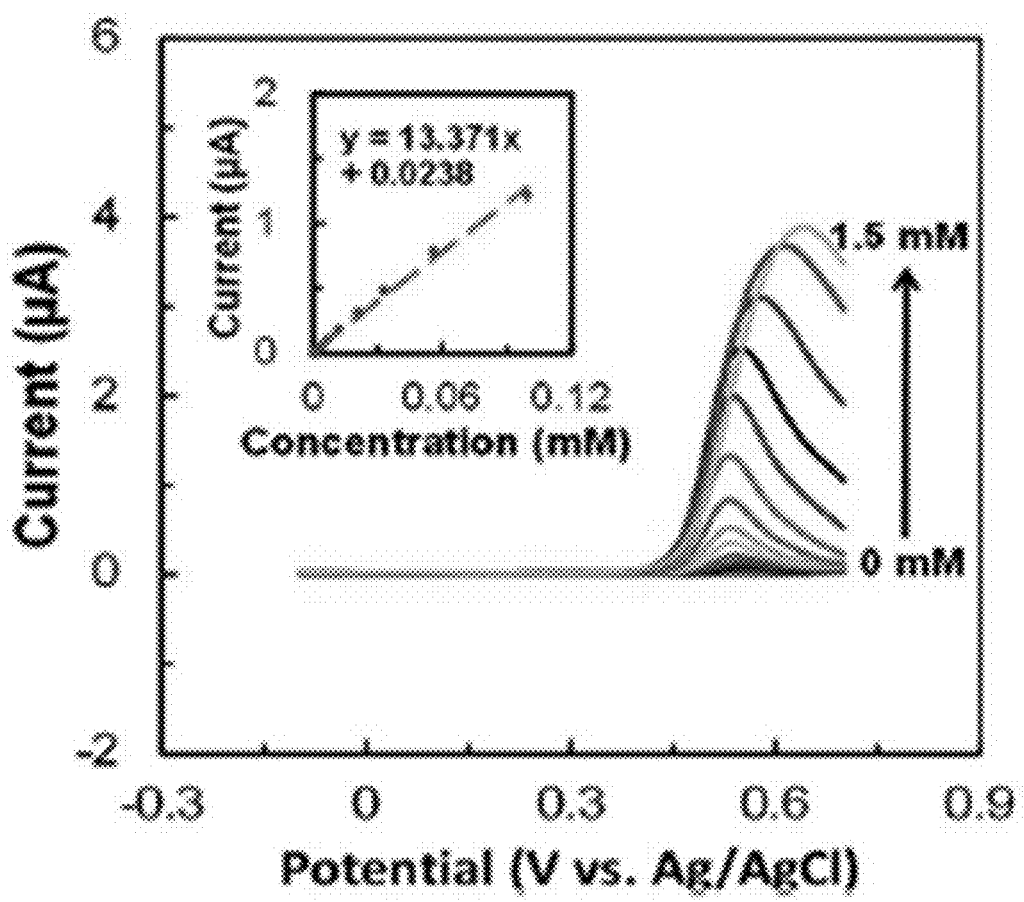

Therefore, differential pulse voltammetry (DPV) was used in a similar manner to CV to study p-ethylguaiacol oxidation between −0.1 and 0.7 V. Compared to unmodified SP electrode, $TiO_2$ and $SnO_2$ modified electrodes display higher sensitivity for p-ethylguaiacol detection (data not shown). Similar to CV results, DPV also showed peaks in the absence of p-ethylguaiacol on $SnO_2$, due to the adsorption and desorption of phthalate ions. In the presence of p-ethylguaiacol, the oxidation peaks appeared at 0.54 V ($E_{pa}$) with similar $I_{pa}$ values for both the electrodes as shown in FIG. 20A. The p-ethylguaiacol characteristic peaks for both $SnO_2$ and $TiO_2$ were similar to that of cyclic voltammograms with ~0.05 V negative shift due to the applied amplitude (0.05 V) during DPV measurements. The peaks currents ($I_{pa}$) for p-ethylguaiacol oxidation increased with the concentration in the range of 0.2 µM to 1.5 mM on both electrodes as shown in FIGS. 20B and 20C. The inset figures show a linear dependency of $I_{pa}$ on concentration. The empirical electroanalytical values derived from the DPV data are also given in Table 6. Due to the elimination of capacitance as well as adsorption-desorption effects in DPV, the values for DPV showed lower sensitivity, but better detection and quantification limits for both electrodes when compared to their corresponding CV values. However $TiO_2$ exhibited better sensitivity and detection limits than $SnO_2$ according to the DPV results, although the difference is not significant (Table 6). DPV values are better representative of the sensing characteristic of the electrodes due to the elimination of parasitic currents from the true oxidation response of p-ethylguaiacol. The results suggest that both $SnO_2$ and $TiO_2$ could be used to construct amperometric sensors for p-ethylguaiacol detection at concentrations relevant to typical infected fruit volatiles.

Reproducibility and Re-Usability Studies

Eight $SnO_2$ and $TiO_2$ modified SP electrodes were prepared under similar conditions and tested for p-ethylguaiacol oxidation using DPV. The DPV peak currents ($I_{pa}$) at 0.54 V, for all eight electrodes were measured at concentration of 2.5 mM. The high concentration was chosen to ensure that even subtle changes in measured currents can be determined. The results (data not shown) showed that the peak current for all eight electrodes varied within 2.48 and 4.85% for $SnO_2$ and $TiO_2$ respectively. The low variability indicates high reproducibility of the observed results for both electrodes.

The reusability or stability of $SnO_2$ and $TiO_2$ modified SP electrodes were tested in a series of DPV experiments at 2.5 mM p-ethylguaiacol concentration on consecutive days for a period of 15 days. $I_{pa}$ of p-ethylguaiacol oxidation in DPVs was measured on each day and percentage decrease in current decrease over time was calculated from the measurements (data not shown). The results showed a loss of activity up to 67% for $SnO_2$ and 81% for $TiO_2$ after 15 days. Though the currents decreased significantly over time, the rate of decrease slowed down after the first two days with no large decrease beyond the first week. The loss in stability could be attributed to the formation of surface oxides and other adsorption effects from the ions present in the electrolyte that tend to slowly poison the electrode over the long-term.

Interference of Other Plant Volatiles in p-Ethylguaiacol Determination

Figure 21A:
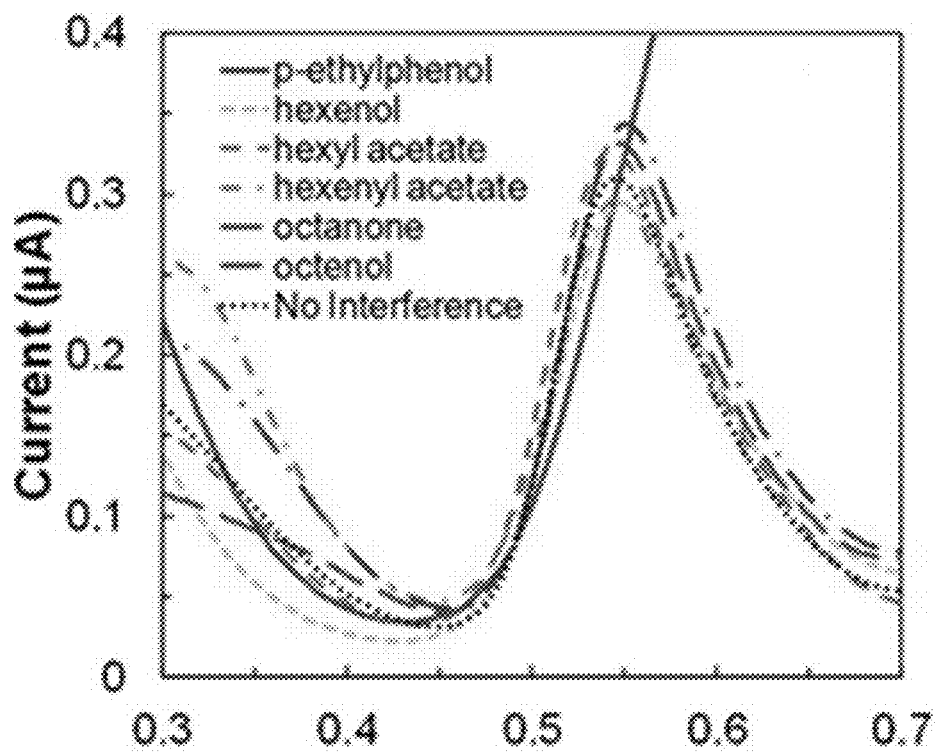
FIGS. 21A and 21B illustrate an interference study of 20.8 μM p-ethylguaicol with 6 different compounds p-ethylphenol, cis-3-hexen-1-ol, hexyl acetate and cis-3-hexen-1-yl acetate, 3-octanone and 1-octen-3-ol on $SnO_2$—SP (FIG. 21A) and $TiO_2$—SP (FIG. 21B) by DPV.
Figure 21B:
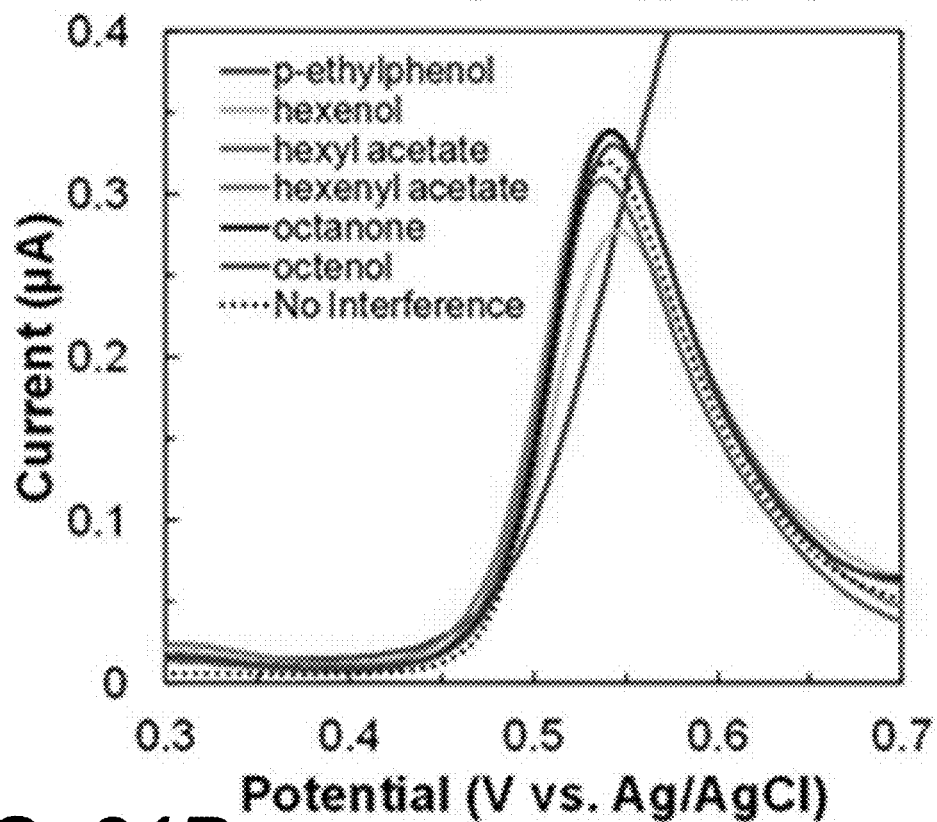

The infected plant volatile contains other chemical compounds that are non-specific to the infection and often released at much higher concentrations than p-ethylguaiacol. A representative set of such compounds was selected and their interference effects on p-ethylguaiacol measurements were studied using DPV. The compounds used to study interference were p-ethylphenol, 3-octanone, 1-octen-3-ol, cis-3-hexenol, hexyl acetate and cis-hexen-1-yl acetate. p-ethylphenol, 3-octanone and 1-octen-3-ol are present in the chemical signature of the *Phytophthora cactorum* itself. The other three compounds cis-3-hexenol, hexyl acetate and cis-hexen-1-yl acetate are green leaf volatiles that are common to most plants. The fungi infected plant typically release 0.2 μM of 3-octanone, 0.2 μM of 1-octen-3-ol, 10 μM of cis-3-hexenol, 1.2 μM of hexyl acetate and 20 μM of cis-hexen-1-yl acetate. Therefore these concentrations were used in our interference study. The experiments were conducted separately for each of the six interfering compounds where the p-ethylguaiacol concentration was kept constant and as low as possible (20.8 μM), but within the linear response ($I_{pa}$) region obtained in DPV. The results showed characteristic peaks for p-ethylguaiacol even in the presence of interfering compounds as shown in FIGS. 21A and 21B for $SnO_2$ and $TiO_2$ respectively. On both $SnO_2$ and $TiO_2$ electrodes, the addition of p-ethylphenol significantly changed the DPV wave above 0.55 V but not at the peak oxidation potential (0.54 V) of p-ethylguaiacol (FIGS. 21A and 21B). As shown by the calculated $I_{pa}$ values in Table 7, p-ethylphenol interference was limited to ±6.7% for $SnO_2$ and $TiO_2$ respectively. Addition of cis-hexen-1-yl acetate showed less than 2% interference on p-ethylguaiacol signal on $TiO_2$, but up to 12% interference on $SnO_2$. The reason for this difference is not clearly understood. Other compounds such as 3-octanone or 1-octen-3-ol or cis-3-hexenol or hexyl acetate did not show any significant interference on the p-ethylguaiacol signal and the interference was limited to less than 2%. The studies above indicate p-ethylguaiacol detection on metal oxide modified electrodes does not suffer any significant interference from both fungal and green leaf volatile compounds.

p-Ethylguaiacol Determination in Simulated Fruit Volatile

The ability of $SnO_2$ or $TiO_2$ for the determination of p-ethylguaiacol in real infected samples was evaluated using simulated chemical mixture that mimics the composition of the real fruit volatile signature. As discussed in the previous section, chemical signature from infected plants will contain both the green leaf volatiles and the volatiles from the pathogen itself. Two sets of samples were used for simulation: (i) only infected fruit volatiles and (ii) both infected fruit and green leaf plant volatiles. The composition of (i) was 20.8 mM p-ethylguaiacol, 2.5 mM p-ethylphenol, 2.5 μM 3-octanone and 2.5 μM 1-octen-3-ol. The composition of (ii) includes all (i) in addition to 10 μM cis-3-hexen-1-ol, 1.25 μM hexyl acetate and 25 μM cis-hexen-1-yl acetate. The above concentrations were chosen based on the composition of typical chemical signature of *Phytophthora cactorum* infection. The experiments were done using DPV and the p-ethylguaiacol oxidation current was measured for detailed analysis. Parameters such as the concentrations added in the experiment, found and relative standard deviation (RSD) obtained from the experiments were calculated from the DPV measurements and are listed in Table 8. The values show that the recovery of p-ethylguaiacol in both simulated samples varied from 91 to 101% for both electrodes with RSD values between 4 and 5%. The analysis shows that both $SnO_2$ and $TiO_2$ electrodes can be used for p-ethylguaiacol determination.

Conclusions

Both $SnO_2$ and $TiO_2$ have been demonstrated to show similar detection capabilities for p-ethylguaiacol based on amperometric determination. Ultra low limits of detection were achieved by both metal oxide electrodes in DPV measurement. Both electrodes exhibited good reproducibility towards p-ethylguaiacol determination. The CV and DPV data along with the chemical reactions established elucidate the electrochemical reaction mechanisms pertaining to the amperometric sensing of p-ethylguaiacol. The electroanalytical data provided in this example can be used for both qualitative and quantitative determination of p-ethylguaiacol. The synthetic sample studies presented illustrate the approach for p-ethylguaiacol sensing during initial stages of *Phytophthora cactorum* infection.

TABLE 6

Comparison of sensitivity, linear range, LOD and LOQ of p-ethylguaiacol at different electrodes obtained using different electrochemical techniques

| Electrode | pH | Technique | EPa (V) | Linear range ($R^2$) | Sensitivity ($\mu A\ cm^{-2}\ mM^{-1}$) | LOD (nM) | LOQ (nM) |
|---|---|---|---|---|---|---|---|
| $SnO_2$-SP | 4 | CV | 0.62 | 0.6 μM-0.17 mM (0.9954) | 232 | 82 | 249 |
| | | DPV | 0.54 | 0.2 μM-0.1 mM (0.9932) | 174 | 62 | 188 |
| $TiO_2$-SP | 4 | CV | 0.62 | 0.6 μM-0.17 mM (0.9972) | 200 | 126 | 382 |
| | | DPV | 0.54 | 0.2 μM-0.1 mM (0.9934) | 188 | 35 | 106 |

TABLE 7

Interference study of 20.8 μM p-ethylguaiacol with 6 different compounds p- ethylphenol, cis-3-hexen-1-ol, hexyl acetate and cis-3-hexen-1-yl acetate, 3-octanone and 1-octen-3-ol by DPV

| Electrode | Compound | Concentration | Current (uA) | Activity (%) |
|---|---|---|---|---|
| $SnO_2$-SP | p-ethylphenol | 0 | 0.3212 | 100 |
| | | 2.50 mM | 0.3533 | 110.01 |
| | cis-3-hexen-1-ol | 0 | 0.2906 | 100 |
| | | 32 μM | 0.2956 | 101.73 |
| | hexyl acetate | 0 | 0.3249 | 100 |
| | | 2 μM | 0.3274 | 100.76 |
| | cis-3-hexen-1-yl acetate | 0 | 0.2672 | 100 |
| | | 32 μM | 0.2972 | 111.21 |
| | 3-octanone | 0 | 0.3301 | 100 |
| | | 2 μM | 0.3320 | 100.57 |
| | 1-octen-3-ol | 0 | 0.3381 | 100 |
| | | 2 μM | 0.3436 | 101.62 |
| $TiO_2$-SP | p-ethylphenol | 0 | 0.3459 | 100 |
| | | 2.50 mM | 0.3227 | 93.3 |
| | cis-3-hexen-1-ol | 0 | 0.2783 | 100 |
| | | 32 μM | 0.2782 | 99.96 |
| | hexyl acetate | 0 | 0.3060 | 100 |
| | | 2 μM | 0.3092 | 101.08 |
| | cis-3-hexen-1-yl acetate | 0 | 0.3336 | 100 |
| | | 32 μM | 0.3400 | 101.91 |
| | 3-octanone | 0 | 0.3334 | 100 |
| | | 2 μM | 0.3391 | 101.70 |

TABLE 7-continued

Interference study of 20.8 µM p-ethylguaiacol with 6 different compounds p- ethylphenol, cis-3-hexen-1-ol, hexyl acetate and cis-3-hexen-1-yl acetate, 3-octanone and 1-octen-3-ol by DPV

| Electrode | Compound | Concentration | Current (uA) | Activity (%) |
|---|---|---|---|---|
| | 1-octen-3-ol | 0 | 0.3278 | 100 |
| | | 2 µM | 0.3308 | 100.90 |

TABLE 8

Simulated sample study using typical chemicals released during *Phytophthora cactorum* infection of plants

| Electrode | Sample | Added (µA) | Found (µA) | Recovery (%) | RSD (%) |
|---|---|---|---|---|---|
| SnO$_2$-SP | Infected fruit | 0.0455 | 0.0417 | 91.65 | 3.65 |
| | | 0.1942 | 0.1947 | 100.26 | |
| | | 0.4816 | 0.4789 | 99.44 | |
| | | 1.5130 | 1.5110 | 99.87 | |
| | Infected fruit with plant | 0.0455 | 0.0495 | 108.79 | 3.88 |
| | | 0.1942 | 0.2011 | 103.55 | |
| | | 0.4816 | 0.4816 | 100.00 | |
| | | 1.5130 | 1.4890 | 98.41 | |
| TiO$_2$-SP | Infected fruit | 0.0421 | 0.0389 | 92.40 | 4.85 |
| | | 0.2218 | 0.2019 | 91.03 | |
| | | 0.5017 | 0.5021 | 100.08 | |
| | | 1.6210 | 1.6500 | 101.79 | |
| | Infected fruit with plant | 0.0421 | 0.0399 | 94.77 | 3.67 |
| | | 0.2218 | 0.2070 | 93.33 | |
| | | 0.5017 | 0.5067 | 101.00 | |
| | | 1.6210 | 1.6420 | 101.30 | |

Example 3—Detection of Methyl Salicylate on Bi-Enzyme Electrochemical Sensor

This example describes an embodiment of a bi-enzyme functionalized electrochemical biosensor of the present disclosure with immobilized salicylate hydroxylase and tyrosinase for detection of methyl salicylate.

Example 1, above, described the application of alcohol oxidase (AO) and horseradish peroxidase (HRP) based bi-enzyme biosensing platform for MeSA detection. This example provides another sensitive and selective enzyme combination for bi-enzyme biosensor based on salicylate hydroxylase and tyrosinase, which allows improved sensitivity and prevents unwanted cross-reactions that could result in false positive signal.

Salicylate, a main compound formed after hydrolysis of MeSA, can be electrochemically detected using salicylate hydroxylase (SH) as the recognition element with high selectivity. The enzyme is immobilized through a tethering chemistry described that binds the enzyme to the multi-walled carbon nanotubes on the surface of glassy-carbon electrodes. Although salicylate acts as the natural substrate for SH, other pseudo-substrates such as benzoate derivatives can also be catalyzed by SH. This issue is addressed by employing a second enzyme—tyrosinase (TYR) as a part of the recognition element, in order to build an enzyme cascade that provides highly selective MeSA detection on the electrode. The reaction scheme of the enzyme cascade and the mechanism behind electrochemical detection are illustrated as steps 1 to 4 in FIG. 22. Salicylate produced from the hydrolysis of methyl salicylate (step 1 in FIG. 22) reacts with SH and generate catechol as the intermediate (step 2). Catechol can be further oxidized enzymatically by TYR to produce 1,2-benzoquinone (step 3). The biochemically generated 1,2-benzoquinone can then be electrochemically reduced to catechol by the electrode thereby regenerating catechol (step 4). Therefore, the amperometric detection of salicylate will be realized through measuring the reduction current of 1,2-benzoquinone.

Experimental

Materials

Tyrosinase (E.C. 1.14.18.1) derived from mushroom (lyophilized powder, 1000 unit/mg solid), methyl salicylate, and farnescene were purchased from Sigma-Aldrich and used as received. Humulene and trimethylbenzene were obtained from Aldrich for the experiments. Multiwalled carbon nanotubes (MWCNTs) were obtained from DropSens Inc. 1-pyrenebutanoic acid succinimidyl ester (PBSE) was purchased from AnaSpec Inc. (Fremont Calif.). Dimethylformamide (DMF), salicylate and NADH were purchased from Acros Organics. FAD and dichlorobenzene were purchased from Alfa Aesar and Eastman respectively. Methanol and phosphoric acid were obtained from Fisher Scientific. All reagents used in this project were analytical grade. 0.1 M phosphate buffer (PB) (pH 7.6) was used as the electrolyte for all experiments. All the aqueous solutions were prepared using 18.2 MΩ nano pure de-ionized (DI) water. Solutions were oxygenated by purging with purified oxygen for 15 min before each experiment.

Recombinant Synthesis of Salicylate Hydroxylase

Salicylate hydroxylase enzyme is not commercially available and therefore was synthesized recombinantly in this work. Gene nahG that codes salicylate hydroxylase in *Pseudomonas putida* can be found from previous publications (You et al. Nucleotide sequence analysis of the *Pseudomonas putida* PpG7 salicylate hydroxylase gene (nahG) and its 3'-flanking region. Biochemistry 30(6), 1635-1641, which is hereby incorporated by reference herein). The nahG gene was codon optimized for expression in *E. coli* and synthesized by GenScript with histidine tag (6X) at N-terminal of the sequence. The recombinant plasmid pTrc99A-nahG was constructed by cloning the nahG gene into pTrc99A that harbors ampicillin resistance gene (ampR) as an antibiotic selection marker. The expression of nahG gene was under the control of P$_{lac}$ and was inducible by addition of isopropyl β-D-1-thiogalactopyranoside (IPTG). Recombinant plasmid was transformed to *E. coli* XL1-blue through electroporation for the purpose of enzyme expression. The resultant transformants of *E. coli* XL1-blue was cultured in test tubes, where each contains 3 mL of LB media (with 100 µg/mL of ampicillin). The strain was cultured overnight aerobically at 37° C. Each of the overnight culture was further inoculated into 250 mL fresh LB media (with 100 µg/mL of ampicillin) and left to grow at 37° C. until OD$_{600}$ reached 0.6. 1 mM of IPTG was added to initiate the expression of salicylate hydroxylase at 20° C. for 8 hours. Cell pellets were collected by centrifugation. Then cell pellets were rinsed with 20 mM PB pH 7.6 twice to remove the LB media before being lysed through French Press. The supernatant was collected as crude extract by centrifugation. The crude extract was purified through fast-protein liquid chromatography with HisTrap™ HP column. Different segments of eluent were tested by a traditional enzyme assay with addition of FAD and cofactor (White-Stevens and Kamin, 1972, Studies of a flavoprotein, salicylate hydroxylase I. Preparation, properties, and the uncoupling of oxygen reduction from hydroxylation. Journal of Biological Chemistry 247(8), 2358-2370; Yamamoto et al., 1965, Salicylate hydroxylase, a monooxygenase requiring flavin adenine dinucleotide I. Purification and general properties. Journal of Biological Chemistry 240(8), 3408-3413, both of which are incorporated by reference herein). The segment with highest enzyme activity was added with glycerol to final concentration of 20%. The enzyme stock was frozen and stored at −80° C. for all the experiments.

Apparatus

Cyclic voltammetry (CV) and constant potential amperometry (CPA) were performed using CHI 920c model potentiostat. Three-electrode system, including a 3 M Ag/AgCl reference electrode, a platinum wire counter electrode, and a glassy carbon (GC) working electrode purchased from Pine Instrument Company were used for electrochemical measurements in a conventional glass voltammetry cell. All experiments were conducted at 22±2° C.

Electrode Preparation and Electrochemical Measurement

GC was first polished on polishing pad with 0.05 micron alumina polishing powder before each experiment. The electrode was cleaned in the ultrasonic cleaner for 5 minutes to remove the polishing powder adhered to the surface of the electrode. The electrode was rinsed with DI water before surface modification with carbon nanotubes (CNTs). CNT suspension was prepared by ultrasonicating 1 mg of multi-walled CNT in 1 mL DMF for an hour. The electrode was modified with CNT by drop casting 16 µL (in 8 steps of 2 µL) followed by drying at 75° C. The electrode was allowed to cool down on the ice before 2 µL of 10 mM PBSE in DMF were added. The electrode was incubated on ice for 15 minutes to allow the non-covalent binding between PBSE and CNT. DMF and 0.1 M PB pH 7.6 were then used sequentially to remove the excessive PBSE from the modified electrode surface. A solution of TYR was prepared by dissolving 5 mg TYR in 1 mL 20 mM PB pH 6.6 and a bi-enzyme solution mixture was prepared by mixing 5 µL of salicylate hydroxylase solution and 5 µL TYR solution. Bi-enzyme immobilized sensor was fabricated by drop casting 10 µL of bi-enzyme solution on the electrode surface, and the electrode was incubated on ice for 30 minutes to allow covalent bind of PBSE and both enzymes. For control studies, mono-enzyme modified electrodes were also fabricated with only one of the two enzymes, namely SH. The mono-enzyme electrode was prepared by drop casting 5 µL of salicylate hydroxylase solution. Electrode was rinsed with 0.1 M PB pH 7.6 to remove any unimmobilized enzyme before measurement. For CV measurements, the potential was scanned from 0.4 V to −0.2 V for bi-enzyme immobilized electrode and from −0.2 V to 0.4 V for both the unimmobilized and mono-enzyme modified electrodes. Scan rate of 20 mV s$^{-1}$ and sample interval of 0.001 V was applied for all CV experiments. The initial potential for constant potential amperometry (CPA) with GC electrode was set to 0.025 V with 0.1 s interval for data collection.

Results and Discussion

Expression and Purification of Salicylate Hydroxylase

Crude extract of SH enzyme synthesized from *E. coli* XL1-blue cells was collected from the French Press after homogenization and centrifugation. The crude extract was first evaluated by traditional SH enzyme assay with addition of FAD as cofactor (White-Stevens and Kamin 1972; Yamamoto et al. 1965). 4 mL of crude extract was obtained and the protein concentration of SH in the crude extract was determined by Bradford assay to be ~35 mg of total protein in 4 mL (Kruger 1994, The Bradford method for protein quantitation. Basic protein and peptide protocols, pp. 9-15. Springer; and Kruger 2009, The Bradford method for protein quantitation. The protein protocols handbook, pp. 17-24. Springer, incorporated by reference herein). Catalytic assay revealed that the total and specific activity of SH were ~23 U and 0.67 U/mg of protein. After purification by fast protein liquid chromatography (FPLC) with HisTrap™ HP column, 0.73 mg of protein with the total activity of 8.96 units was obtained. Although the purification yield was only 39%, the specific activity of SH increased approximately 19 fold to ~12.3 U/mg (Table 9).

Cyclic Voltammetry on Bi-Enzyme Modified Electrode

Control CV experiments were performed first using the mono-enzyme biosensor made of SH immobilized CNT electrodes. The study was carried out by sequentially adding FAD, NADH and salicylate followed by CV measurement after each addition. 100 µL of 0.1 mM FAD was first added due to the requirement of FAD as the cofactor for the SH enzyme reaction. The results of this CV experiment as shown in FIG. 23A demonstrated that FAD does not show any electrochemical activity within the range of −0.2 V to 0.4 V and confirmed that any peak appeared in the subsequent experiments were not that of FAD redox reactions. Then 50 µL of 10 mM NADH was added as the second cofactor and the electrochemical redox activity of NADH was observed using CV between the same voltage window. The objective of this step is to reduce background currents from NADH in the measurements. As shown in FIG. 23A, a small oxidation peak can be found around 0.2 V due to the direct electrochemical oxidation of NADH to NAD$^+$. This corresponds with earlier reports of direct electrochemistry of NADH (Li et al. 2012a, NADH Oxidation catalyzed by electropolymerized azines on carbon nanotube modified electrodes. Electroanalysis 24(2), 398-406; Li et al. 2012b, Quantitative Analysis of Bioactive NAD+ Regenerated by NADH Electro-oxidation. ACS Catalysis 2(12), 2572-2576). In the next step, (sodium) salicylate was added to the electrolyte to a final concentration of 25 µM and another CV scan was performed. Under aerobic conditions, salicylate would be biocatalytically reduced by SH to catechol while simultaneously NADH to NAD+(steps 1 and 2 in FIG. 22) as per the reaction below:

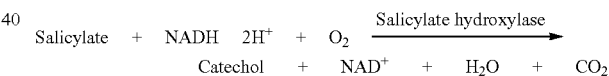

Salicylate + NADH 2H$^+$ + O$_2$ $\xrightarrow{\text{Salicylate hydroxylase}}$ Catechol + NAD$^+$ + H$_2$O + CO$_2$ The resulting CV response is shown in FIG. 23A, where an oxidation peak at 0.15 V was observed upon the addition of 25 µM salicylate. This peak can be attributed to the combined electrochemical oxidation of NADH and catechol on the electrode surface. Catechol is electrochemically oxidized to 1,2-benzoquinone as per the following reaction at 0.15 V:

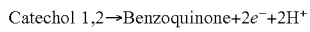

Catechol 1,2→Benzoquinone+2e$^-$+2H$^+$

The reduction wave in all voltammograms below −0.1 V correspond to the reduction of dissolved oxygen present in the system. After understanding the control response of SH immobilized mono-enzyme CNT electrode, similar set of experiments was performed using the bi-enzyme modified CNT electrode that contain both SH and TYR as recognition molecules. The study was carried out by sequential addition of FAD, NADH and salicylate followed by CV measurement after each addition. Similar to the control electrode (mono-enzyme sensor), no significant oxidation/reduction peak can be observed after adding FAD (FIG. 23B). The mild hump noticed at 0.2 V in all the voltammograms in FIG. 23B is a characteristic of the blue copper proteins such as tyrosinase. However, unlike the SH mono-enzyme sensor, addition of NADH did not result in an oxidation peak in the case of bi-enzyme sensor (SH and TYR). This could be due to the reduced transport of NADH from the bulk to the electrode surface due to the presence of additional protein in the CNT matrix on the modified electrode. With addition of 25 μM salicylate, a prominent reduction peak appeared below 0.025 V as shown in FIG. 23B. This distinct reduction peak appears only when both SH and TYR are present in the system and thus can be attributed to the direct electrochemical reduction of 1,2-benzoquinone. 1,2-benzoquinone was produced by the biocatalytic oxidation of catechol by tyrosinase as per the following reaction:

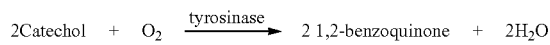

$$2\text{Catechol} + O_2 \xrightarrow{\text{tyrosinase}} 2\ 1,2\text{-benzoquinone} + 2H_2O$$

Unlike the mono-enzyme SH electrode, the bi-enzyme electrode did not exhibit a direct electrochemical oxidation of the catechol in the 0.015 V region of the anodic wave. This suggests that the biocatalytic oxidation reaction of catechol by TYR proceeds at a high rate depleting its surface concentration rather rapidly.

A further set of control experiments were performed on both unimmobilized and TYR-immobilized mono-enzyme electrodes, both in the presence and absence of catechol. The results of this experiment are shown in FIG. 24A, which clearly establishes the catechol redox peaks at ~0.15 V in the absence of TYR on the modified electrode (see indicated curve in FIG. 24A). Another set of control experiments were performed on both unmodified and TYR modified mono-enzyme electrodes, both in the presence and absence of salicylate, the result of which are shown in FIG. 24B. None of the voltammograms shown in FIG. 24B showed a direct electrochemical reduction of 1,2-benzoquinone as observed in FIG. 24B. This indicates that the 1,2-benzoquinone could only be generated in the system through the cascade reactions (steps 1 to 4), when both SH and TYR are present. The results provide conclusive evidence that the bi-enzyme sensor made of SH and TYR enzymes immobilized on CNT matrix provide a reliable and selective detection of salicylate at potentials below 0.15 V.

Determining Optimal Ratio of SH and TYR on Electrode Surface

The loading of either enzymes (SH or TYR) as well as the ratio of their loadings on the CNT electrode surface could influence the electrochemical detection and the resulting sensor performance. The difference in catalytic constants ($K_M$ and $k_{cat}$) between the two enzymes and the difference in mass transport coefficients of the reactants and products can be optimized for the cascade reactions (steps 1 to 4 in FIG. 22). For example, if SH loading on the electrode is insufficient, the cascadic reactions would be limited by catechol generation reaction, leading to low 1,2-benzoquinone generation and low currents on the electrode, thereby directly impacting the sensitivity of salicylate detection. On the other hand, the cascade reactions will also be limited by step 3 (catechol to 1,2-benzoquinone conversion), if TYR loading is insufficient, which can also impact the selectivity of detection. It is desirable to optimize the kinetics and transport inside the enzyme-CNT matrix of the bi-enzyme sensor for optimal conditions for reliable detection of salicylate.

An experimental design approach for fabricating bi-enzyme sensor with different loadings of the two enzymes was prepared in this example. For this purpose, five different volume ratio of SH and TYR enzymes were used for the immobilization on CNT electrode. The loading of SH and TYR used were: 1 μL and 9 μL, 3 μL and 7 μL, 5 μL and 5 μL, 7 μL and 3 μL, and 9 μL and 1 μL respectively on the electrode surface. CV was performed on the five bi-enzyme electrodes in the presence of the same concentration of salicylate, NADH, FAD and oxygen at the experimental pH 7.6 and the results are shown in FIG. 25. The results show that rate of 1,2-benzoquinone reduction (as determined by the slope of the reduction wave below 0.15 V) differed significantly when the enzyme loading ratio was changed. The inset graph in FIG. 25, shows the current density observed at 0.1 V as a function of % volume of SH enzyme in the mixture, i.e. 50% refers to 1:1 volume loading of SH:TYR used for immobilization. The 0.1 V was outside both kinetic and mass transport limited regions and therefore is an ideal reference point to measure the electrochemical rate. It can also be noted from the insert graph in FIG. 25, that the current for a 1:9 SH:TYR ratio was higher than that of 9:1 SH:TYR ratio. The trend indicates that the cascade reactions are limited by the reaction catalyzed by TYR (step 3) rather than the reaction catalyzed by SH (step 2). The highest sensitivity (current density) was observed for a SH:TYR volume ratio of 1:1. This corresponds to 1.83 μg of SH and 25 μg of TYR on the electrode. Consequently, the mixture of 5 μL SH and 5 μL TYR was used in all the remaining experiments to investigate the sensor performance characteristics such as sensitivity and limit of detection.

Electrochemical Response of the Bi-Enzyme Biosensor

Transient performance of the sensor was measured using the CV to determine parameters such as sensitivity, LOD, limit of quantification (LOQ) and reliable linear range for salicylate detection. Since no electrochemical peak can be observed by adding FAD and NADH (FIG. 23B), baseline was collected by CV after adding 100 μL of 0.1 mM FAD and 50 μL of 10 mM NADH. Then salicylate solution was added in steps to different final concentrations 2.3 μM, 4.6 μM, 9.3 μM, 18.6 μM, 27.8 μM and 46.3 μM and after each addition a CV was performed. The resulting voltammograms shown in FIG. 26A indicated that the 1,2-benzoquinone reduction increased progressively (below 0.15 V) as the salicylate concentration in the electrolyte was increased. The reduction currents increased up to 46.3 μM of salicylate beyond which the enzymes exhibited substrate saturation. The effect of substrate limitation on the enzyme kinetics can be explained by the Michaelis-Menten equation below:

$$V = V_{max}[S]/(K_m + [S])$$

As the concentration of substrate [S] is increased, the enzymatic reaction rate will eventually reach saturation and be equal to $V_{max}$. The biosensor parameters were calculated from the CV data at 0.025 V as reference point. The insert graph in FIG. 26B shows the current density at 0.025 V at different concentrations within the linear range of detection. The values were average of 3 replicates. From the data, the sensitivity was calculated to be $21.3 \pm 1.9\ \mu A \cdot cm^{-2} \cdot \mu M^{-1}$ and the LOD and LOQ were determined to be $0.14 \pm 0.02$ μM and $0.42 \pm 0.04$ μM respectively. The linear range of salicylate detection using CV is 0 to 27.8 μM ($R^2=0.99$) as listed in Table 10.

Since CV is a transient technique, it is usually used to obtain a firsthand understanding of the sensor, and a steady state measurement is obtained by constant potential amperometry (CPA). For the CPA, the initial potential was set at 0.025 V and biosensor was stabilized for 2 minutes before adding 100 μL of 0.1 mM FAD and 50 μL of 10 mM NADH at 1 minute intervals, sequentially. After a 1 minute of preconditioning, salicylate was introduced stepwise in different quantities to final concentration of 2.3 µM, 4.6 µM, 9.3 µM, 18.6 µM, 27.8 µM to 46.3 µM. The reduction current was continuously monitored for 1 minute at each concentration until the next step addition of salicylate. For each addition of salicylate, the reduction current reached steady value within short time and at high concentrations began to fade due to the mass transfer limitations (FIG. 26B). Therefore, the highest current measured at each concentration was used for calculating the sensor parameters, which are also reported in Table 10. Compared to the CV, the bi-enzyme biosensor exhibited higher sensitivity (30.6±2.7 µA·cm$^{-2}$·µM$^{-1}$), lower LOD (0.013±0.005 µM) and lower LOQ (0.039±0.015 µM) in the CPA measurements with the same linear range of salicylate detection 0 to 27.8 µM ($R^2$=0.99) (Table 10). Compared to the previously developed bi-enzyme methyl salicylate biosensor with alcohol oxidase and peroxidase, the sensitivity was successfully increased from 0.282 µA·cm$^{-2}$·µM$^{-1}$ to 30.6 µA·cm$^{-2}$·µM$^{-1}$ and lowered the limit of detection from 0.98 µM to 13 nM (Fang et al. 2016). The above parameters allows us to realize the quantification of MeSA produced by diseased plants in less than 3 minutes given that the produced MeSA is captured in 2 mL electrochemical cell for detection based on the MeSA production rate of 283 ng/plant/hr.

Evaluation of Reusability of the Bi-Enzyme Biosensor

It is desired that the biosensor is able to perform repeatedly during multiple measurements within a short period. To this end, reusability of the bi-enzyme biosensor was evaluated for 10 repetitions of salicylate detection, and the results are shown in FIG. 27A. Similar to the sensitivity determination, salicylate solution was gradually added to the electrolyte in the presence of FAD and NADH. The experiment was repeated 10 times and after each repetition, the electrode was taken out and rinsed to remove any residual catechol or 1,2-benzoquinone present on the surface. Four salicylate concentrations within the linear range, namely 4.6, 9.3, 18.5 and 27.8 µM, were analyzed (10 repeatability tests for each concentration, totaling 40 tests).

For low salicylate concentrations of 4.6 and 9.3 µM, the current kept increasing during the first few repetitions (insert graph in FIG. 27A). This could be caused by the residues of 1.2-benzoquinone left on the surface of the electrode from the previous repetition that was not removed completely during rinsing. For low salicylate concentrations of 4.6 and 9.3 µM, the current density remained constant at around 100% of its original value, throughout the 10 repetitions with no obvious loss in sensitivity. On the other hand, at high salicylate concentrations of 18.6 and 27.8 µM, a continuous loss in sensitivity was observed during the 10 repetitions. While the reason for the sensitivity loss during repeatable measurements at high salicylate concentration could be attributed to imbalance in the kinetics and mass transport at the sensor-electrolyte interface. However, detecting salicylate concentrations above 10 µM are generally not necessary for early determination of plant infections as the typical release rate of methyl salicylate by plants would fall below 10 µM (equivalent of 1.52 ppm).

Stability of the Bi-Enzyme Biosensor

In addition to reusability, stability of the biosensor was also evaluated using CPA technique. The bi-enzyme biosensor was fabricated on Day 1 and used to measure different concentrations of salicylate (4.6, 9.3, 18.6 and 27.8 µM) on Day 1, using the previously described experimental procedure. After the experiments on Day 1, the biosensor was rinsed by 0.1 M phosphate buffer (pH 7.6) and stored in 0.1 M phosphate buffer (pH 7.6) with 10% glycerol at 4° C. The same sets of experiments were repeated on Day 2, 4, 6 and 8 and the current densities for salicylate detection were monitored over time. The results of these measurements are given in FIG. 27B. Similar to the results obtained during reusability evaluation, the currents at low salicylate concentrations (4.6 and 9.3 µM) increased during the $2^{nd}$ measurement (on Day 2), likely due the residual catechol or 1,2-benzoquinone present on the electrode that could not be removed during rinsing. The current densities for all other salicylate concentrations decreased gradually after Day 2 due to the gradual deterioration of enzymes on the sensor surface (FIG. 27B). The currents took longer (10 to 60 second) to reach steady values unlike on Day 1, where it reached steady values within 2 seconds. Although long-term storage options and a suitable stabilization method remain to be optimized, the results indicate that the bi-enzyme sensor provides superior detection capabilities at early time periods.

Effect of Interference on the bi-Enzyme Biosensor

In addition to methyl salicylate, other volatile organic compounds (VOCs) can also be released by both healthy and stressed plants. For example, dichlorobenzene (DCB) and 1,2,3-trimethylbenzene (TMB) are among the two most expressed VOCs released by healthy uninfected soybean. Farnesene (FAR) and humulene (HUM) are also reported to be released by soybean aphid infected soybean plant in addition to methyl salicylate. Therefore, the interference caused by FAR, HUM, DCB and TMB on amperometric detection of methyl salicylate using bi-enzyme sensor were evaluated. Since the quantitative detection of methyl salicylate was realized through salicylate measurements, samples have to be hydrolyzed beforehand. Therefore, one potential interfering compound that is produced during this hydrolysis, methanol (MeOH), was also evaluated. In order to maintain the same ionic strength with 0.1 M PB (pH 7.6), 0.19 M KOH was used to hydrolyze the above-mentioned interfering VOCs for 2 hrs in 90° C. water bath. Interfering VOC samples were prepared by adding phosphoric acid to adjust the pH to 7.6 before use. CPA was used for interference evaluation in the presence of 100 µL of 0.1 mM FAD and 50 µL of 10 mM NADH. Very high concentrations (ranging from 9.3 µM to 1.9 mM) of MeOH, FAR, HUM, DCB and TMB were used for the interference study. The upper range of 1.9 mM is 1000 fold higher than the typical VOCs concentration released by infected plants. This was done to ensure conservative estimate of interference under extreme (unfavorable) conditions. The experimental procedure used for interference evaluation was similar to that of earlier CPA measurements. The results of these measurements are shown in FIG. 28. The results indicate that MeOH, HUM, DCB and TMB did not interfere significantly with the salicylate detection current at the operating potential of 0.025 V. Although FAR exhibits a noticeable interference (sensitivity of 0.042 µA·cm$^{-2}$·µM$^{-1}$), the currents are negligible compared to that of the control electrode without interfering compounds (sensitivity of 30.61 µA·cm$^{-2}$·µM$^{-1}$) as shown in the insert graph in FIG. 28. It can be concluded that none of the most common interfering compounds identified above cause significant interference to the bi-enzyme sensor towards the detection of salicylate of methyl salicylate.

Evaluation of Bi-Enzyme Biosensor Using Synthetic Analyte

Based on knowledge of plant volatile signatures, including the composition and relative molarity of the compounds that are released by uninfected and aphid-infected soybean plants, cocktails of VOCs simulating the healthy plant and infected soybean plant volatile signatures were prepared and used as synthetic analyte to evaluate the performance of the bi-enzyme sensor at near-practical conditions. The compositions of these synthetic analytes are given in Table 11. The synthetic analytes were prepared in 0.19 M KOH solution and hydrolyzed at 90° C. in a water bath for 2 hrs. Phosphoric acid was added to adjust pH to 7.6, before the synthetic analyte samples were used for biosensor tests using CPA measurements. For the CPA measurement, the pH adjusted synthetic analyte sample was gradually added to the electrolyte containing 100 µL of 0.1 mM FAD and 50 µL of 10 mM NADH. The results of this measurement shown in FIG. 29 indicate the uninfected synthetic analyte did not exhibit any noticeable reduction current even at high concentrations of the synthetic analyte. On the other hand, for the infected synthetic analyte, a stepwise increase in reduction currents with concentration was observed. The qualitative and quantitative trend of aphid-infected analyte was nearly identical to that of the response from pure salicylate as the analyte (control in FIG. 29). The measured concentration of MeSA in the synthetic analyte was calculated based on the current versus concentration data given in FIG. 26B and the results are tabulated in Table 12. The ratio of the measured concentration to the original concentration added was used to determine the recovery. As shown in Table 12, most concentrations within the linear range exhibit satisfactory recovery (close to 100%), suggesting reasonable sensor accuracy for real sample measurement and quantification. The bi-enzyme biosensor exhibited a sensitivity of 33.49 $\mu A \cdot cm^{-2} \cdot \mu M^{-1}$ for the infected analyte, which was not significantly different from that of the sensitivity obtained for pure methyl salicylate 30.61 $\mu A \cdot cm^{-2} \cdot \mu M^{-1}$ as analyte. This strongly suggests that the bi-enzyme biosensor can be used for reliable detection of real analyte released by infected crops.

Conclusions

A bi-enzyme based electrochemical biosensing platform including salicylate hydroxylase and tyrosinase as recognition elements immobilized onto a CNT matrix on the screen-printed carbon electrode surface was constructed. The detection was based on a cascade of 4 reaction steps that culminate in the electrochemical reduction of 1,2-benzoquinone on the electrode. The fabricated biosensor was evaluated for the selective detection of salicylate, a derivative compound of methyl salicylate present in the volatile signature of infected crops. The bi-enzyme biosensor displayed high sensitivity and nano molar range for limit of detection. The sensor exhibited reasonable reusability and stability. The detection suffered very little interference from other common volatile organic compounds released by both uninfected healthy plant and soybean-aphid infected plants. Synthetic analyte studies confirmed that the sensor can be used for reliable detection of real analytes of crop infection with high selectivity.

TABLE 9

Purification data of salicylate hydroxylase from *E. coli* XL1-blue

| Step | Vol (mL) | Total protein (mg) | Total activity (units) | Specific activity (units/mg) | Purification (fold) | Yield (%) |
|---|---|---|---|---|---|---|
| Crude extract | 4 | 34.8 | 23.3 | 0.67 | (1) | (100) |
| HisTrap ™ HP | 2 | 0.73 | 8.96 | 12.34 | 19 | 39 |

TABLE 10

Sensor performance metrics for salicylate detection using CV and CPA techniques

| Method | Linear range (µM) | $R^2$ | Sensitivity ($\mu A \cdot cm^{-2} \cdot \mu M^{-1}$) | LOD (µM) | LOQ (µM) |
|---|---|---|---|---|---|
| CV | 0-27.8 | 0.99 | 21.3 ± 1.9 | 0.14 ± 0.01 | 0.42 ± 0.04 |
| CPA | 0-27.8 | 0.99 | 30.6 ± 2.7 | 0.013 ± 0.005 | 0.039 ± 0.015 |

TABLE 11

Compositions of synthetic analyte simulating the VOC signature of uninfected and soybean-aphid infected soybean plants

| Uninfected synthetic analyte | | Soybean aphid-infected synthetic analyte | |
|---|---|---|---|
| VOC | Concentration (mM) | VOC | Concentration (mM) |
| Dichlorobenzene | 10 | Methyl salicylate | 10 |
| 1,2,3-trimethylbenzene | 7 | Farnesene | 15 |
| | | Humulene | 10 |

TABLE 12

Simulated sample study with measuring simulated samples for uninfested, infested and salicylate

| Concentration Added (µM) | Concentration Measured (µM) | Recovery (%) |
|---|---|---|
| 4.6 | 4.73 | 102.77 |
| 9.3 | 10.15 | 109.11 |
| 18.6 | 22.76 | 122.34 |
| 27.8 | 28.93 | 104.06 |

Example 4—Detection of Methyl Salicylate on Tri-Enzyme Electrochemical Sensor

This example describes an embodiment of a tri-enzyme functionalized electrochemical biosensor of the present disclosure with immobilized salicylate hydroxylase and tyrosinase for detection of methyl salicylate in combination with tannase or esterase as a third enzyme for hydrolysis of methyl salicylate.

The bi-enzyme systems described above rely on the manual hydrolysis of methyl salicylate (the target stress-induced plant volatile compound) to salicylate and methanol. One of the hydrolysis products then acts as a substrate for the next enzyme in the cascade ultimately producing an electric current detectable at the electrode. However, use of an enzyme for the initial hydrolysis of methyl salicylate was investigated in this example for improvement in sensitivity and/or selectivity. FIG. 30 provides a schematic illustration of a trienzymatic biosensor with tannase, and FIG. 31 illustrates a tri-enzyme system with esterase.

Experimental

Materials

Enzymes and other materials were obtained and/or prepared as described in Example 1 and 3 above. Tannase from *Aspergillus ficuum* (powder, >150 U/g) and esterase from porcine liver (lyophilized powder, >15 units/mg solid) were purchased from Sigma and used as is. Apparatus for electrochemical measurement and electrode preparation was as described above in Examples 1 and 3.

Results and Discussion

As illustrated in FIGS. 30 and 31, methyl salicylate (MeSA) produced by diseased plants undergoes hydrolysis by tannase (FIG. 30) or esterase (FIG. 31) first to generate salicylate and methanol (1). The generated salicylate reacts on salicylate hydroxylase to produce catechol while oxidizing NADH to $NAD^+$ and reducing oxygen to water (2). The formed catechol is further oxidized by tyrosinase and generate 1,2-benzoquinone (3). The detection of methyl salicylate is finally based on the electrochemical reduction to regenerate catechol (4).

Cyclic voltammetry responses of methyl salicylate (MeSA) and salicylate on bi-enzyme and tri-enzyme systems were compared, as illustrated in FIGS. 32A-32D. CV responses of methyl salicylate (FIGS. 32A and 32B) and salicylate (FIGS. 32C and 32D) on salicylate hydroxylase (SH) and tyrosinase (TRY) immobilized bienzymatic biosensor (FIGS. 32A and 32C) were compared to those of on esterase (ES), SH and TYR immobilized trienzymatic biosensors (FIGS. 32B and 32D). The results demonstrate that methyl salicylate cannot react on bienzymatic biosensor including only SH and TYR (FIG. 32A) (without manual hydrolysis of the methyl salicylate as described in the examples above). Significant reduction current was observed from 0.15 V with methyl salicylate on trienzymatic biosensors (FIG. 32B) which is similar to the same concentration of salicylate on both bienzymatic (FIG. 32C) and trienzymatic biosensor (FIG. 32D).

FIG. 33 demonstrates the cyclic voltammetry responses of 92 uM methyl salicylate on trienzymatic biosensor with different volume ratio of esterase (5 mg/mL), salicylate hydroxylase and tyrosinase (5 mg/mL) and the net current density against different esterase volume percentage (Insert). The experiment demonstrates that ratio of ES:SH:TYR=5:5:5 generates the highest net current density.

As shown in FIG. 34, cyclic voltammetry (A) and constant potential amperometry (B) responses of tri-enzymatic biosensor to different concentrations of methyl salicylate were evaluated. Inserted graphs are current density versus concentration. Sensitivity was determined to be 0.78 $\mu A \cdot cm^{-2} \cdot \mu M$ and 1.34 $\mu A \cdot cm^{-2} \cdot \mu M$ by CV and CPA, respectively Conclusions In addition to the SH and TYR-based bi-enzyme biosensor, a novel ES, SH and TYR-based trienzyme biosensor was successfully fabricated for MeSA detection. The trienzyme biosensor does not require a manual hydrolysis of MeSA for the cascade reactions as implemented with the bi-enzyme biosensor. Therefore, a direct detection of MeSA released by diseased plant or the disease-causing fungus can be realized through the tri-enzyme biosensor. The overall cascade reaction and the amperometric signal generation (e.g., sensitivity) are limited by the catalytic activity of the third enzyme, e.g., esterase (or tannase). This could be addressed by employing a higher loading (g/cm2) of the third enzyme and/or by decreasing the diffusion path for MeSA to the enzyme on the surface during its immobilization on the surface.

Example 5—Detection of p-Ethylphenol on Tyrosinase Immobilized Biosensor

This example describes an embodiment of an enzyme functionalized electrochemical biosensor of the present disclosure with immobilized tyrosinase for detection of p-ethylphenol. A characteristic VOC produced by strawberry plants during fungus infection such as *P. cactorum* is p-ethylphenol. Therefore, detection of p-ethylphenol produced by strawberry plants in ultra-low quantities could be used as an effective indicator for crown rot infection. This example describes the successful development of a tyrosinase-based enzymatic biosensor platform for selective detection of p-ethylphenol. Tyrosinase is an effective enzyme that catalyzes tyrosine, L-dopa and other o-diphenols to their corresponding o-quinone derivatives. Additionally, tyrosinase is able to catalyze monophenols to o-phenols (monooxygenase activity) and oxidize o-phenols to corresponding o-quinones (catechol oxidase activity).

Tyrosinase was used as the bio-recognition element in the construction of a biosensor. Tyrosinase biochemically oxidizes p-ethylphenol to produce 4-ethyl-1,2-benzoquinone. The amperometric detection is based on the electrochemical reduction of 4-ethyl-1,2-benzoquinone to 4-ethyl-1,2-hydroquinone on a multiwalled carbon nanotube (CNT) modified electrode. The scheme in FIG. 35 shows the mechanism of amperometric detection of p-ethylphenol. Tyrosinase catalyzes the conversion of p-ethylphenol to 4-ethyl-1,2-benzoquinone in the presence of oxygen. Tyrosinase was immobilized on CNT through a molecular tethering approach described above, where the CNT acts as both immobilization support and conductive transducer.

Experimental

Materials

Tyrosinase (E.C. 1.14.18.1) from mushroom (lyophilized powder, 1000 U/mg solid) was purchased from Sigma-Aldrich and used as received without further purification. Multiwalled carbon nanotubes (CNT) were obtained from DropSens. Pyrenebutanoic acid succinimidyl ester (PBSE) was purchased from AnaSpec Inc. (Fremont, Calif.). Dimethylformamide (DMF) and salicylate, sodium salt were used directly as received from Acros Organics. p-ethylphenol was obtained from Aldrich. Methanol was purchased from Fisher Scientific. Ethanol was obtained from Electron Microscopy Sciences, Hatfield, Pa. Acetone was purchased from BDH chemicals. p-ethylguaiacol was obtained from Frinton Laboratories, Inc., Hainesport, N.J. and used as directed. Ethyl butyrate and methyl hexanoate were purchased from Fluka. Methyl butyrate, 2-pentanone and 2-heptanone were obtained from Aldrich Chemicals. 0.1 M phosphate buffer (pH 6.6) was used as electrolyte for all experiments [25]. 18.2 MΩ nano-pure de-ionized water was used for preparation of all solutions. Solutions were oxygenated by oxygen for 15 min prior to each experiment.

Apparatus

CH Instruments CHI 920c potentiostat was used to perform cyclic voltammetry (CV), differential pulse voltammetry (DPV) and constant potential amperometry. A three-electrode system having a 3 M Ag/AgCl as reference electrode, a platinum wire as counter electrode and a glassy-carbon (GC) electrode all obtained from Pine Instruments was used to carry out the experiments in a custom made 5 mL glass voltammetry cell. All experiments were carried out at a temperature of 22±2° C.

Electrode Preparation

Glassy-carbon electrode was first polished with 0.05 micron alumina power before each experiment. The electrode was then cleaned with ultrasonication for 5 minutes and rinsed by DI water to remove alumina power adhered to the electrode. The CNT suspension was prepared by ultrasonicating 1 mg of CNT in 1 mL DMF for an hour. 16 μL of CNT suspension was drop casted on the glassy-carbon electrode (in 8 steps of 2 μL) followed by drying at 70° C. CNT modified electrode was placed in ice bath to cool down, before adding 2 μL of PBSE in DMF on the CNT modified electrode. The electrode was then incubated for 15 minutes to allow non-covalent binding of CNT with the pyrene group of PBSE. The electrode was rinsed with DMF to remove residual PBSE and then with 0.1 M phosphate buffer (pH 6.6). Tyrosinase (TYR) solution was prepared by dissolving 5 mg of tyrosinase lyophilized powder in 1 mL of 0.1 M phosphate buffer (pH 6.6). The electrode was further immobilized with tyrosinase by drop casting 5 µL of tyrosinase solution and incubated for 30 minutes on ice for covalent binding of PBSE and the enzyme. Excess tyrosinase was removed by rinsing with 0.1 M phosphate buffer (pH 6.6).

Electrochemical Measurement

Cyclic voltammetry (CV) for unmodified CNT electrodes (no TYR immobilized) was performed from 0.2 to 0.7 V with scan rate of 20 mV/s and sampling interval of 0.001 V. For the TYR-modified CNT electrodes the range for CV was −0.2 to 0.4 V with scan rate of 20 mV/s and sampling interval of 0.001 V. Initial potential for unmodified CNT and TYR-modified CNT electrodes during constant potential amperometry was set at 0.13 V with 0.1 s interval for data collection.

Results and Discussion

Determination of Voltage Window for Reliable Detection

Cyclic voltammetry was used to determine the potential window for reliable detection of p-ethylphenol through the electrochemical reduction of 4-ethyl-1,2-benzoquinone (BQ) based on the reaction scheme described in FIG. 35. FIG. 36A shows the voltammograms of unmodified CNT electrode between −0.2 and 0.7 V, in the presence and absence of p-ethylphenol. The electrochemical oxidation of p-ethylphenol can be noticed above 0.45 V during the anodic sweep, while a corresponding reduction was absent. This suggests that p-ethylphenol oxidation at 0.4 V is irreversible. Since the highly selective detection of p-ethylphenol could only be realized based on the reaction scheme in FIG. 35, the electrochemical oxidation of p-ethylphenol should be avoided when a TYR-modified electrode is used for the detection. Therefore, the voltage window was narrowed down to a shorter range from −0.2 to 0.4 V.

FIG. 36B shows the voltammograms of unmodified and TYR-modified CNT electrodes both in the presence and absence of p-ethylphenol. The results demonstrate that p-ethylphenol cannot be detected in the voltage window between −0.2 and 0.4 V on the unmodified CNT electrode, since no significant oxidation or reduction peak could be observed within the range. On the other hand, upon the immobilization of TYR on CNT modified electrode, the detection of p-ethylphenol was realized through the reduction of 4-ethyl-1,2-benzoquinone (BQ) to 4-ethyl-1,2-hydroquinone (HQ) below 0.2 V as per the scheme in FIG. 35. During the anodic sweep, as the potential was increased from −0.2 V to 0.1 V, two prominent oxidation peaks were also observed in FIG. 36B that could be attributed to the two-step electrochemical oxidation of 4-ethyl-1,2-hydroquinone (HQ).

Detection of p-Ethylphenol Using Tyrosinase Modified CNT Electrode

The voltammograms of TYR-modified CNT electrode at different concentrations of p-ethylphenol is shown in FIG. 37A. The reduction peak at 0.13 V (conversion of 4-ethyl-1,2-benzoquinone to 4-ethyl-1,2-hydroquinone) started to increase with the concentration of p-ethylphenol from 0 to 488 µM. The reduction currents appeared to reach saturation above 247 µM of p-ethylphenol, which is likely due to the saturation in enzymatic reaction rate V at high substrate concentrations [S] as explained by the Michaelis-Menten equation:

$$V = V_{max}[S]/(K_m + [S])$$

The reduction current at 0.13 V was plotted against the concentration of p-ethylphenol in the insert of FIG. 37A. The dependence of the current on concentration was linear. The sensitivity calculated as the slope of the insert graph is estimated to be 8.53 $\mu A \cdot cm^{-2} \cdot \mu M^{-1}$. The TYR-modified CNT electrode also exhibited a limit of detection (LOD) of 0.21 µM and limit of quantification (LOQ) of 0.64 µM for the detection of p-ethylphenol (Table 13).

In addition to CV, constant potential amperometry (CPA) was also tested as described in the example above, to provide steady state measurements to determine the sensitivity, LOD and LOQ for the analyte detection. CPA measurements were made using the tyrosinase-modified electrode at 0.13 V (the peak potential for 4-ethyl-1,2-benzoquinone reduction) by adding different quantities of p-ethylphenol to result in a desired final concentration, while continuously monitoring the reduction current over time. Electrodes were stabilized for 2 min before each addition of p-ethylphenol, which was added to the electrolyte in the electrochemical cell at 60-second intervals. The results of this measurement are shown in FIG. 37B. As concentration of p-ethylphenol increased, the reduction current of 4-ethyl-1,2-benzoquinone also increased in all three repetitive trials attempted for this measurement (FIG. 37B). The sensitivity for p-ethylphenol detection was determined to be 4.05 $\mu A \cdot cm^{-2} \cdot \mu M^{-1}$ and the LOD and LOQ were determined to be 0.10 µM (12.2 ppb) and 0.29 µM (35.4 ppb) respectively (Table 13).

The results indicate that the tyrosinase-modified electrode can be reliably used as a biosensor for the detection of p-ethylphenol in the concentration range from 0 to 100 µM. In addition, the detection of p-ethylphenol through the reduction of 4-ethyl-1,2-benzoquinone at low potentials (0.13 V) is advantageous compared to the detection through direct electrochemical oxidation of p-ethylphenol at 0.5 V (see FIG. 36A), because the low potential detection, eliminates the interference other compounds typically present in the strawberry volatile signature that get oxidized at high potentials.

Stability of Tyrosinase Immobilized Biosensor

Constant potential amperometry was also used to evaluate the stability of the biosensor. For this, the tyrosinase-modified electrode was fabricated on Day 1 and its sensitivity towards p-ethylphenol detection was determined using the same procedure explained above between concentrations 0 and 100 µM. After this, the electrode was rinsed with 0.1 M phosphate buffer (pH 6.6) and stored in 20 mM phosphate buffer (pH 6.6) with 10% glycerol at 4° C. The same experiment was repeated on Day 2, Day 4, Day 6, Day 8, Day 10 and Day 12. Current densities at p-ethylphenol concentrations of 10, 25, 50 and 100 µM were compared in FIG. 38. As the result show, the current density started to decrease from Day 2 for all four concentrations (FIG. 38). This could be attributed to the accelerated degradation of the enzyme's activity on the electrode surface over time. About 50% of the current density was retained on Day 8.

Biosensor Performance in the Presence of Interference Compounds

During a biotic stress event such as during *P. cactorum* infection, strawberry plants produce p-ethylphenol in high quantities. However an uninfected healthy strawberry plant also produces and releases a variety of other volatile organic compounds. Compounds such as ethyl butanoate, methyl hexanoate, ethanol, acetone, methyl butanoate, 2-heptanone and 2-pentanone are mostly produced as volatile organic compounds by healthy strawberry plants at all times. The interference from these compounds to the amperometric signal for p-ethylphenol detection is evaluated to avoid false positive detection. Different concentrations of the above-mentioned interfering compounds up to 6.67 mM were analyzed and their interfering currents were compared against the amperometric signal of 10 µM p-ethylphenol. The results of the CPA measurements are shown in FIG. 39. The values for interference currents obtained from the CPA measurements and the corresponding concentration (in both mM and ppm) are tabulated in Table 14. Among all the interference compounds tested in different concentration, only 6.67 mM of 2-heptanone produced more than 3% of current density compared to 10 µM p-ethylphenol. The results prove that none of the interference compound listed above results in significant interference, although some current density peaks are still present due to the disturbance of sample mixing (FIG. 39).

In addition to the interference compounds listed above, p-ethylguaiacol is a volatile organic compound produced simultaneously with p-ethylphenol when strawberry is infected by *P. cactorum*. p-ethylguaiacol can also be used as a marker for leather rot disease detection. Since p-ethylguaiacol is also released along with p-ethylphenol by the infected strawberry plant, the interference of p-ethylguaiacol on p-ethylphenol detection signal was evaluated as described above, and the results are provided in Table 15. Compared to other compounds, p-ethylguaiacol showed noticeable interference of 9.0% at 250 µM (Table 14). However in typical plant volatile signatures, the p-ethylguaiacol is released in much smaller quantities compared to p-ethylphenol and therefore is not a cause for concern for this biosensor.

Evaluation of Biosensor Using Synthetic Analyte Cocktail

In order to evaluate the sensor in near-practical conditions, a synthetic blend (cocktail) of volatile compounds was used as the analyte to mimic the production of volatile organic compounds by healthy strawberries. The cocktail was prepared using 7 compounds at compositions similar to that in the volatile signature of strawberries as listed in Table 15. Experiments were performed with addition of 1 mL synthetic blend (cocktail) added to 1 mL 20 mM phosphate buffer at 120 seconds to mimic the volatile signature of a healthy strawberry plant. The mixed solution of 20 mM p-ethylphenol and 20 mM p-ethylguaiacol was then gradually added at 60-second intervals to mimic the release of p-ethylphenol along with p-ethylguaiacol by infected strawberries in addition to the volatile organic compounds released by the healthy strawberries (synthetic cocktail). The results from the experiments were compared with the control experiment performed by adding pure 20 mM p-ethylphenol without the presence of interference compounds. The results indicate the trend in currents for p-ethylphenol in presence of cocktail was similar to that of the control group that did not contain interference compounds (FIG. 40). In addition, the sensitivity of p-ethylphenol detection for the p-ethylphenol in presence of interfering compounds from cocktail was similar to that of pure p-ethylphenol without any interfering compound. The results demonstrate that the biosensor could be used for reliable detection of p-ethylphenol from a real plant volatile signature with little interference from its constituent compounds Conclusions The CNT based enzymatic biosensor described in this example exhibited high sensitivity, ultra-low detection, and quantification limits for the detection of p-ethylphenol. The biosensor also displayed satisfactory stability. Other volatile organic compounds have been tested for interference, and no significant interference for p-ethylphenol detection was exhibited by any of the compounds tested. Synthetic analyte including p-ethylphenol and other typical volatile organic compounds produced by both healthy and unhealthy strawberry plants was used for evaluating the sensor under near-practical conditions, and the sensor exhibited reliable detection of p-ethylphenol in the synthetic analyte. This research provides a platform for the development of biosensors for early detection of plant diseases and has significant implications in the field of agriculture.

TABLE 13

Linear range, $R^2$ value, sensitivity, limit of detection (LOD) and limit of quantification (LOQ) for tyrosinase-modified CNT biosensor for p-ethylphenol detection by cyclic voltammetry (CV) and constant potential amperometry (CPA)

| Technique | Linear range (µM) | $R^2$ | Sensitivity ($\mu A \cdot cm^{-2} \cdot \mu M^{-1}$) | LOD (µM) | LOQ (µM) |
| --- | --- | --- | --- | --- | --- |
| CV | 0-100 | 0.9950 | 8.53 ± 0.95 | 0.21 ± 0.08 | 0.64 ± 0.25 |
| CPA | 0-100 | 0.9956 | 4.05 ± 0.52 | 0.10 ± 0.02 | 0.29 ± 0.07 |

TABLE 14

Percentage (%) of interference current density resulted from interference compounds compared to 10 µM p-ethylphenol

| Conc. (mM) | EB | MH | Ac | Et | MB | HN | PN | EG |
| --- | --- | --- | --- | --- | --- | --- | --- | --- |
| 0 | 0 ppm | 0 ppm | 0 ppm | 0 ppm | 0 ppm | 0 ppm | 0 ppm | 0 ppm |
|  | 0.0% | 0.0% | 0.0% | 0.0% | 0.0% | 0.0% | 0.0% | 0.0% |
| 0.05 | 5.8 ppm | 6.5 ppm | 2.9 ppm | 2.3 ppm | 5.1 ppm | 5.7 ppm | 4.3 ppm | 7.6 ppm |
|  | 0.7% | 1.2% | 0.3% | 0.2% | 0.4% | 0.7% | 0.4% | 1.4% |
| 0.10 | 11.6 ppm | 13.0 ppm | 5.8 ppm | 4.6 ppm | 10.2 ppm | 11.4 ppm | 8.6 ppm | 15.2 ppm |
|  | 0.0% | 0.2% | −0.1% | −0.2% | −0.2% | 0.4% | 0.4% | 3.6% |

TABLE 14-continued

Percentage (%) of interference current density resulted from interference compounds compared to 10 µM p-ethylphenol

| Conc. (mM) | EB | MH | Ac | Et | MB | HN | PN | EG |
|---|---|---|---|---|---|---|---|---|
| 0.25 | 29.0 ppm 0.8% | 32.5 ppm 0.7% | 14.5 ppm 0.6% | 11.5 ppm 0.9% | 25.5 ppm 0.4% | 28.5 ppm 0.7% | 21.5 ppm 0.5% | 38.0 ppm 9.0% |

*EB: ethyl butyrate;
MH: methyl hexanoate;
Ac: acetone;
Et: ethanol;
MB: methyl butyrate;
HN: 2-heptanone;
PN: 2-pentanone;
EG: p-ethylguaiacol

TABLE 15

Composition of synthetic analyte cocktail including volatile organic compounds (VOCs) produced by healthy strawberry plants

| Volatile organic compound | Concentration (mM) |
|---|---|
| Ethyl butanoate | 20.75 |
| Methyl hexanoate | 16.62 |
| Acetone | 7.42 |
| Ethanol | 7.42 |
| Methyl butanoate | 13.91 |
| 2-Heptanone | 9.72 |
| 2-Pentanone | 3.91 |

REFERENCES

Armstrong, N. R.; Lin, A. W. C.; Fujihira, M.; and Kuwana, T.; Anal Chem, 1976, 48, 741.

Atanassov, P.; Ivnitski, D.; Ramasamy, R. P.; Luckarift, H. R.; Johnson, G. R.; Lau, C. Biofuel cell electrocatalysts using enzyme-carbon nanotube adducts. 2014.

Bakker, E., *Electrochemical sensors*. Analytical chemistry, 2004. 76(12): p. 3285-3298.

Baldwin, I. T.; Kessler, A.; and Halitschke, R.; Curr Opin Plant Biol., 2002, 5, 351.

Berna A. Z.; Lammertyn J.; Saevels S.; Natale C. D. and NicolaI B. M.; Sensor Actuat B-Chem., 2004, 97, 324.

Bru, R., A. Sanchez-Ferrer, and F. Garcia-Carmona, Characteristics of tyrosinase in *AOT—isooctane reverse micelles*. Biotechnology and bioengineering, 1989. 34(3): p. 304-308.

Buttery, R., Seifert, R., Guadagni, D., Ling, L., 1969. Characterization of some volatile constituents of bell peppers. Journal of Agricultural and Food Chemistry 17(6), 1322-1327.

Caboni P.; Sarais G.; Cabras M. and Angioni A.; J Agr Food Chem., 2007, 55, 7288.

Calkins, J. O.; Umasankar, Y.; O'Neill, H.; Ramasamy, R. P., High photo-electrochemicalactivity of thylakoid-carbon nanotube composites for photosynthetic energy conversion. *Energ Environ Sci* 2013, 6, 1891-1900.

Comninellis, C.; and Pulgarin, C.; J Appl Electrochem., 1993, 23, 108.

Cosnier, S. and C. Innocent, *A new strategy for the construction of a tyrosinase-based amperometric phenol and o-diphenol sensor*. Bioelectrochemistry and bioenergetics, 1993. 31(2): p. 147-160.

Costello, B. P. J. d. L.; Ewen, R. J.; Jones, P. R. H.; Ratcliffe, N. M.; Wat, R. K. M., A study of the catalytic and vapour-sensing properties of zinc oxide and tin dioxide in relation to 1-butanol and dimethyldisulphide. *Sensors and Actuators* B 1999, 61, 199-207.

de Faria, R. O., et al., *The tyrosinase produced by Lentinula boryana (Berk & Mont.) Pegler suffers substrate inhibition by L-DOPA*. Food Technology and Biotechnology, 2007. 45(3): p. 334-340.

Diebold, U.; Appl Phys A-Mater., 2003, 76, 681.

Ellis, M. A. and Grove, G. G., *Leather rot in Ohio strawberries*. Plant disease, 1983. 67(5).

Enache, T. A. and A. M. Oliveira-Brett, *Phenol and para-substituted phenols electrochemical oxidation pathways*. Journal of Electroanalytical Chemistry, 2011. 655(1): p. 9-16.

Espin, J. C., et al., *Kinetic characterization of the substrate specificity and mechanism of mushroom tyrosinase*. European Journal of Biochemistry, 2000. 267(5): p. 1270-1279.

Fang, Y., Ramasamy, R. P., 2015. Current and Prospective Methods for Plant Disease Detection. Biosensors 5(3), 537-561.

Fang, Y., Umansankar, Y., and Ramasamy, R. P., Electrochemical detection of p-ehtylguaiacol, a fungi infected fruit volatile using metal oxide nanoparticles. Analyst, 2014, 139, 3804.

Fang, Y., Y. Umasankar, and R. P. Ramasamy, *A novel bi-enzyme electrochemical biosensor for selective and sensitive determination of methyl salicylate*. Biosensors and Bioelectronics, 2016.

Farina, L., et al., *Determination of volatile phenols in red wines by dispersive liquid-liquid microextraction and gas chromatography-mass spectrometry detection*. Journal of Chromatography A, 2007. 1157(1): p. 46-50.

Godfray, H. C. J., Beddington, J. R., Crute, I. R., Haddad, L., Lawrence, D., Muir, J. F., Pretty, J., Robinson, S., Thomas, S. M., Toulmin, C., 2010. Food security: the challenge of feeding 9 billion people. science 327(5967), 812-818.

Hakala, M. A., A. T. Lapvetelainen, and H. P. Kallio, *Volatile compounds of selected strawberry varieties analyzed by purge-and-trap headspace GC-MS*. Journal of agricultural and food chemistry, 2002. 50(5): p. 1133-1142.

Ingram, J., 2011. A food systems approach to researching food security and its interactions with global environmental change. Food Security 3(4), 417-431.

Jeleń, H.; Krawczyk, J.; Larsen, T.; Jarosz, A.; and Golebniak, B.; Main compounds responsible for off-odour of strawberries infected by Phytophthora cactorum. Letters in applied microbiology, 2005. 40(4): p. 255-259.

Katagiri, M., Maeno, H., Yamamoto, S., Hayaishi, O., Kitao, T., Oae, S., 1965. Salicylate hydroxylase, a monooxygenase requiring flavin adenine dinucleotide II. The mechanism of salicylate hydroxylation to catechol. Journal of Biological Chemistry 240(8), 3414-3417.

Keinan, A., Clark, A. G., 2012. Recent explosive human population growth has resulted in an excess of rare genetic variants. science 336(6082), 740-743.

Kessler, A., Baldwin, I. T., 2001. Defensive function of herbivore-induced plant volatile emissions in nature. Science 291(5511), 2141-2144.

Kohlmann, C.; Robertz, N.; Leuchs, S.; Dogan, Z.; Lutz, S.; Bitzer, K.; Na'amnieh, S.; Greiner, L., Ionic liquid facilitates biocatalytic conversion of hardly water soluble ketones. *J Mol Catal B-Enzym* 2011, 68, 147-153.

Kounaves, S. P.; in Handbook of Instrumental Techniques for analytical Chemistry, ed. A. A. Settle, Prentice Hall PTR, Upper Saddle River, N.J., 1997, Ch 37, pp. 709-726.

Kruger, N. J., 1994. The Bradford method for protein quantitation. Basic protein and peptide protocols, pp. 9-15. Springer.

Laothawornkitkul, J., Moore, J. P., Taylor, J. E., Possell, M., Gibson, T. D., Hewitt, C. N., Paul, N. D., 2008. Discrimination of plant volatile signatures by an electronic nose: a potential technology for plant pest and disease monitoring. Environmental science & technology 42(22), 8433-8439.

Li, H., Wen, H., Calabrese Barton, S., 2012a. NADH Oxidation catalyzed by electropolymerized azines on carbon nanotube modified electrodes. Electroanalysis 24(2), 398-406.

Li, H., Worley, K. E., Calabrese Barton, S., 2012b. Quantitative Analysis of Bioactive NAD+ Regenerated by NADH Electro-oxidation. ACS Catalysis 2(12), 2572-2576.

Lian, P.; Zhu, X.; Liang, S.; Li, Z.; Yang, W.; and Wang, H.; Electrochimica Acta, 2011, 56, 4532.

Loake, G., Grant, M., 2007. Salicylic acid in plant defence—the players and protagonists. Current opinion in plant biology 10(5), 466-472.

Luo, P., S. V. Prabhu, and R. P. Baldwin, *Constant potential amperometric detection at a copper-based electrode: electrode formation and operation*. Analytical Chemistry, 1990. 62(7): p. 752-755.

Mahlein, A.-K., Oerke, E.-C., Steiner, U., Dehne, H.-W., 2012. Recent advances in sensing plant diseases for precision crop protection. European Journal of Plant Pathology 133(1), 197-209.

Martorell, N., et al., *Determination of 4-ethylguaiacol and 4-ethylphenol in red wines using headspace-solid-phase microextraction-gas chromatography*. Journal of Chromatography A, 2002. 975(2): p. 349-354.

Nam, S.; Jeon, H.; Kim, S. H.; Jang, J.; Yang, C.; Park, C. E., An inkjet-printed passivation layer based on a photo-crosslinkable polymer for long-term stable pentacene field-effect transistors. *Org Electron* 2009, 10, 67-72

Natale C. D.; Salimbeni D.; Paolesse R.; Macagnano A.; D'Amico A.; Sensor Actuat B-Chem., 2000, 65, 220.

Nieminen, T., et al., *Volatile compounds produced by fungi grown in strawberry jam*. LWT-Food Science and Technology, 2008. 41(10): p. 2051-2056.

Paré P. W. and Tumlinson J. H.; Plant Pysiol., 1999, 121, 325.

Parimi, N. S.; Umasankar, Y.; Atanassov, P.; Ramasamy, R. P., Kinetic and Mechanistic Parameters of Laccase Catalyzed Direct Electrochemical Oxygen Reduction Reaction. Acs Catal 2012, 2, 38-44.

Park, S., H. Boo, and T. D. Chung, *Electrochemical non-enzymatic glucose sensors*. Analytica Chimica Acta, 2006. 556(1): p. 46-57.

Pawliszyn, J., 1999. Applications of solid phase microextraction. Royal Society of Chemistry.

Persaud K. and Dodd G., Nature., 1982, 299, 352.

Pichersky, E., Noel, J. P., Dudareva, N., 2006. Biosynthesis of plant volatiles: nature's diversity and ingenuity. Science 311(5762), 808-811.

Pollnitz, A. P., K. H. Pardon, and M. A. Sefton, *Quantitative analysis of 4-ethylphenol and 4-ethylguaiacol in red wine*. Journal of Chromatography A, 2000. 874(1): p. 101-109.

Ramasamy, R. P.; Luckarift, H. R.; Ivnitski, D. M.; Atanassov, P. B.; Johnson, G. R., High electrocatalytic activity of tethered multicopper oxidase-carbon nanotube conjugates. *Chem Commun* 2010, 46, 6045-6047.

Rassaei, L., et al., *Substrate-dependent kinetics in tyrosinase-based biosensing: amperometry vs. spectrophotometry*. Analytical and bioanalytical chemistry, 2012. 403 (6): p. 1577-1584.

Rayne S. and Eggers N. J.; J Environ Sci Heal B., 2007, 42, 887.

Roosen, C.; Muller, P.; Greiner, L., Ionic liquids in biotechnology: applications and perspectives for biotransformations. Appl Microbiol Biot 2008, 81, 607-614.

Sadana, A.; and Katzer, J. R.; J Catal., 1974, 35, 140.

Saevels S.; Lammertyn J.; Berna A. Z.; Veraverbeke E. A.; Natale C. D. and Nicolaï B. M.; Postharvest Biol Tec., 2004, 31, 9.

Sankaran, S., Mishra, A., Ehsani, R., Davis, C., 2010. A review of advanced techniques for detecting plant diseases. Computers and Electronics in Agriculture 72(1), 1-13.

Schmelz, E. A., Engelberth, J., Alborn, H. T., O'Donnell, P., Sammons, M., Toshima, H., Tumlinson, J. H., 2003. Simultaneous analysis of phytohormones, phytotoxins, and volatile organic compounds in plants. Proceedings of the National Academy of Sciences 100(18), 10552-10557.

Seskar, M., Shulaev, V., Raskin, I., 1998. Endogenous methyl salicylate in pathogen-inoculated tobacco plants. Plant Physiology 116(1), 387-392.

Shulaev, V., Silverman, P., Raskin, I., 1997. Airborne signalling by methyl salicylate in plant pathogen resistance. [Erratum: Apr. 17, 1997, v. 386 (6626), p. 738.]. Nature.

Smil, V., 2001. Feeding the world: A challenge for the twenty-first century. MIT press.

Suneesh P. V.; Chandhini K.; Ramachandran T.; Nair B. G.; Satheesh Babu T. G., Biosens Bioelectron., 2013, 50, 472.

Sunesson, A.; Vaes, W.; Nilsson, C.; Blomquist, G.; Andersson, B.; and Carlson, R.; Appl Environ Microb., 1995, 61, 2911.

Ubeda, C., et al., *Characterization of odour active compounds in strawberry vinegars*. Flavour and Fragrance Journal, 2012. 27(4): p. 313-321.

Ubeda, C., et al., *Glycosidically bound aroma compounds and impact odorants of four strawberry varieties*. Journal of agricultural and food chemistry, 2012. 60(24): p. 6095-6102.

Umasankar, Y., et al., *Three Dimensional Carbon Nanosheets as a Novel Catalyst Support for Enzymatic Bioelectrodes*. Advanced Energy Materials, 2014. 4(6).

Umasankar, Y.; Rains, G. C.; Ramasamy, R. P., Electroanalytical studies on green leaf volatiles for potential sensor development. Analyst 2012, 137, 3138-3145.

Umasankar, Y.; Ramasamy, R. P., Catalytic activity of tyrosinase for potential biofuel cell application. *ECS Transactions* 2013, 45, 9-14.

Umasankar, Y.; Ramasamy, R. P., Highly sensitive electrochemical detection of methyl salicylate using electroactive gold nanoparticles. *Analyst* 2013, 138, 6623-6631.

Umasankar, Y.; Ramasamy, R. P., On the bio-electrocatalytic activity of tyrosinase for oxygen reduction reaction. *Catal Sci Technol* 2013, 3, 2546-2549.

van Rantwijk, F.; Sheldon, R. A., Biocatalysis in ionic liquids. *Chem Rev* 2007, 107, 2757-2785.

Weetall, H. H. and T. Hotaling, A simple, inexpensive, disposable electrochemical sensor for clinical and immuno-assay. Biosensors, 1988. 3(1): p. 57-63.

White-Stevens, R. H., Kamin, H., 1972. Studies of a flavoprotein, salicylate hydroxylase I. Preparation, properties, and the uncoupling of oxygen reduction from hydroxylation. Journal of Biological Chemistry 247(8), 2358-2370.

Wolcott, A.; Smith, W. A.; Kuykendall, T. R.; Zhao, Y. P.; Zhang, J. Z., Photoelectrochemical Water Splitting Using Dense and Aligned TiO2 Nanorod Arrays. *Small* 2009, 5, 104-111.

Yamamoto, S., Katagiri, M., Maeno, H., Hayaishi, O., 1965. Salicylate hydroxylase, a monooxygenase requiring flavin adenine dinucleotide I. Purification and general properties. Journal of Biological Chemistry 240(8), 3408-3413.

You, I. S., Ghosal, D., Gunsalus, I. C., 1991. Nucleotide sequence analysis of the *Pseudomonas putida* PpG7 salicylate hydroxylase gene (nahG) and its 3'-flanking region. Biochemistry 30(6), 1635-1641.

You, I.-S., Murray, R., Jollie, D., Gunsalus, I., 1990. Purification and characterization of salicylate hydroxylase from *Pseudomonas putida* PpG7. Biochemical and biophysical research communications 169(3), 1049-1054.

Zhang, Z., Pawliszyn, J., 1993. Headspace solid-phase microextraction. Analytical chemistry 65(14), 1843-1852.

Zhou, Y.; Umasankar, Y.; Ramasamy, R. P., Enzyme—metal oxide composites as catalysts for enzymatic oxygen reduction reaction. In 225*th Electrochemical Society Meeting,* Orlando, 2014.

Zhou, Y.; Umasankar, Y.; Ramasamy, R. P., Laccase-TiO2 nanoconjugates as catalysts for bio-electrochemical oxygen reduction reaction. *Acs Catal* 2014, in review.

Zhu, J., Park, K.-C., 2005. Methyl salicylate, a soybean aphid-induced plant volatile attractive to the predator Coccinella septempunctata. Journal of chemical ecology 31(8), 1733-1746.

Zhuang Z.; Su X.; Yuan' H.; Sun, Q.; Xiao, D.; and Choi, M. M. F.; Analyst., 2008, 133, 126.

We claim:

1. An electrochemical sensor comprising a volatile detection electrode comprising:
    an electrode substrate; and
    a bio-nanocomposite detection element on a surface of the electrode substrate and in electrochemical communication with the electrode substrate, the bio-nanocomposite detection element comprising:
        a nanomaterial transducer material, and
        an enzyme system capable of specific reaction with a target stress-induced plant volatile compound methyl salicylate, its hydrolysis product, or both, wherein the enzyme system comprises a bi-enzyme or tri-enzyme system comprising at least an enzyme pair selected from the group of enzyme pairs consisting of: salicylate hydroxylase and tyrosinase, and alcohol oxidase and horseradish peroxidase,
    wherein the enzymes are immobilized on the nanomaterial transducer material via a linking group comprising an amine-terminated silane cross-linker attached to the nanomaterial and an amine-amine crosslinker attached to an amine of the amine-terminated silane cross-linker, and
    wherein reaction between the enzymes and methyl salicylate, its hydrolysis product, or both generates an electrical signal, wherein detection of the electrical signal indicates the presence of methyl salicylate.

2. The electrochemical sensor of claim 1, further comprising an electrochemical workstation to provide a current or voltage source to the electrode and for measuring and detecting the electrical signal generated at the detection electrode when the enzymes react with the methyl salicylate, its hydrolysis product, or both.

3. The electrochemical sensor of claim 1, wherein the enzyme pair comprises salicylate hydroxylase and tyrosinase.

4. The electrochemical sensor of claim 1, wherein the enzyme system comprises a tri-enzyme system comprising a first enzyme and the enzyme pair, the first enzyme capable of hydrolyzing methyl salicylate to salicylate and methanol, such that each enzyme in the enzyme pair reacts with the salicylate or methanol in a cascade of reactions, wherein the final reaction in the cascade generates the electrical signal.

5. The electrochemical sensor of claim 4, wherein the first enzyme is selected from the group consisting of: tannase and esterase.

6. The electrochemical sensor of claim 1, wherein the bio-nanocomposite detection element further comprises one or more enzymes capable of specific reaction with a second target volatile compound selected from the group consisting of: a target stress-induced plant volatile compound and a target pathogen-emitted volatile compound.

7. The electrochemical sensor of claim 6, wherein second target volatile compound is selected from the group consisting of: ethyl phenol, ethyl guaiacol, octanone, octanol, a green leaf volatile compound, and combinations of these volatile compounds.

8. The electrochemical sensor of claim 7, wherein the second target volatile compound is selected from ethyl phenol, ethyl guaiacol, or both, and the enzyme capable of reaction with the second target volatile compound is horseradish peroxidase or tyrosinase.

9. The electrochemical sensor of claim 7, wherein the second target volatile compound is octanone and the enzyme capable of detecting octanone is ADH.

10. The electrochemical sensor of claim 6, wherein the one or more enzymes capable of specific reaction with a second target volatile compound is selected from the group consisting of: tyrosinase (TYR), laccase (Lc), bilirubin oxidase (BRO), horseradish peroxidase (HRP), salicylate hydroxylase, alcohol oxidase (AO), alcohol dehydrogenase (ADH), and combinations of these enzymes.

11. The electrochemical sensor of claim 1, further comprising a second volatile detection electrode that detects at least a second target volatile compound other than methyl salicylate, the second volatile detection electrode comprising:
    an electrode substrate; and
    a bio-nanocomposite detection element on a surface of the electrode substrate and in electrochemical communication with the electrode substrate, the bio-nanocomposite detection element comprising:
        a nanomaterial transducer material, and
        one or more enzymes capable of specific reaction with the second target volatile compound or its hydrolysis product, wherein the second target volatile compound is a stress-induced plant volatile compound or a target pathogen-emitted volatile compound, wherein the one or more enzymes are immobilized on the nanomaterial transducer material and reaction between the one or more enzyme and the second target volatile compound generates an electrical signal, wherein detection of the electrical signal indicates the presence of the second target volatile compound.

12. The electrochemical sensor of claim 11, wherein the second target volatile compound is selected from the group consisting of: ethyl phenol, ethyl guaiacol, octanone, octanol, a green leaf volatile compound, and combinations of these volatile compounds, and wherein the one or more enzymes capable of specific reaction with the second target volatile compound is selected from the group consisting of: tyrosinase (TYR), laccase (Lc), bilirubin oxidase (BRO), horseradish peroxidase (HRP), salicylate hydroxylase, alcohol oxidase (AO), alcohol dehydrogenase (ADH), and combinations of these enzymes.

13. The electrochemical sensor of claim 1, wherein the nanomaterial transducer material comprises a nanomaterial selected from the group consisting of: multiwalled carbon nanotubes (MWCNTs), carbon nanoparticles, graphene nanoparticles, metal nanoparticles, and metal oxide nanoparticles.

14. The electrochemical sensor of claim 1, wherein the crosslinkers comprise two or more crosslinkers of varying lengths to accommodate two or more layers of enzymes.

15. The electrochemical sensor of claim 1, wherein the volatile detection electrode is a working electrode of an electrochemical cell further comprising a counter electrode and a reference electrode in electrochemical communication with the working electrode, and a potentiostat configured to supply an electric current to the electrochemical cell and monitor changes in the electric current generated at the working electrode.

16. The electrochemical sensor of claim 15, wherein changes in the electric current in the electrochemical cell are recorded as a cyclic voltammogram, differential pulse voltammogram, or other current response to an applied potential or voltage.

17. The electrochemical sensor of claim 1, further comprising a mediator to facilitate electron transfer from the enzyme to the electrode.

18. An electrochemical sensor comprising a volatile detection electrode comprising:
an electrode substrate; and
a bio-nanocomposite detection element on a surface of the electrode substrate and in electrochemical communication with the electrode substrate, the bio-nanocomposite detection element comprising:
a nanomaterial transducer material, and
an enzyme system capable of specific reaction with a target stress-induced plant volatile compound methyl salicylate, its hydrolysis product, or both, wherein the enzyme system comprises a bi-enzyme or tri-enzyme system comprising at least an enzyme pair selected from the group of enzyme pairs consisting of: salicylate hydroxylase and tyrosinase, and alcohol oxidase and horseradish peroxidase,
wherein the nanomaterial transducer material comprises multiwalled carbon nanotubes (MWCNTs), and the one or more enzymes are immobilized to the MWCNTs via a tethering agent selected from the group consisting of: a 1-pyrene butanoic acid succinamidyl ester (PBSE) tethering agent; 4,4'-[(8,16-dihydro-8,16-dioxodibenzo[a,j]perylene-2,10-diyl)dioxy] dibutyric acid di(N-succinimidyl ester) (DPPSE) tethering agent, and other PBSE-type heterobifunctional tethering agents, and
wherein reaction between the enzymes and methyl salicylate, its hydrolysis product, or both generates an electrical signal, wherein detection of the electrical signal indicates the presence of methyl salicylate.

19. A plant volatile detection system comprising:
(a) a volatile collection reservoir adapted to collect volatile compounds emitted from a plant;
(b) an electrochemical sensor of claim 1 further comprising a counter electrode, and a reference electrode, wherein both the counter electrode and the reference electrode are in electrochemical communication with the volatile detection electrode, and a potentiostat to supply an electric current to the electrochemical cell and monitor changes in the electric current produced at the volatile detection electrode; and
(c) a signal processing mechanism in operative communication with one or more elements of the electrochemical sensor, the signal processing mechanism having data transfer and evaluation software protocols configured to transform raw data from the electrochemical sensor into diagnostic information regarding the presence or absence or levels of the target plant volatile compound.

20. A method for monitoring a condition of a plant or crop of plants, the method comprising:
(1) periodically sampling volatile emissions from the plant or one or more crop plants using a plant volatile detection system, the plant volatile detection system comprising:
(a) a volatile collection reservoir adapted to collect volatile compounds emitted from a plant;
(b) an electrochemical sensor of claim 1 further comprising a counter electrode, and a reference electrode, wherein both the counter electrode and the reference electrode are in electrochemical communication with the volatile detection electrode, and a potentiostat to supply an electric current to the electrochemical cell and monitor changes in the electric current produced at the volatile detection electrode; and
(c) a signal processing mechanism in operative communication with one or more elements of the electrochemical sensor, the signal processing mechanism having data transfer and evaluation software protocols configured to transform raw data from the electrochemical sensor into diagnostic information regarding the presence or absence or levels of the target plant volatile compound; and
(2) determining the presence of a plant disease associated with the presence of methyl salicylate based on the information provided by the signal processing mechanism regarding the presence or absence or levels of methyl salicylate.

* * * * *